United States Patent [19]

Farascioni et al.

[11] Patent Number: 6,142,955

[45] Date of Patent: *Nov. 7, 2000

[54] BIOPSY APPARATUS AND METHOD

[75] Inventors: David Farascioni; George M. Chelednik, both of Bethel, Conn.; Christopher F. Klecher, San Diego, Calif.; Paul A. Matula, Brookfield, Conn.

[73] Assignee: United States Surgical Corporation, Norwalk, Conn.

[*] Notice: This patent issued on a continued prosecution application filed under 37 CFR 1.53(d), and is subject to the twenty year patent term provisions of 35 U.S.C. 154(a)(2).

[21] Appl. No.: 09/040,244

[22] Filed: Feb. 20, 1998

Related U.S. Application Data

[60] Provisional application No. 60/059,548, Sep. 19, 1997, and provisional application No. 60/059,545, Sep. 19, 1997.

[51] Int. Cl.$^7$ ................................................. A61B 10/00
[52] U.S. Cl. ........................... 600/562; 604/170; 606/167
[58] Field of Search .................................... 600/562, 564, 600/565, 560, 567; 604/158, 167, 170; 606/167

[56] References Cited

U.S. PATENT DOCUMENTS

Re. 33,258   7/1990   Onik et al. .
Re. 33,569   4/1991   Gifford, III et al. .

(List continued on next page.)

FOREIGN PATENT DOCUMENTS 0 010 321 A1   4/1980   European Pat. Off. .
0 019 104      11/1980  European Pat. Off. .

(List continued on next page.)

OTHER PUBLICATIONS

Copy of International Search Report for PCT/US98/19422 dated Jan. 12, 1998.

(List continued on next page.)

Primary Examiner—Cary O'Connor
Assistant Examiner—Pamela Wingood

[57] ABSTRACT

A surgical biopsy apparatus is provided which includes a housing; a first elongated tubular member removably mounted in the housing and defining a fluid passageway therein, the first elongated tubular member including: a tapered closed distal end portion adapted to penetrate tissue; a laterally disposed tissue receiving opening formed near the tapered distal end which includes a tissue support surface defining a plurality of holes in fluid communication with the fluid passageway; and a second elongated tubular member rotatably and reciprocatingly disposed coaxially about the first elongated tubular member, the second elongated tubular member having a cutting edge formed at an open distal end thereof and a lateral tissue discharge port formed proximally of the cutting edge.

A method of performing a surgical biopsy is also provided which includes inserting a biopsy apparatus into the tissue of a patient, the biopsy apparatus including an inner tubular member having a tapered penetrating end formed on the distal end and an outer tubular member held longitudinally fixed relative to the inner tubular member during the insertion step; retracting the outer tubular member relative to the inner tubular member to expose a laterally disposed tissue receiving area formed on the inner tubular member; applying suction to a series of openings formed along an inner surface of the tissue receiving area to pull tissue into the tissue receiving area; severing tissue disposed within the tissue receiving area by advancing the outer tubular member over the inner tubular member such that a cutting surface formed on the distal end of the outer tubular member rotates as it passes over the tissue receiving area; and removing the severed tissue sample from the tissue sampling site by retracting the inner tubular member from the outer tubular member until the tissue receiving area is aligned with a lateral opening formed in the outer tubular member wherein a tissue stripping plate urges the tissue sample out of the tissue receiving area.

9 Claims, 39 Drawing Sheets

U.S. PATENT DOCUMENTS

| | | |
|---|---|---|
| Re. 34,056 | 9/1992 | Lindgren et al. . |
| 737,293 | 8/1903 | Summerfeldt . |
| 1,167,014 | 1/1916 | O'Brien . |
| 1,585,934 | 5/1926 | Muir . |
| 1,663,761 | 3/1928 | Johnson . |
| 1,867,624 | 7/1932 | Hoffman . |
| 2,505,358 | 4/1950 | Gusberg et al. . |
| 2,705,949 | 4/1955 | Silverman . |
| 2,729,210 | 1/1956 | Spencer . |
| 3,173,414 | 3/1965 | Guillant ................................... 128/2 |
| 3,400,708 | 9/1968 | Scheidt . |
| 3,477,423 | 11/1969 | Griffith . |
| 3,561,429 | 2/1971 | Jewett et al. . |
| 3,590,808 | 7/1971 | Muller . |
| 3,606,878 | 9/1971 | Kellogg, Jr. . |
| 3,732,858 | 5/1973 | Banko . |
| 3,734,099 | 5/1973 | Bender et al. . |
| 3,844,272 | 10/1974 | Banko . |
| 3,929,123 | 12/1975 | Jamshidi . |
| 3,989,033 | 11/1976 | Halpern . |
| 3,995,619 | 12/1976 | Glatzer . |
| 4,099,518 | 7/1978 | Baylis et al. . |
| 4,200,106 | 4/1980 | Douvas et al. . |
| 4,203,444 | 5/1980 | Bonnell et al. . |
| 4,210,146 | 7/1980 | Banko . |
| 4,220,155 | 9/1980 | Kimberling et al. . |
| 4,243,048 | 1/1981 | Griffin . |
| 4,246,902 | 1/1981 | Martinez . |
| 4,274,414 | 6/1981 | Johnson . |
| 4,282,884 | 8/1981 | Boebel . |
| 4,314,560 | 2/1982 | Helfgott et al. . |
| 4,340,066 | 7/1982 | Shah . |
| 4,396,021 | 8/1983 | Baumgartner . |
| 4,445,517 | 5/1984 | Feild ................................... 128/752 |
| 4,513,745 | 4/1985 | Amoils . |
| 4,530,356 | 7/1985 | Helfgott et al. . |
| 4,577,629 | 3/1986 | Martinez . |
| 4,589,414 | 5/1986 | Yoshida et al. . |
| 4,598,710 | 7/1986 | Kleinberg et al. . |
| 4,600,014 | 7/1986 | Beraha . |
| 4,603,694 | 8/1986 | Wheeler . |
| 4,643,196 | 2/1987 | Tanaka et al. . |
| 4,644,951 | 2/1987 | Bays . |
| 4,651,752 | 3/1987 | Fuerst . |
| 4,651,753 | 3/1987 | Lifton . |
| 4,660,267 | 4/1987 | Wheeler . |
| 4,662,869 | 5/1987 | Wright . |
| 4,667,684 | 5/1987 | Leigh . |
| 4,669,496 | 6/1987 | Kemp et al. . |
| 4,674,502 | 6/1987 | Imonti . |
| 4,678,459 | 7/1987 | Onik et al. . |
| 4,681,123 | 7/1987 | Valtchev . |
| 4,685,458 | 8/1987 | Leckrone . |
| 4,696,298 | 9/1987 | Higgins et al. . |
| 4,699,154 | 10/1987 | Lindgren . |
| 4,702,260 | 10/1987 | Wang . |
| 4,702,261 | 10/1987 | Cornell et al. . |
| 4,708,147 | 11/1987 | Haaga . |
| 4,711,250 | 12/1987 | Gilbaugh, Jr. et al. . |
| 4,733,662 | 3/1988 | DeStanick et al. . |
| 4,733,671 | 3/1988 | Mehl . |
| 4,735,215 | 4/1988 | Goto et al. . |
| 4,776,346 | 10/1988 | Beraha et al. . |
| 4,781,186 | 11/1988 | Simpson et al. . |
| 4,781,202 | 11/1988 | Janese . |
| 4,790,329 | 12/1988 | Simon ................................... 128/749 |
| 4,799,494 | 1/1989 | Wang . |
| 4,819,635 | 4/1989 | Shapiro . |
| 4,838,280 | 6/1989 | Haaga . |
| 4,844,088 | 7/1989 | Kambin . |
| 4,850,354 | 7/1989 | McGurk-Burleson et al. . |
| 4,873,991 | 10/1989 | Skinner . |
| 4,874,375 | 10/1989 | Ellison . |
| 4,881,551 | 11/1989 | Taylor . |
| 4,907,598 | 3/1990 | Bauer . |
| 4,907,599 | 3/1990 | Taylor . |
| 4,917,100 | 4/1990 | Nottke . |
| 4,924,878 | 5/1990 | Nottke . |
| 4,936,835 | 6/1990 | Haaga . |
| 4,940,061 | 7/1990 | Terwilliger et al. . |
| 4,944,308 | 7/1990 | Akerfeldt . |
| 4,950,265 | 8/1990 | Taylor . |
| 4,953,558 | 9/1990 | Akerfeldt . |
| 4,958,625 | 9/1990 | Bates et al. . |
| 4,976,269 | 12/1990 | Mehl . |
| 4,982,739 | 1/1991 | Hemstreet et al. . |
| 4,989,614 | 2/1991 | Dejter, Jr. et al. . |
| 4,991,592 | 2/1991 | Christ . |
| 5,000,745 | 3/1991 | Guest et al. . |
| 5,002,553 | 3/1991 | Shiber . |
| 5,005,585 | 4/1991 | Mazza . |
| 5,006,114 | 4/1991 | Rogers et al. . |
| 5,009,391 | 4/1991 | Steigerwald . |
| 5,009,659 | 4/1991 | Hamlin et al. . |
| 5,011,473 | 4/1991 | Gatturna . |
| 5,011,490 | 4/1991 | Fischell et al. . |
| 5,012,818 | 5/1991 | Joishy . |
| 5,014,717 | 5/1991 | Lohrmann . |
| 5,018,530 | 5/1991 | Rank et al. . |
| 5,019,036 | 5/1991 | Stahl . |
| 5,019,088 | 5/1991 | Farr . |
| 5,019,089 | 5/1991 | Farr . |
| 5,021,059 | 6/1991 | Kensey et al. . |
| 5,026,384 | 6/1991 | Farr et al. . |
| 5,027,827 | 7/1991 | Cody et al. . |
| 5,031,634 | 7/1991 | Simon . |
| 5,035,248 | 7/1991 | Zinnecker . |
| 5,036,860 | 8/1991 | Leigh et al. . |
| 5,040,715 | 8/1991 | Green et al. . |
| 5,041,129 | 8/1991 | Hayhurst et al. . |
| 5,047,008 | 9/1991 | de Juan, Jr. et al. . |
| 5,047,040 | 9/1991 | Simpson et al. . |
| 5,048,538 | 9/1991 | Terwilliger . |
| 5,053,014 | 10/1991 | Van Heugen . |
| 5,053,044 | 10/1991 | Mueller et al. . |
| 5,056,529 | 10/1991 | De Groot . |
| 5,057,082 | 10/1991 | Burchette, Jr. . |
| 5,057,085 | 10/1991 | Kopans . |
| 5,059,197 | 10/1991 | Urie et al. . |
| 5,060,658 | 10/1991 | Dejter, Jr. et al. . |
| 5,061,281 | 10/1991 | Mares et al. . |
| 5,074,311 | 12/1991 | Hasson . |
| 5,074,841 | 12/1991 | Ademovic et al. . |
| 5,074,871 | 12/1991 | Groshong . |
| 5,078,142 | 1/1992 | Siczek et al. . |
| 5,078,723 | 1/1992 | Dance et al. . |
| 5,080,655 | 1/1992 | Haaga . |
| 5,085,659 | 2/1992 | Rydell . |
| 5,087,265 | 2/1992 | Summers . |
| 5,090,419 | 2/1992 | Palestrant . |
| 5,092,873 | 3/1992 | Simpson et al. . |
| 5,100,426 | 3/1992 | Nixon . |
| 5,106,364 | 4/1992 | Hayafuji et al. . |
| 5,121,751 | 6/1992 | Panalletta . |
| 5,125,413 | 6/1992 | Baran . |
| 5,127,419 | 7/1992 | Kaldany . |
| 5,135,481 | 8/1992 | Nemeh . |
| 5,146,921 | 9/1992 | Terwilliger et al. . |
| 5,152,744 | 10/1992 | Krause et al. . |
| 5,156,160 | 10/1992 | Bennett . |
| 5,161,542 | 11/1992 | Palestrant . |
| 5,178,625 | 1/1993 | Groshong . |

| | | |
|---|---|---|
| 5,183,052 | 2/1993 | Terwilliger et al. |
| 5,183,054 | 2/1993 | Burkholder et al. |
| 5,188,118 | 2/1993 | Terwilliger |
| 5,192,291 | 3/1993 | Pannek, Jr. |
| 5,195,533 | 3/1993 | Chin et al. |
| 5,195,988 | 3/1993 | Haaga |
| 5,197,484 | 3/1993 | Kornberg et al. |
| 5,199,441 | 4/1993 | Hogle |
| 5,211,651 | 5/1993 | Reger et al. |
| 5,213,110 | 5/1993 | Kedem et al. |
| 5,217,458 | 6/1993 | Parins |
| 5,217,479 | 6/1993 | Shuler |
| 5,220,926 | 6/1993 | Jones |
| 5,222,966 | 6/1993 | Perkins et al. |
| 5,224,470 | 7/1993 | Schnepp-Pesch et al. |
| 5,224,488 | 7/1993 | Neuffer |
| 5,224,945 | 7/1993 | Pannek, Jr. |
| 5,226,909 | 7/1993 | Evans et al. |
| 5,226,910 | 7/1993 | Kajiyama et al. |
| 5,234,994 | 8/1993 | Ranalletta |
| 5,236,334 | 8/1993 | Bennett |
| 5,242,460 | 9/1993 | Klein et al. |
| 5,243,994 | 9/1993 | Ranalletta |
| 5,249,582 | 10/1993 | Taylor |
| 5,249,583 | 10/1993 | Mallaby |
| 5,250,059 | 10/1993 | Andreas et al. |
| 5,250,065 | 10/1993 | Clement et al. |
| 5,251,641 | 10/1993 | Xavier |
| 5,254,105 | 10/1993 | Haaga |
| 5,269,793 | 12/1993 | Simpson |
| 5,269,797 | 12/1993 | Bonati et al. |
| 5,269,798 | 12/1993 | Winkler |
| 5,273,051 | 12/1993 | Wilk |
| 5,273,519 | 12/1993 | Koros et al. |
| 5,275,609 | 1/1994 | Pingleton et al. |
| 5,282,476 | 2/1994 | Terwilliger |
| 5,282,484 | 2/1994 | Reger |
| 5,284,156 | 2/1994 | Schramm et al. |
| 5,285,795 | 2/1994 | Ryan et al. |
| 5,286,253 | 2/1994 | Fucci |
| 5,290,303 | 3/1994 | Pingleton et al. |
| 5,292,310 | 3/1994 | Yoon |
| 5,301,684 | 4/1994 | Ogirala |
| 5,306,260 | 4/1994 | Kanner |
| 5,312,425 | 5/1994 | Evans et al. |
| 5,313,958 | 5/1994 | Bauer |
| 5,316,013 | 5/1994 | Striebel, II et al. |
| 5,320,110 | 6/1994 | Wang |
| 5,335,671 | 8/1994 | Clement |
| 5,335,672 | 8/1994 | Bennett |
| 5,336,176 | 8/1994 | Yoon |
| 5,353,804 | 10/1994 | Kornberg et al. |
| 5,366,463 | 11/1994 | Ryan |
| 5,366,464 | 11/1994 | Belknap |
| 5,366,468 | 11/1994 | Fucci et al. |
| 5,368,045 | 11/1994 | Clement et al. |
| 5,392,790 | 2/1995 | Kanner et al. |
| 5,394,887 | 3/1995 | Haaga |
| 5,403,334 | 4/1995 | Evans et al. |
| 5,405,321 | 4/1995 | Reeves .................................... 604/44 |
| 5,409,013 | 4/1995 | Clement |
| 5,415,182 | 5/1995 | Chin et al. |
| 5,417,703 | 5/1995 | Brown et al. |
| 5,419,774 | 5/1995 | Willard et al. |
| 5,425,376 | 6/1995 | Banys et al. |
| 5,433,739 | 7/1995 | Sluiyter .................................... 607/99 |
| 5,437,630 | 8/1995 | Daniel et al. |
| 5,439,474 | 8/1995 | Li |
| 5,449,001 | 9/1995 | Terwilliger |
| 5,456,689 | 10/1995 | Kresch et al. |
| 5,458,112 | 10/1995 | Weaver |
| 5,476,101 | 12/1995 | Schramm et al. |
| 5,477,862 | 12/1995 | Haaga |
| 5,492,130 | 2/1996 | Chiou |
| 5,501,464 | 3/1996 | Kaldany |
| 5,505,210 | 4/1996 | Clement |
| 5,505,211 | 4/1996 | Ohto et al. |
| 5,507,298 | 4/1996 | Schramm et al. |
| 5,511,556 | 4/1996 | DeSantis |
| 5,526,822 | 6/1996 | Burbank et al. |
| 5,535,755 | 7/1996 | Heske |
| 5,538,010 | 7/1996 | Darr et al. |
| 5,546,957 | 8/1996 | Heske |
| 5,551,442 | 9/1996 | Kanner et al. |
| 5,560,373 | 10/1996 | De Santis |
| 5,562,613 | 10/1996 | Kaldany |
| 5,564,436 | 10/1996 | Hakky et al. |
| 5,570,699 | 11/1996 | Kass |
| 5,595,185 | 1/1997 | Erlich |
| 5,617,874 | 4/1997 | Baran |
| 5,649,547 | 7/1997 | Richart et al. |
| 5,655,542 | 8/1997 | Weilandt |
| 5,752,923 | 5/1998 | Terwilliger |
| 5,769,086 | 6/1998 | Ritchart et al. |
| 5,775,333 | 7/1998 | Burbank et al. |
| 5,779,647 | 7/1998 | Chau et al. |
| 5,810,744 | 9/1998 | Chue et al. |
| 5,928,164 | 7/1999 | Burbank et al. |
| 5,989,196 | 11/1999 | Chu et al. |

FOREIGN PATENT DOCUMENTS

| | | |
|---|---|---|
| 0105309 | 3/1983 | European Pat. Off. |
| 0 207 726 A2 | 1/1987 | European Pat. Off. |
| 0 238 461 A1 | 9/1987 | European Pat. Off. |
| 0 378 692 | 7/1990 | European Pat. Off. |
| 0221007 | 12/1990 | European Pat. Off. |
| 0 442 851 A1 | 8/1991 | European Pat. Off. |
| 053688 A1 | 8/1992 | European Pat. Off. |
| 0536888 | 8/1992 | European Pat. Off. |
| 0 536 888 A1 | 4/1993 | European Pat. Off. |
| 0 561 732 A1 | 9/1993 | European Pat. Off. |
| 1 161 400 | 8/1958 | France |
| 1 267 960 | 6/1960 | France |
| 2 332 743 | 6/1977 | France |
| 2 654 609 | 5/1991 | France |
| 935625 | 11/1955 | Germany |
| 1 817 555 | 1/1971 | Germany |
| 27 19 959 A1 | 11/1978 | Germany |
| 159 394 | 3/1983 | Germany |
| 88 02 580 | 9/1988 | Germany |
| 42 16 694 A1 | 12/1992 | Germany |
| 249551 | 5/1970 | Russian Federation |
| 483978 | 12/1975 | Russian Federation |
| 1537233 | 6/1987 | Russian Federation |
| 1614800 | 4/1988 | Russian Federation |
| 1641297 | 11/1988 | Russian Federation |
| 1456115 | 5/1989 | Russian Federation |
| 2033758 | 5/1993 | Russian Federation |
| 400319 | 2/1974 | U.S.S.R. |
| 520 976 | 7/1976 | U.S.S.R. |
| 648 219 | 2/1979 | U.S.S.R. |
| 707 576 | 1/1980 | U.S.S.R. |
| 0728 852 | 5/1980 | U.S.S.R. |
| 1178 422 | 9/1985 | U.S.S.R. |
| 1192 795 | 11/1985 | U.S.S.R. |
| 1 255 330 | 12/1971 | United Kingdom |
| 1 393 068 | 5/1975 | United Kingdom |
| 2 237 992 | 5/1991 | United Kingdom |
| 91/01112 | 2/1991 | WIPO |
| WO 92/00040 | 1/1992 | WIPO |
| 92/19159 | 11/1992 | WIPO |
| WO 93/12707 | 7/1993 | WIPO |
| WO 93/14707 | 8/1993 | WIPO |
| 83/03343 | 10/1993 | WIPO |

| | | |
|---|---|---|
| WO 93/20753 | 10/1993 | WIPO . |
| WO 94/08512 | 4/1994 | WIPO . |
| WO 94/26172 | 11/1994 | WIPO . |
| 88/07839 | 10/1998 | WIPO . |

OTHER PUBLICATIONS

Stereotaxic Needle Core Biopsy of Breast Lesions using a Regular Mammographic Table with an Adaptable Stereotaxic Device, Caines et al., pp. 317–321, Aug. 1993.

"ASAP Automatic Soft Tissue Biopsy System", Operational Guidelines, Microvasive Boston Scientific Corp. (2 Pgs.).

"When It Comes to Core Samples, I Demand Accuracy and Consistency for All My Patients", The Bard Biopty Biopsy System, Bard Radiology, (4 pages).

"Nucleotome System, Automated Percutaneous Lumbar Discectomy", Surgical Dynamics, (3 pages).

"Introducing the Singular Technology for Multi–Core Microcalcification Sampling", Biopsys Medical, Inc. (2 Pages).

"Mammotome Multi–Probe, Probe and Motorized Driver, Instructions for Use", Biopsys Medical, Inc. (3 pages).

Stereotaxic Needle Core Biopsy of Breast Lesions Using a Regular Mammographic Table with an Adaptable Stereotaxic Device, Caines et al., pp. 317–321, Aug. 1993.

Stereotactic Breast Biopsy with a Biopsy Gun, Parker, MD et al., pp. 741–747, Sep. 1990.

Stereotactic Percutaneous Breast Core Biopsy Technical Adaptaton and Initial Experience, Lovin, MD et al. pp. 135–143, 1990

Selective Use of Image–Guided Large–Core Needle Biopsy of the Breast: Accuracy and Cost–Effectiveness, Doyle et al., pp. 281–284, Aug. 1995.

Breast Biopsy: A Comparative Study of Stereotaxically Guided Core and Excisional Techniques, Gisvold et al., pp. 815–820, Apr. 1994.

Stereotactic Core Needle Biopsy of Mammographic Breast Lesions as a Viable Alternative to Surgical Biopsy, Mikahil, MD et al., pp. 363–367, 1994.

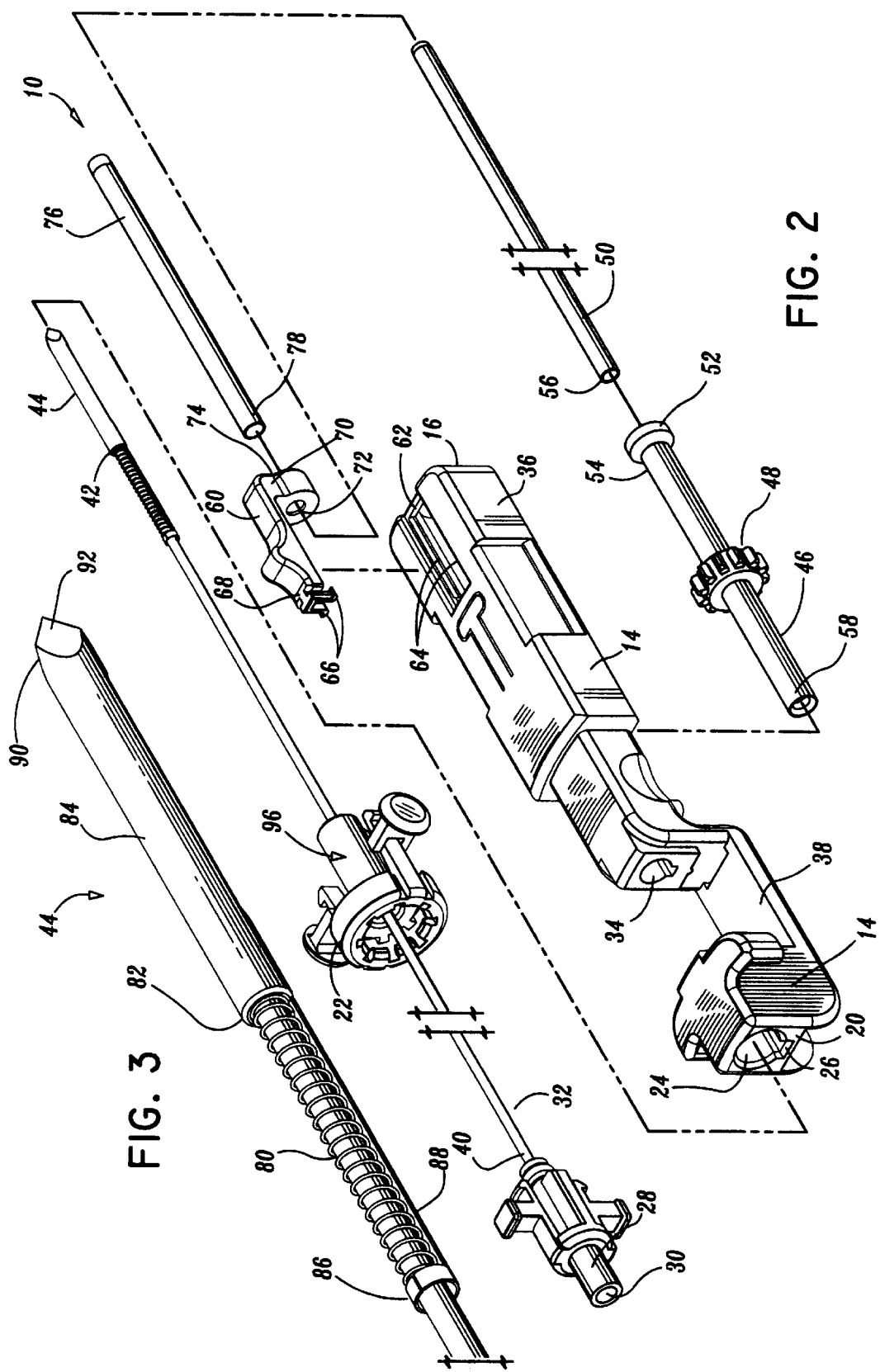

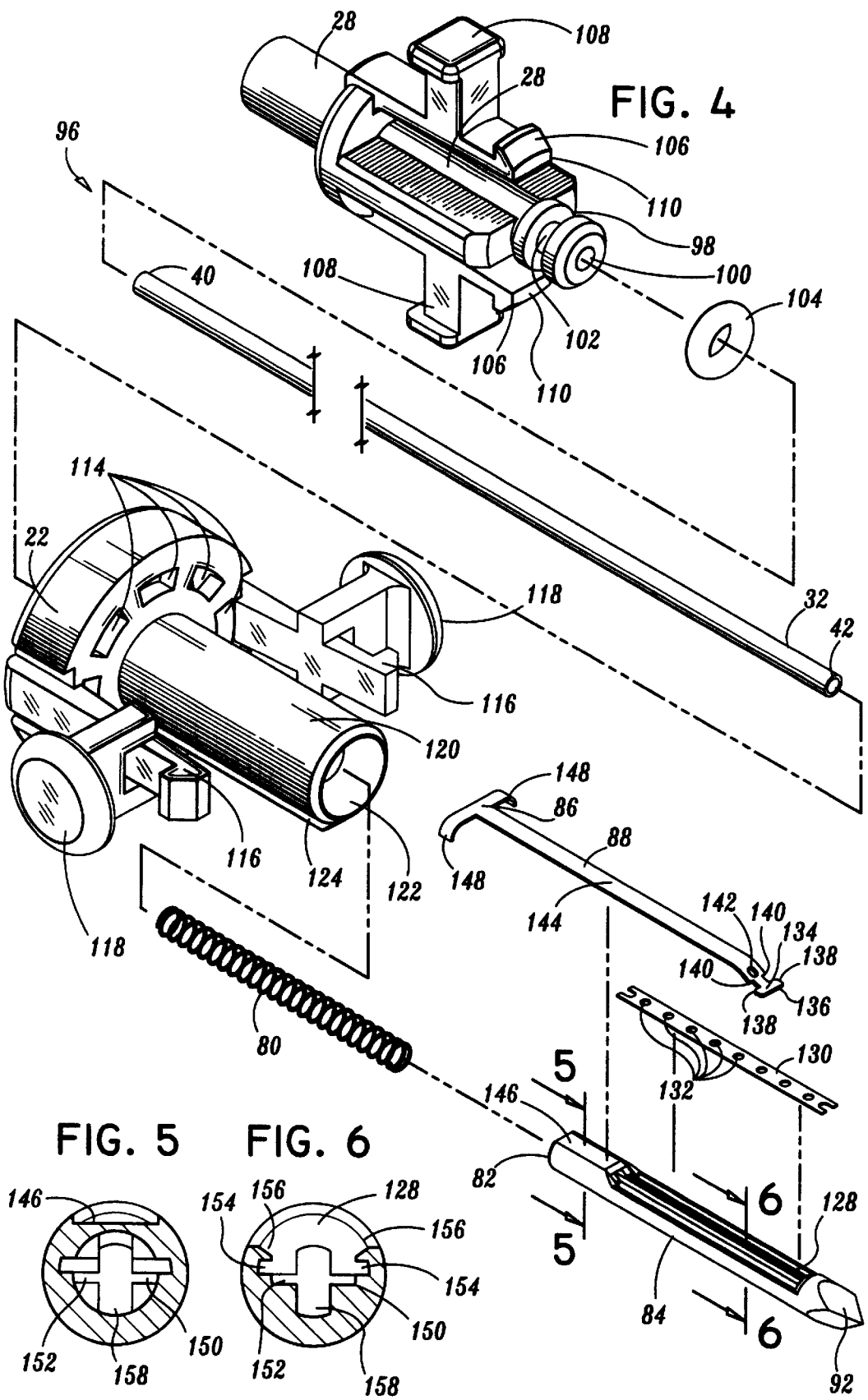

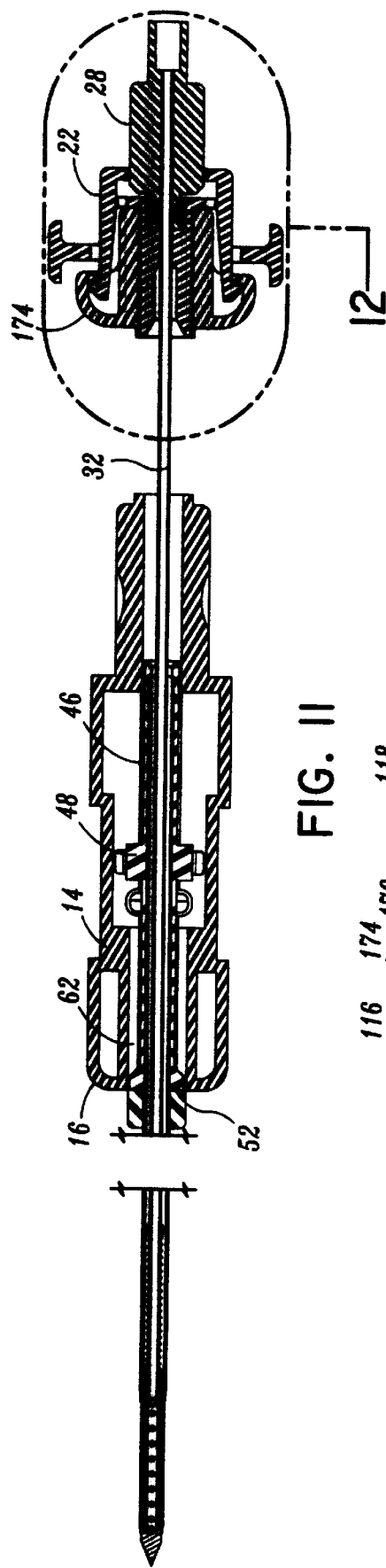

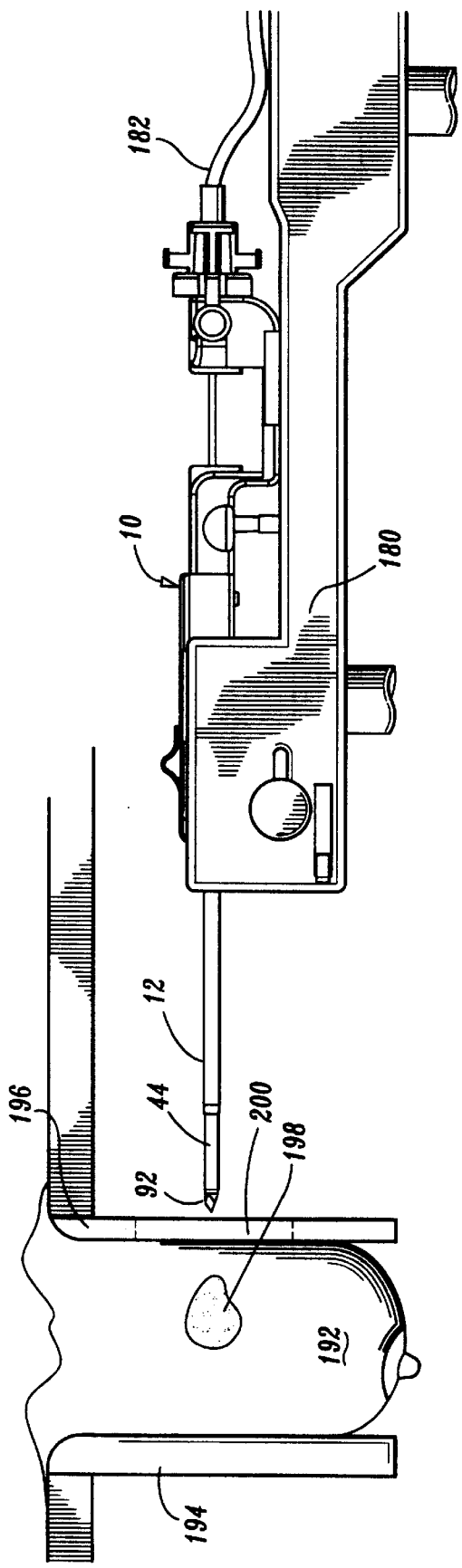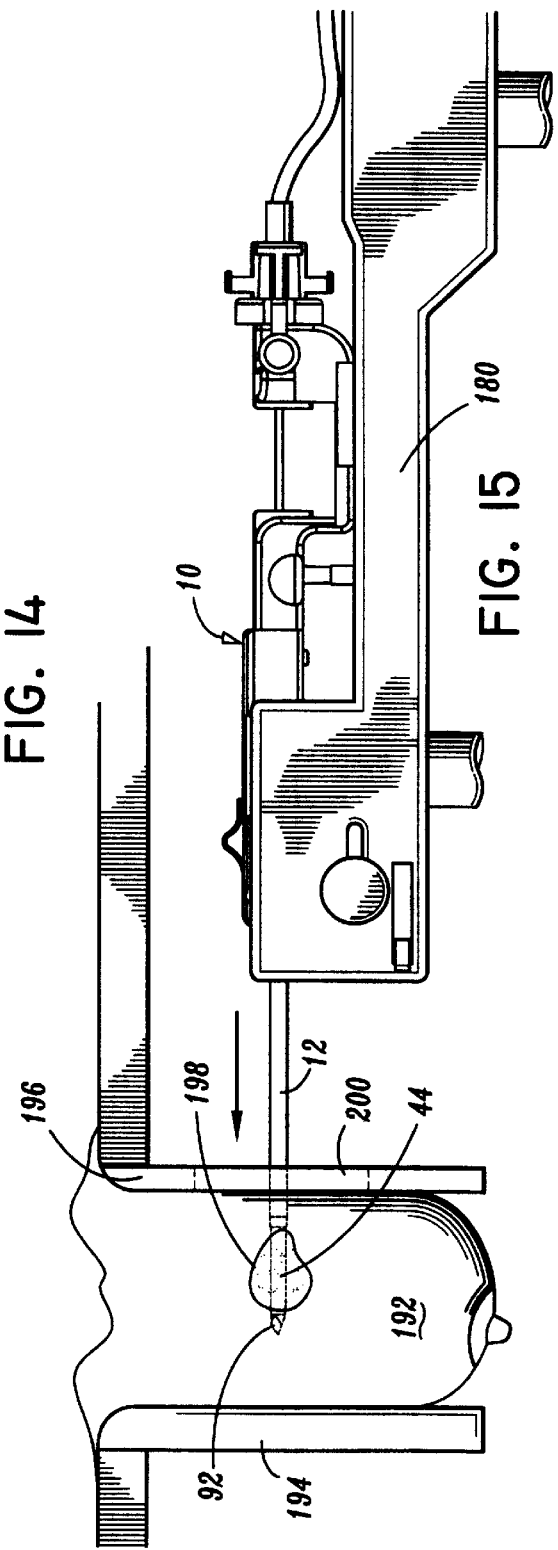

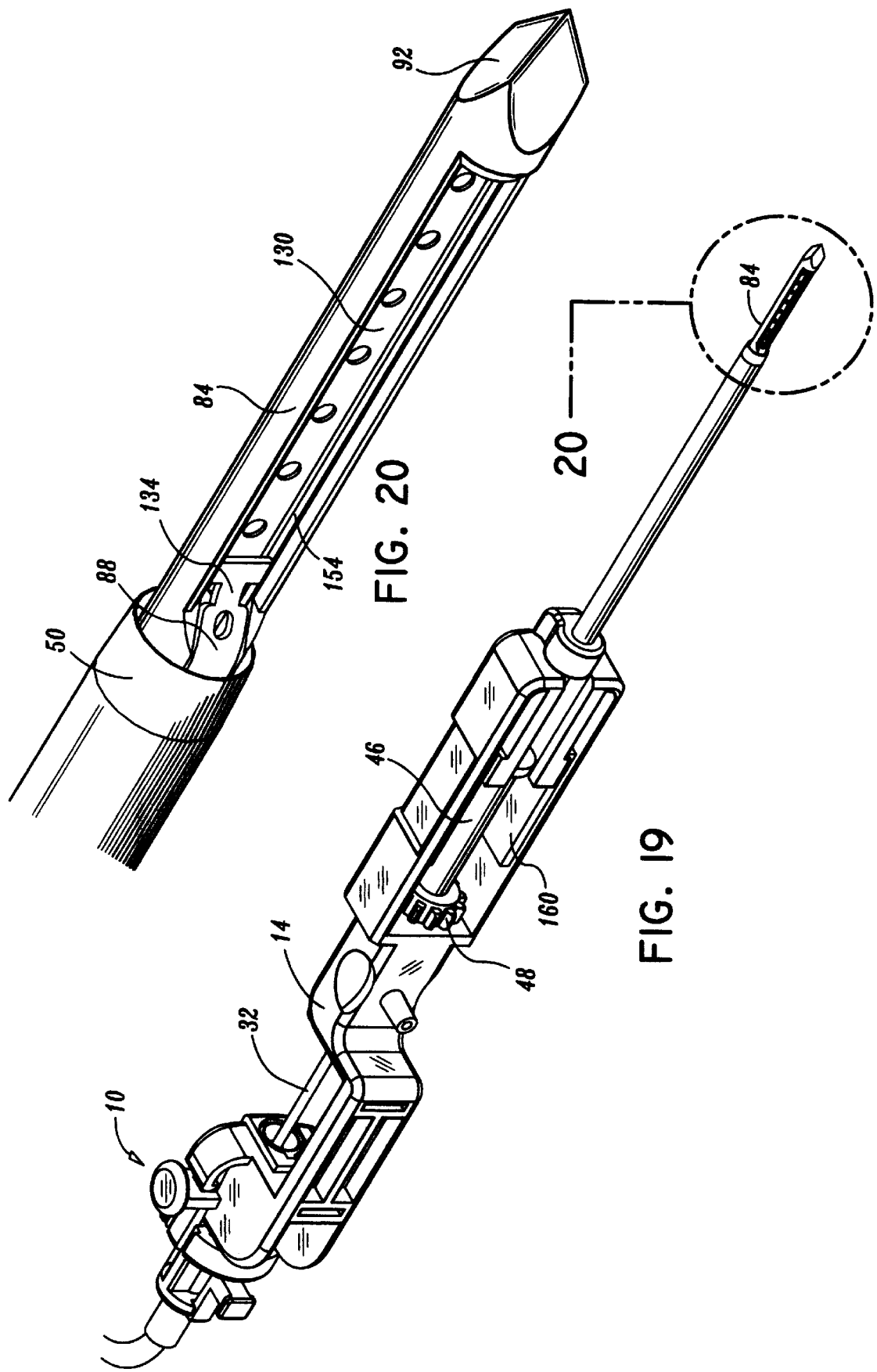

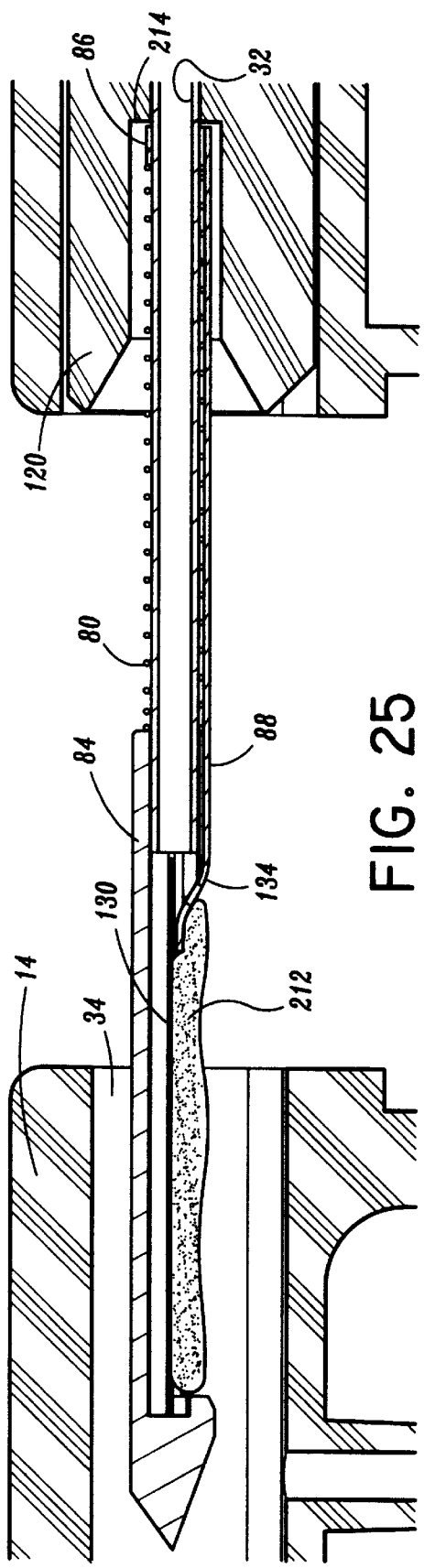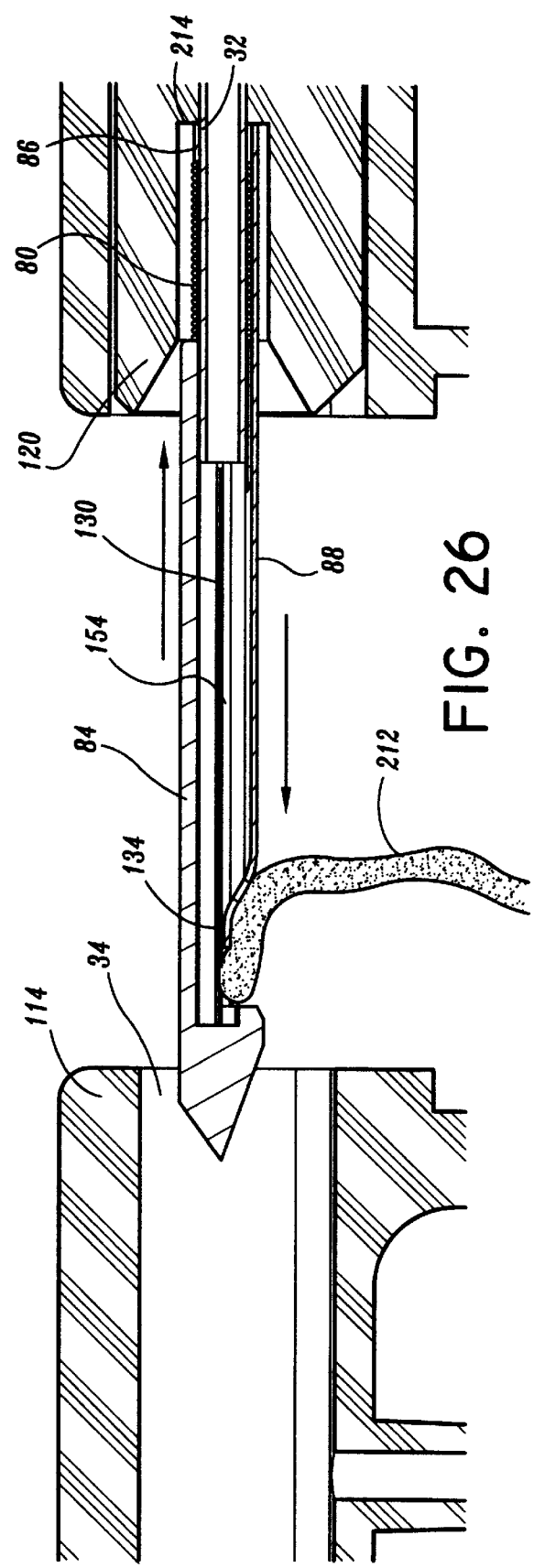

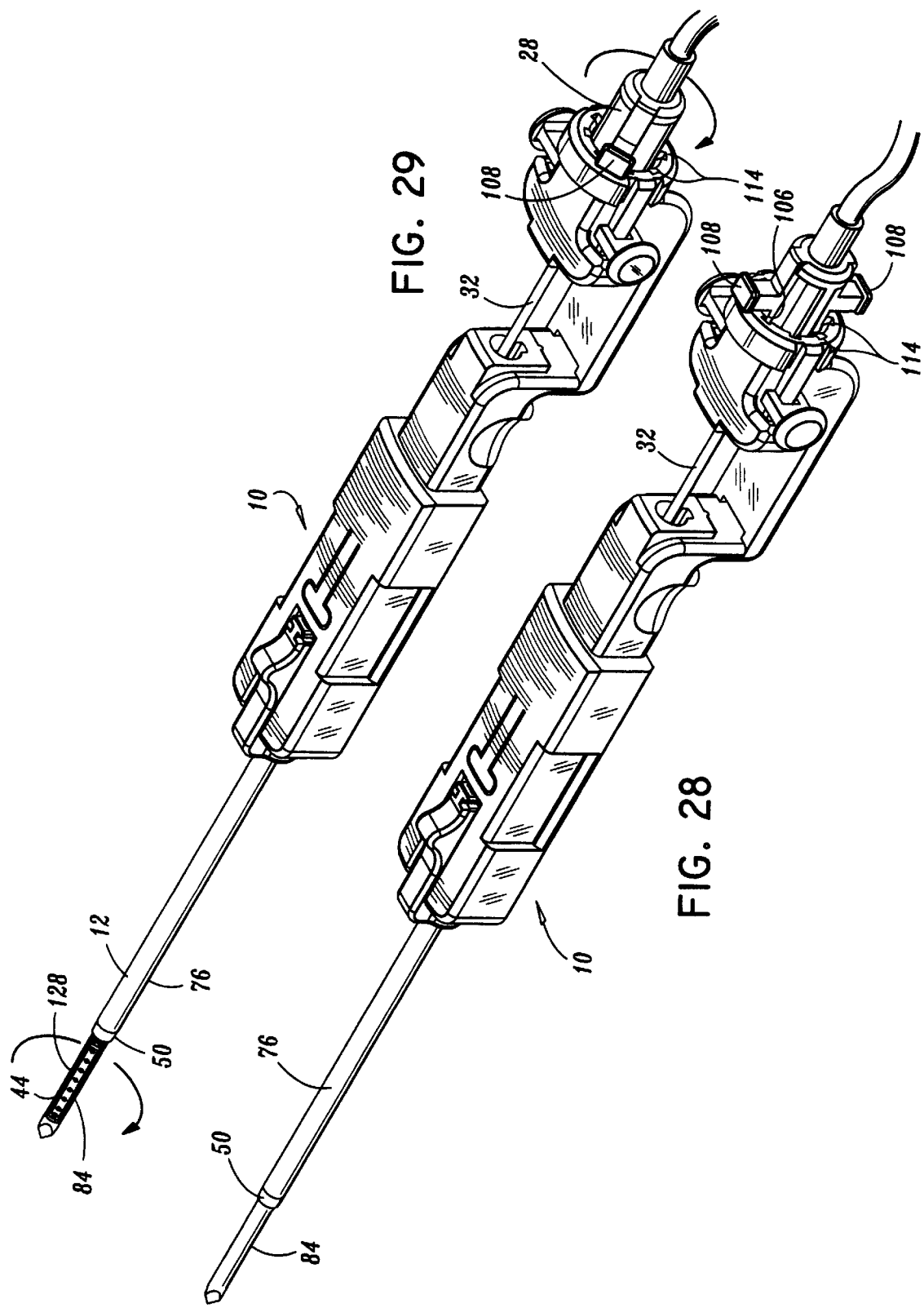

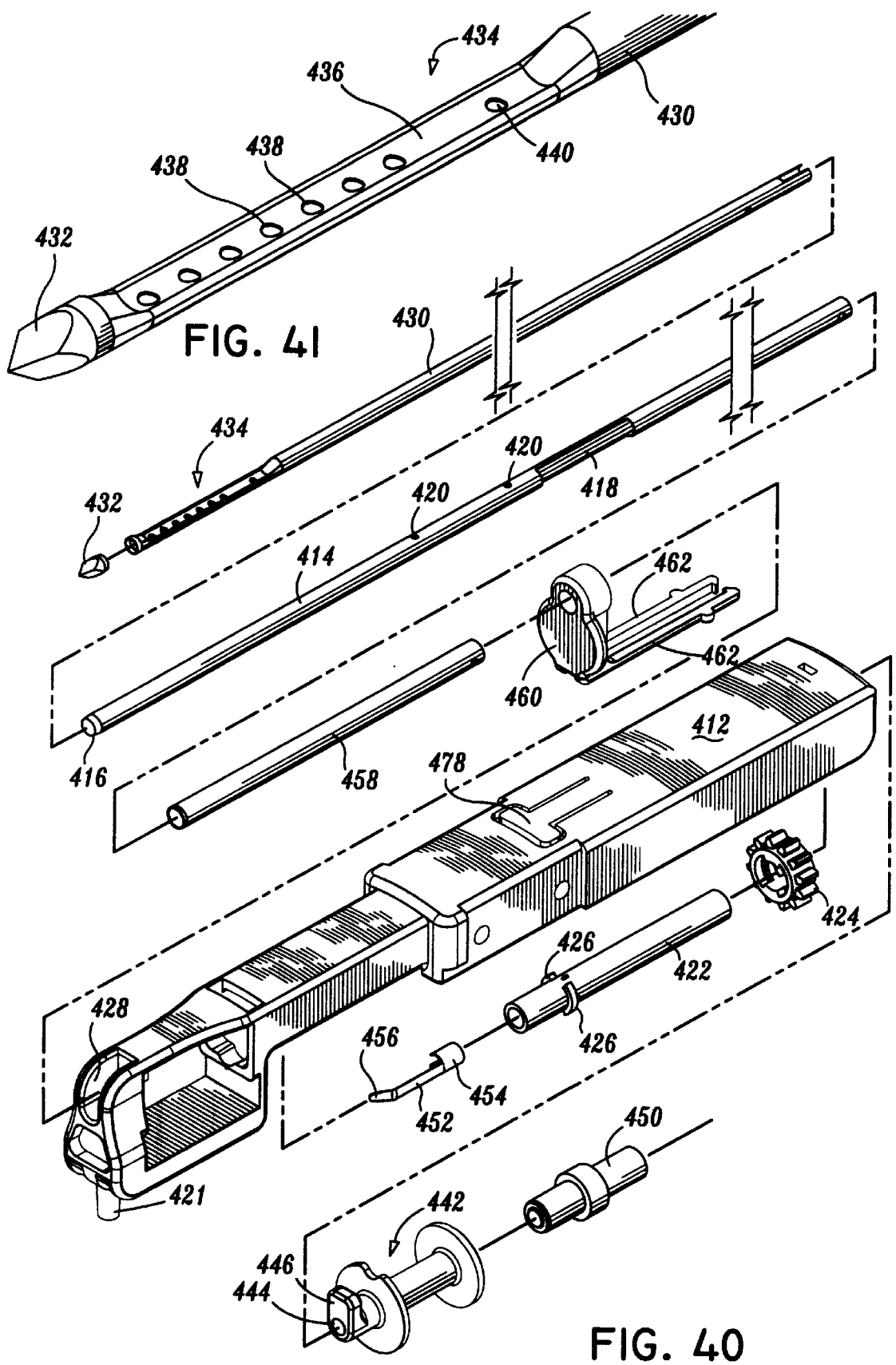

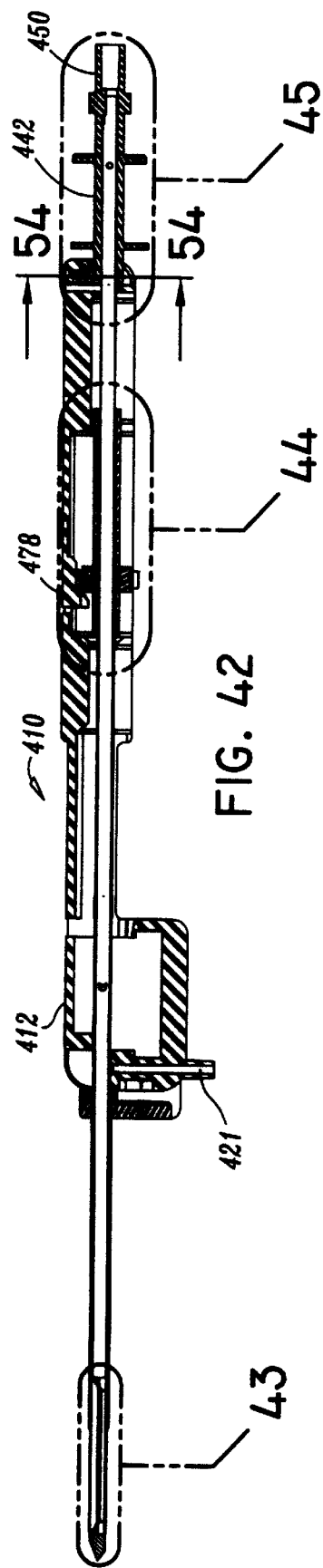
FIG. 42
FIG. 45
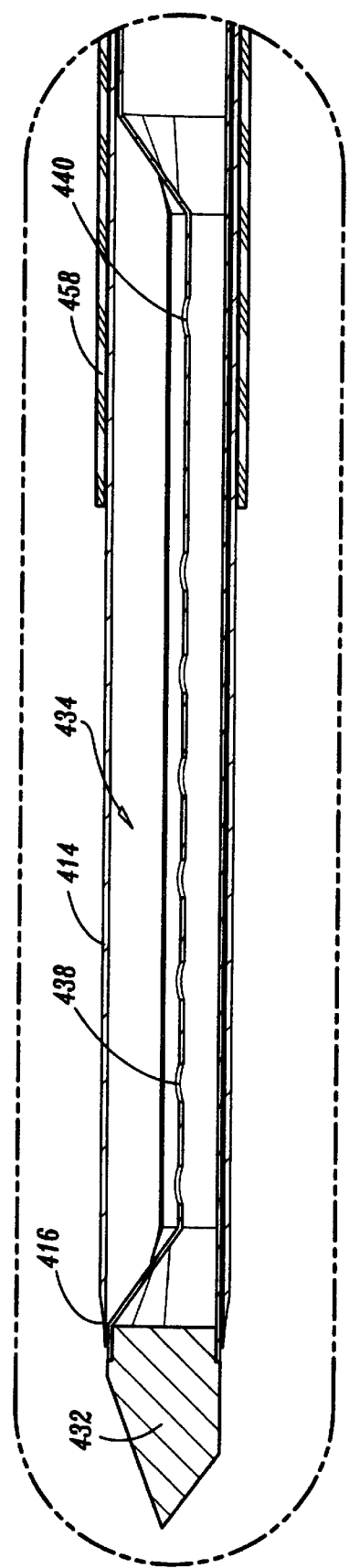
FIG. 43

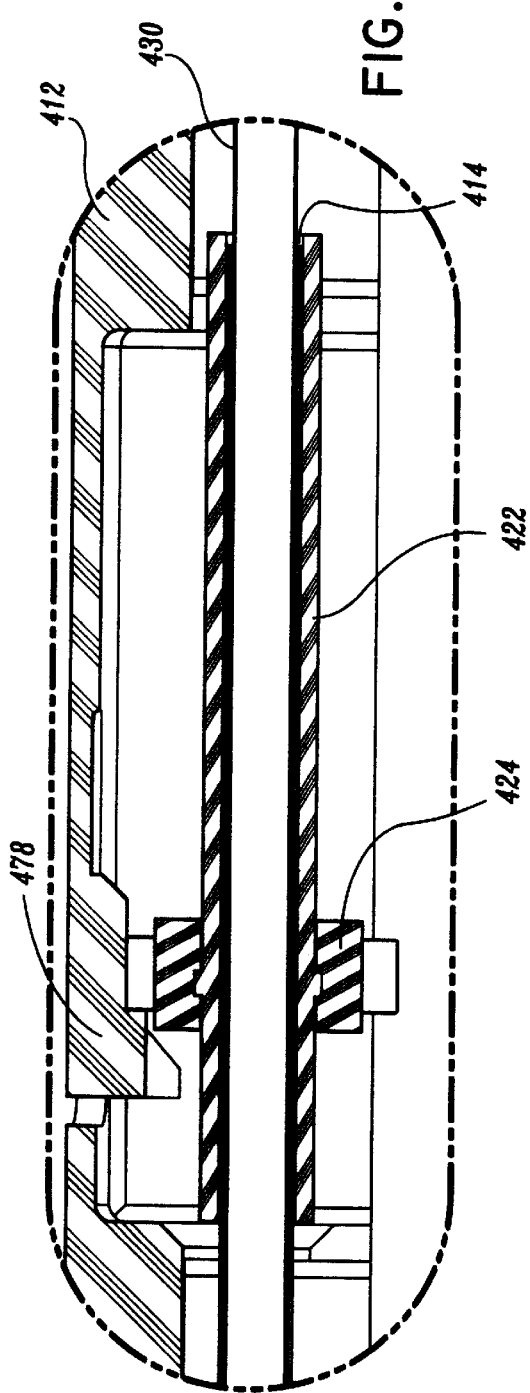
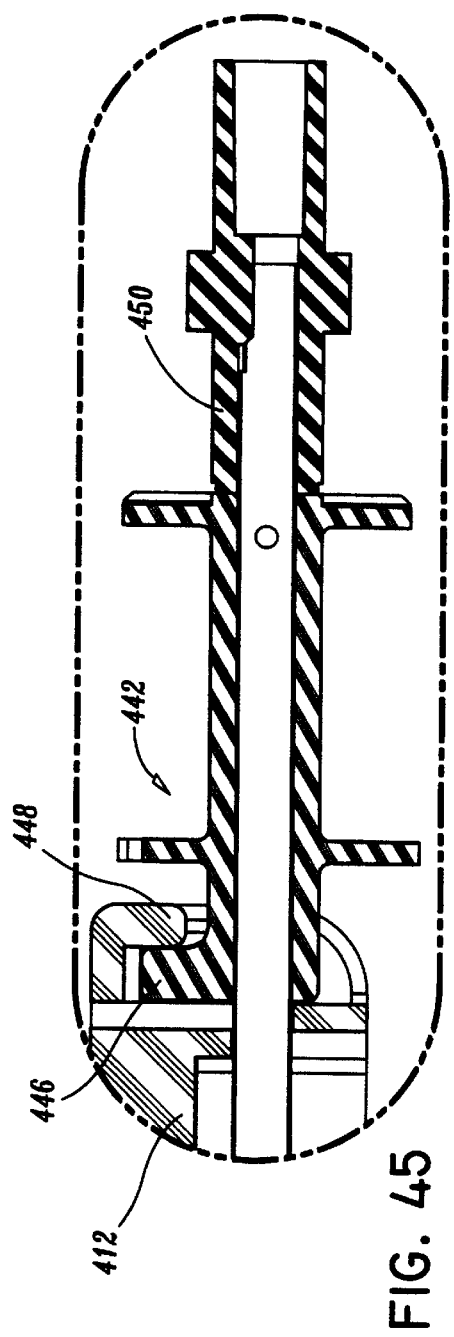
FIG. 44
FIG. 45

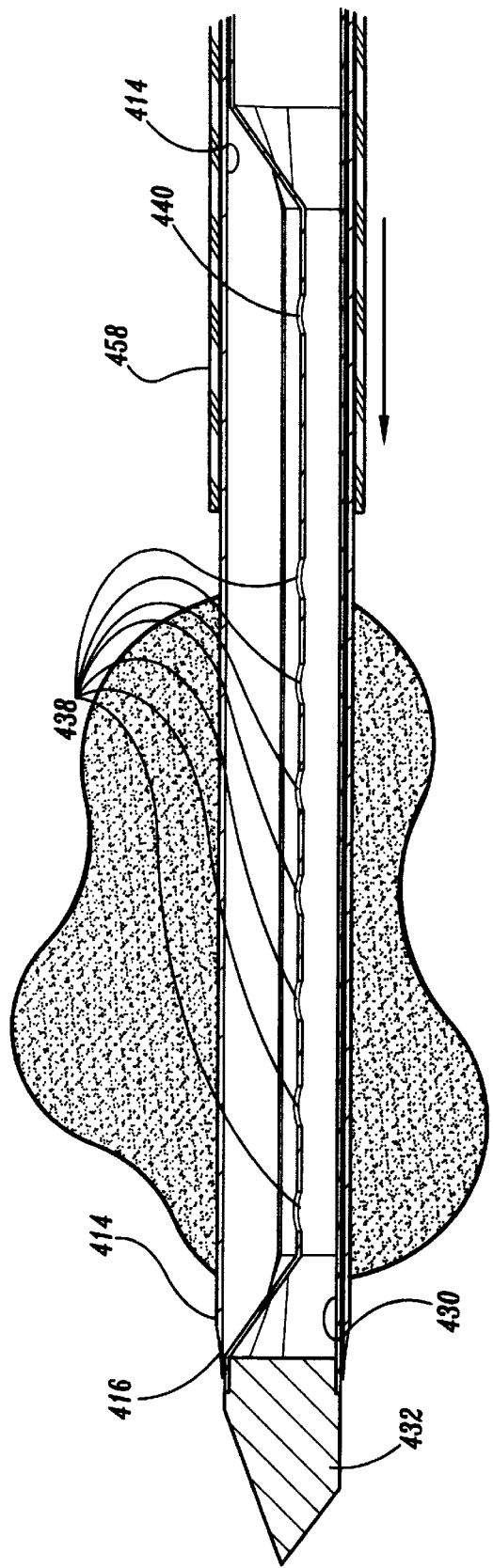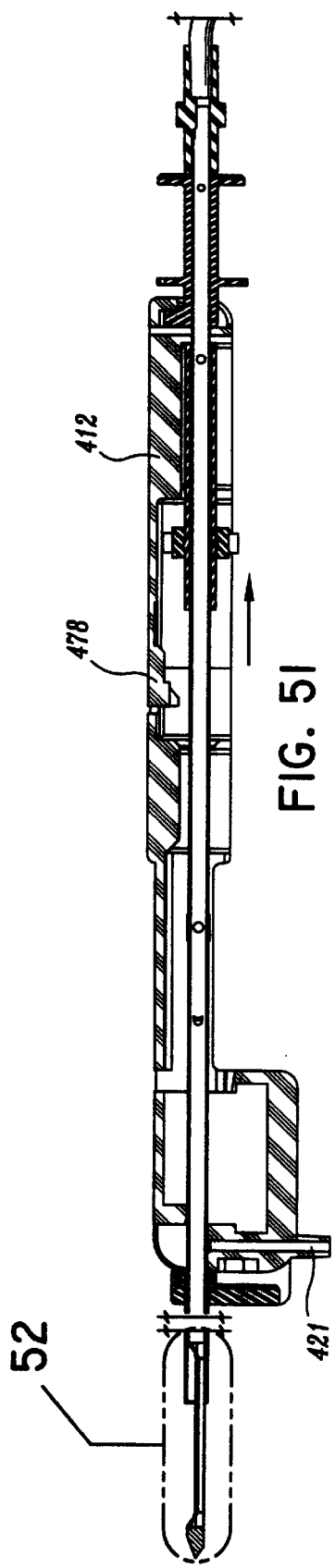

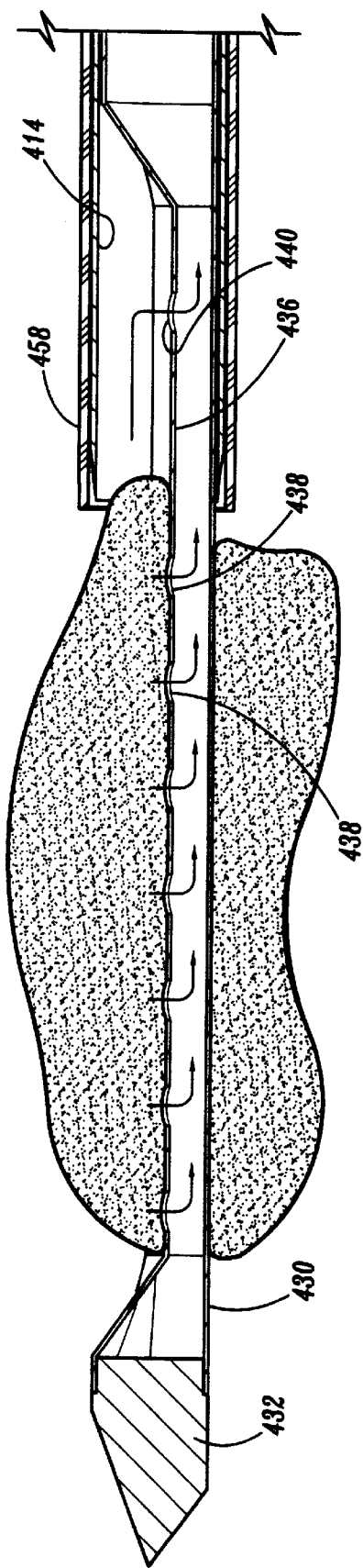
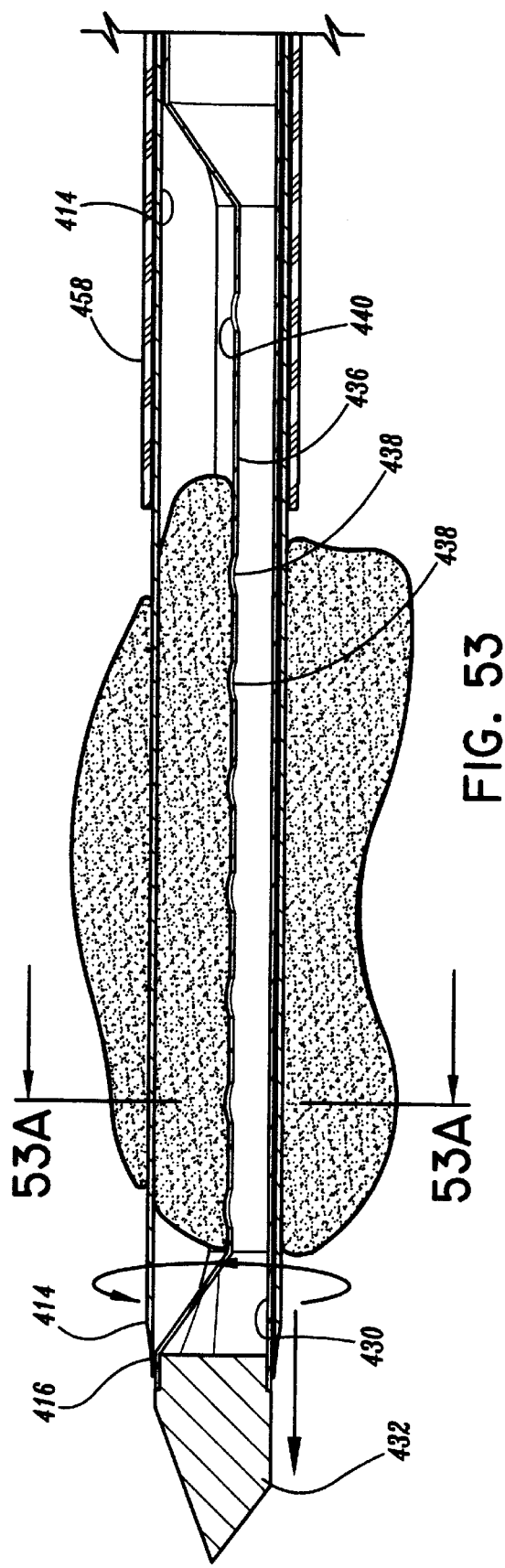
FIG. 52
FIG. 53

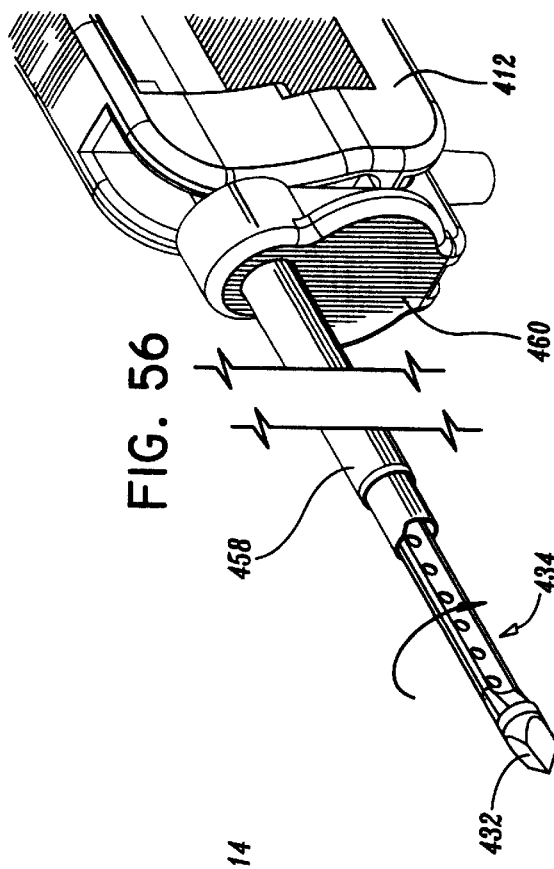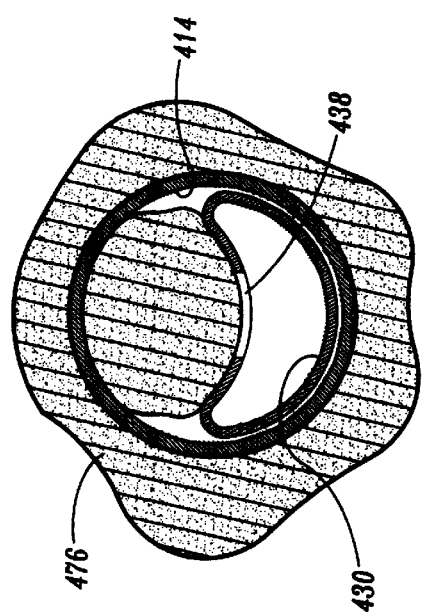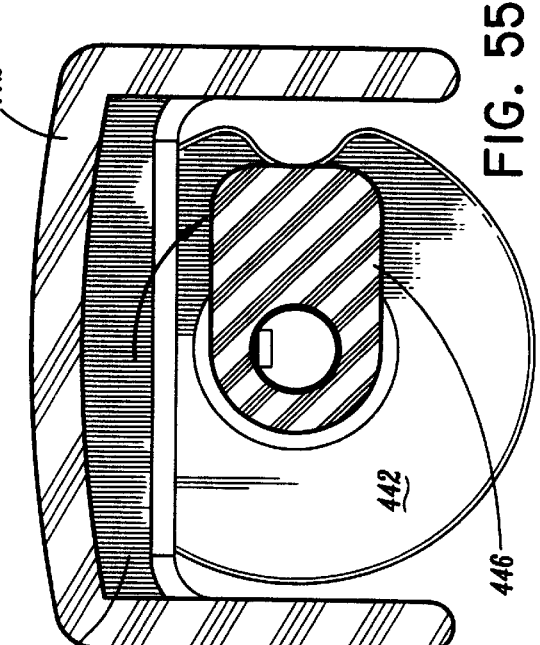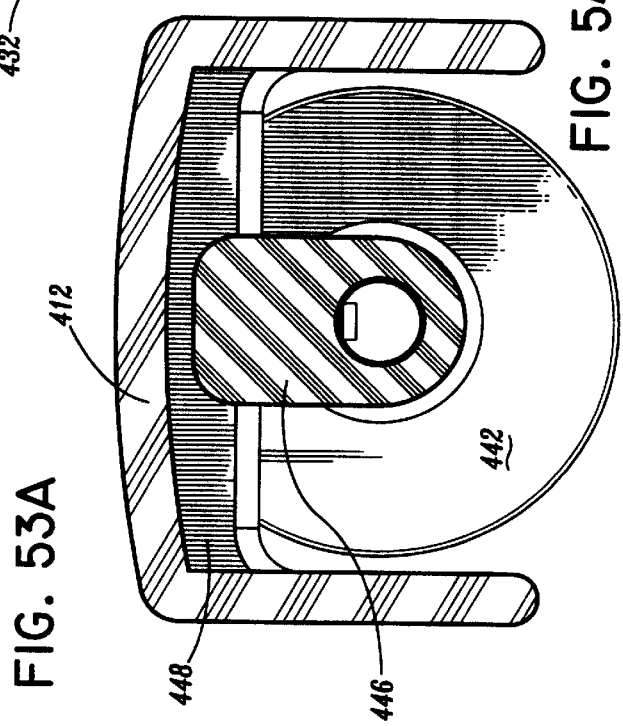

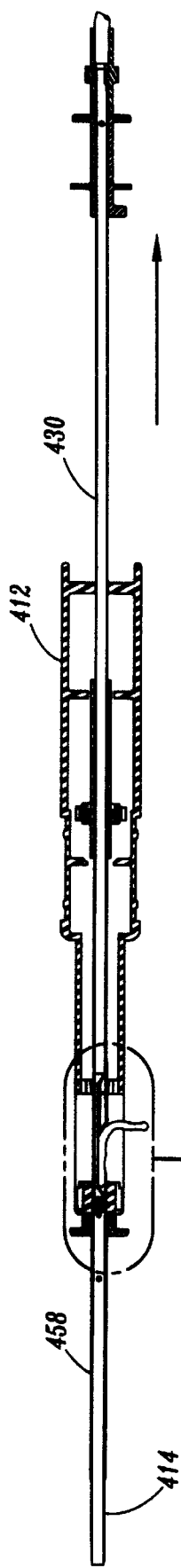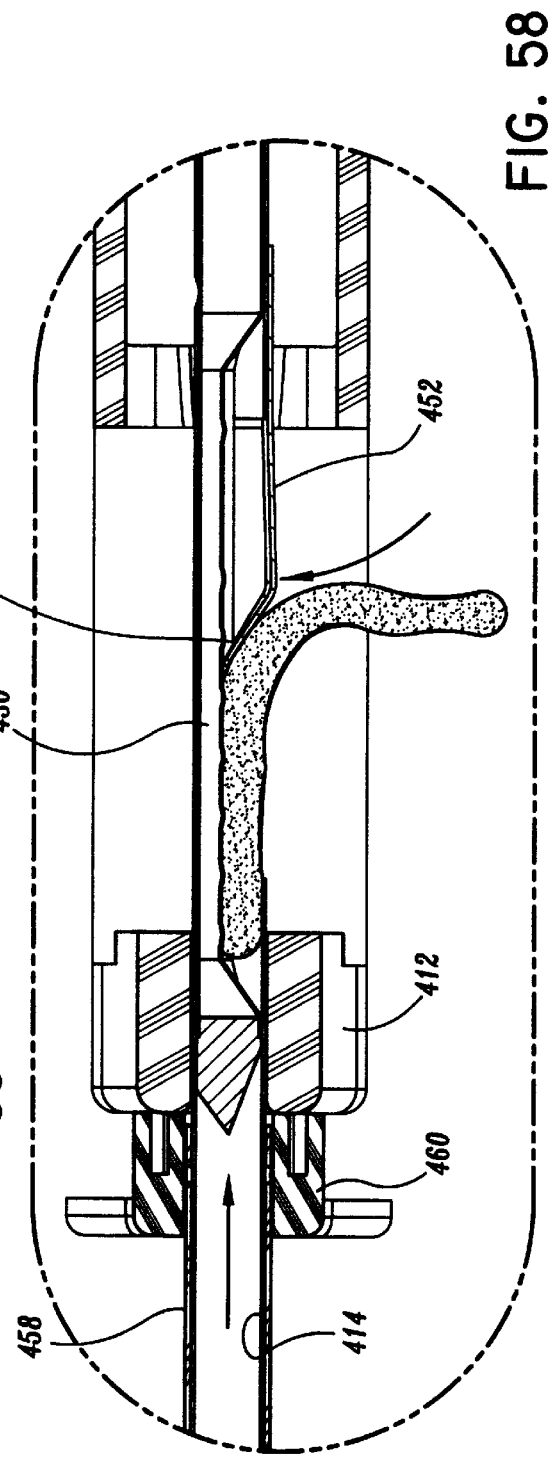
FIG. 57
FIG. 58

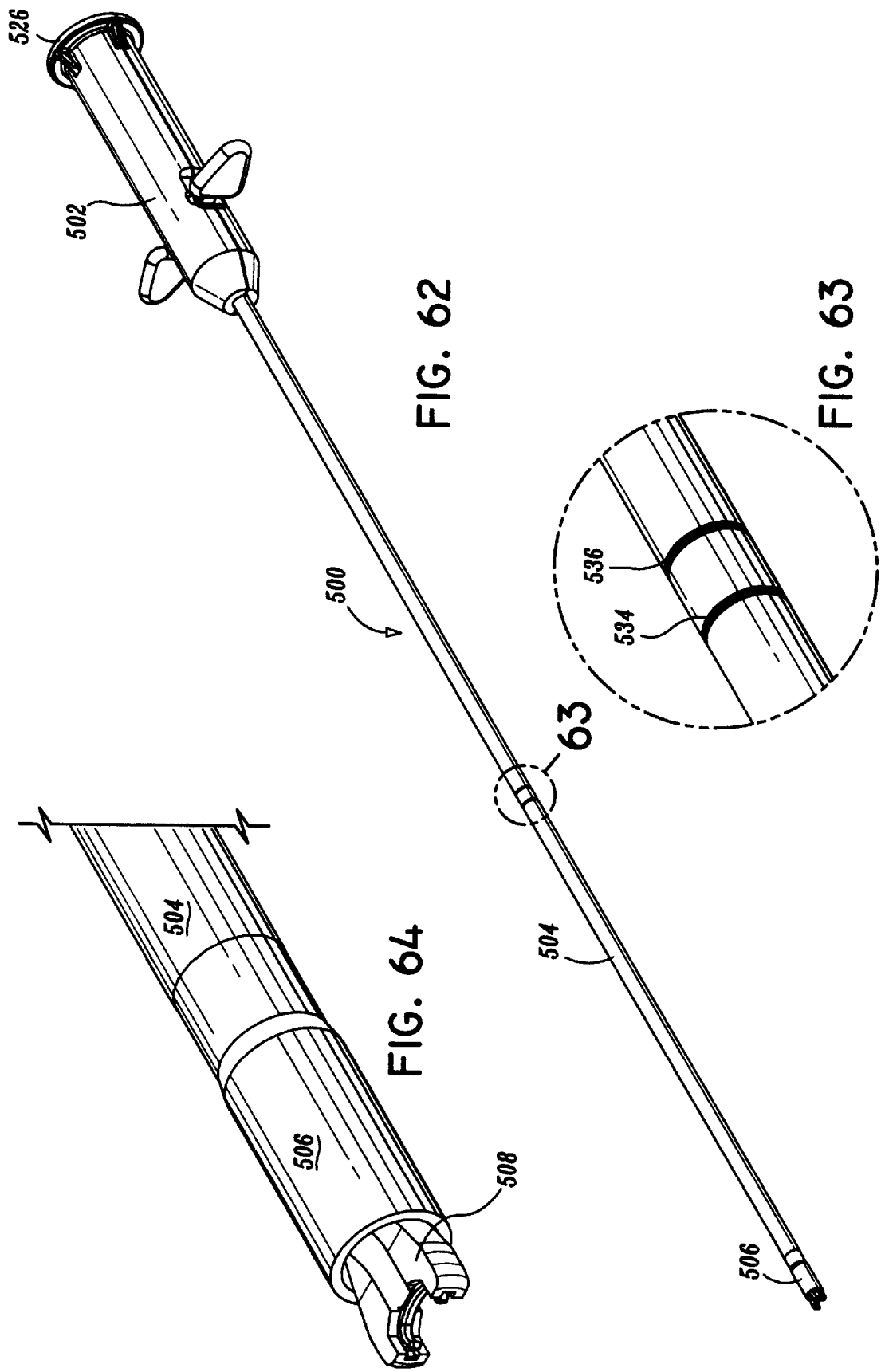

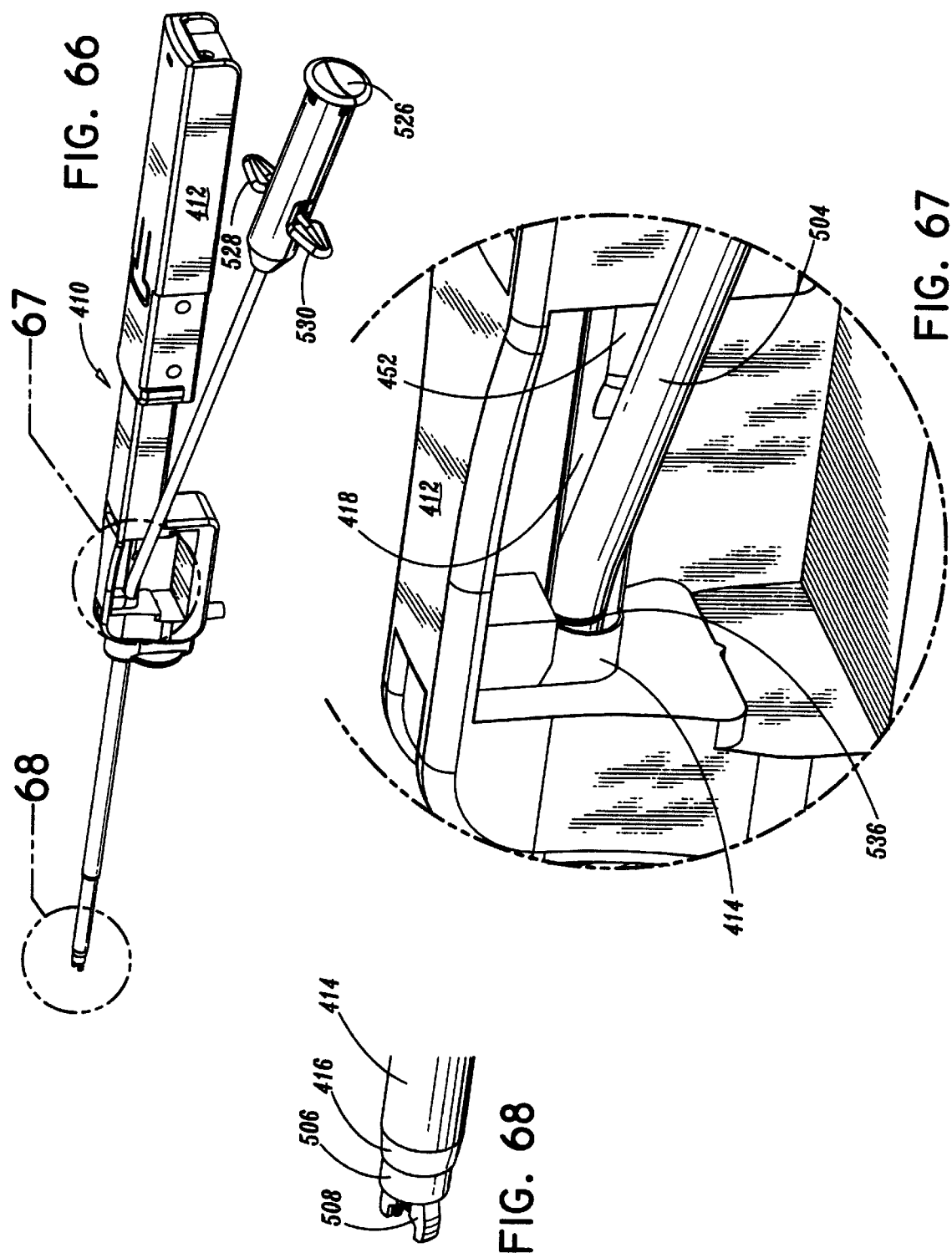

BIOPSY APPARATUS AND METHOD

CROSS REFERENCE TO RELATED APPLICATIONS

This application claims priority to U.S. Provisional Application Ser. No. 60/059,548 filed Sep. 19, 1997 by Farascioni et al., and to U.S. Provisional Application Ser. No. 60/059,545 filed Sep. 19, 1997 by Matula, the entire contents of each of these applications are hereby incorporated by reference.

TECHNICAL FIELD

This disclosure relates to an apparatus and method for the biopsy of tissue specimens and, more particularly, to a single insertion, multiple sample percutaneous biopsy apparatus and method.

BACKGROUND OF RELATED ART

It is often necessary to sample tissue in order to diagnose and treat patients suspected of having cancerous tumors, pre-malignant conditions and other diseases or disorders. Typically, in the case of suspected cancerous tissue, when the physician establishes by means of procedures such as palpation, x-ray or ultrasound imaging that suspicious conditions exist, a biopsy is performed to determine whether the cells are cancerous. Biopsy may be done by an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment tissue is obtained for histologic examination which may be done via frozen section or paraffin section. In more recent developments percutaneous techniques have been used to remove the entire mass during the initial procedure.

The type of biopsy utilized depends in large part on the circumstances present with respect to the patient and no single procedure is ideal for all cases. Core biopsy, however, is extremely useful in a number of conditions and is being used more frequently.

Intact tissue from the organ or lesion is preferred by medical personnel in order to arrive at a definitive diagnosis regarding the patient's condition. In most cases only part of the organ or lesion need be sampled. The portions of tissue extracted must be indicative of the organ or lesion as a whole. In the past, to obtain adequate tissue from organs or lesions within the body, surgery was performed so as to reliably locate, identify and remove the tissue. With present technology, medical imaging equipment such as stereotactic x-ray, fluoroscopy, computer tomography, ultrasound, nuclear medicine and magnetic resonance imaging, may be used. These technologies make it possible to identify small abnormalities even deep within the body. However, definitive tissue characterization still requires obtaining adequate tissue samples to characterize the histology of the organ or lesion.

Mammography can identify non-palpable (not perceptible by touch) breast abnormalities earlier than they can be diagnosed by physical examination. Most non-palpable breast abnormalities are benign but some are malignant. When breast cancer is diagnosed before it becomes palpable, breast cancer mortality can be reduced. It is still difficult to determine if pre-palpable breast abnormalities are malignant, as some benign lesions have mammographic features which mimic malignant lesions and some malignant lesions have mammographic features which mimic benign lesions. Thus, mammography has its limitations. To reach a definitive diagnosis, tissue from within the breast must be removed and examined under a microscope.

The introduction of stereotactic guided percutaneous breast biopsies offered alternatives to open surgical breast biopsy. With time, these guidance systems have become more accurate and easier to use. Biopsy guns were introduced for use in conjunction with these guidance systems. Accurate placement of the biopsy guns was important to obtain useful biopsy information because only one small core could be obtained per insertion at any one location. To sample the lesion thoroughly, many separate insertions of the instrument had to be made.

Biopsy procedures may benefit from larger tissue samples being taken, for example, tissue samples as large as 10 mm across. Many of the prior art devices required multiple punctures into the breast or organ in order to obtain the necessary samples. This practice is both tedious and time consuming.

One further solution to obtain a larger tissue sample is to utilize a device capable of taking multiple tissue samples with a single insertion of an instrument. An example of such a device is found in U.S. Pat. No. 5,195,533 to Chin et al. which describes a technique for extracting multiple samples with a single insertion of the biopsy device. Generally, such biopsy instruments extract a sample of tissue from a tissue mass by either drawing a tissue sample into a hollow needle via an external vacuum source or by severing and containing a tissue sample within a notch formed on a stylet. Typical of such devices utilizing an external vacuum source are U.S. Pat. No. 5,246,011 issued to Cailouette and U.S. Pat. No. 5,183,052 issued to Terwiliger. Such devices generally contemplate advancing a hollow needle into a tissue mass and applying a vacuum force to draw a sample into the needle and hold the same therein while the tissue is extracted.

When extracting multiple samples with a single insertion of the biopsy device using suction to either draw in tissue or remove the tissue from the body, it is important that the vacuum path remain unclogged. If the vacuum path clogs, the sample removal will become difficult or impossible. This may necessitate multiple insertions of the device or reduce the sample mass per extraction.

Therefore, a continuing need exists for percutaneous biopsy apparatus and methods which can reliably extract adequate biopsy sample(s) with a single insertion of the biopsy instrument.

SUMMARY

One particular embodiment of the present disclosure provides a surgical biopsy apparatus which includes a housing; a first elongated tubular member removably mounted in the housing and defining a fluid passageway therein, the first elongated tubular member including: a tapered closed distal end portion adapted to penetrate tissue; a laterally disposed tissue receiving opening formed near the tapered distal end which includes a tissue support surface defining a plurality of holes in fluid communication with the fluid passageway; and a second elongated tubular member rotatably and reciprocatingly disposed coaxially about the first elongated tubular member, the second elongated tubular member having a cutting edge formed at an open distal end thereof and a lateral tissue discharge port formed proximally of the cutting edge.

A third elongated tubular member is also provided which is removably supported by the housing and coaxially disposed about the first and second elongated tubular members, the third elongated member being movable from a retracted position to an extended position wherein a distal end portion is disposed laterally adjacent a distal-most position of the tissue receiving opening of the first elongated tubular member. The third elongated member may be radiolucent to permit the passage of x-rays therethrough and may also include a radiopaque marking formed on a portion of the third elongated member such that when the third elongated tubular member is in the deployed position the radiopaque marking is laterally adjacent the distal-most position of the tissue receiving opening of the first elongated tubular member.

In one aspect of the biopsy apparatus a tissue stripping member is disposed adjacent the lateral tissue discharge port, the tissue stripping member including a flexible extended portion configured and dimensioned to enter the tissue receiving opening of the first elongated tubular member upon alignment of the tissue receiving opening with the lateral tissue discharge port. The tissue stripping member may include a friction reducing coating formed thereon to reduce friction with body tissue coming in contact with the tissue stripping member.

In another aspect of the presently disclosed biopsy apparatus, the tissue support surface of the laterally disposed tissue receiving opening has an arcuate cross-section.

In another embodiment, the present disclosure provides a surgical biopsy apparatus which includes a housing; a first elongated tubular member removably mounted in the housing and defining a fluid passageway therein, the first elongated tubular member including: a tapered closed distal end portion adapted to penetrate tissue; a laterally disposed tissue receiving opening formed near the tapered distal end; a second elongated tubular member rotatably and reciprocatingly disposed coaxially about the first elongated tubular member, the second elongated tubular member having a cutting edge formed at an open distal end thereof and a lateral tissue discharge port formed proximally of the cutting edge; and a tissue marking member removably insertable through the second elongated tubular member, the tissue marking member including: an elongated shaft; a clamp disposed at a distal end of the elongated shaft, the clamp being operable from a first orientation configured and dimensioned to retain a tissue marker therein and a second orientation to deform a tissue marker retained by the clamp thereby attaching the tissue marker to body tissue of a patient.

In another embodiment, the present disclosure provides a method of performing a surgical biopsy which includes the steps of: a) inserting a biopsy apparatus into the tissue of a patient, the biopsy apparatus including an inner tubular member having a tapered penetrating end formed on the distal end and an outer tubular member held longitudinally fixed relative to the inner tubular member during the insertion step; b) retracting the outer tubular member relative to the inner tubular member to expose a laterally disposed tissue receiving area formed on the inner tubular member; c) applying suction to a series of openings formed along an inner surface of the tissue receiving area to pull tissue into the tissue receiving area; c) severing tissue disposed within the tissue receiving area by advancing the outer tubular member over the inner tubular member such that a cutting surface formed on the distal end of the outer tubular member rotates as it passes over the tissue receiving area; and d) removing the severed tissue sample from the tissue sampling site by retracting the inner tubular member from the outer tubular member until the tissue receiving area is aligned with a lateral opening formed in the outer tubular member wherein a tissue stripping plate urges the tissue sample out of the tissue receiving area.

BRIEF DESCRIPTION OF THE DRAWINGS

Various embodiments are described herein with reference to the drawings, wherein:

FIG. 2 is an exploded perspective view of the biopsy apparatus embodiment of FIG. 1;

FIG. 3 is an enlarged perspective view of a tip portion of the biopsy apparatus embodiment of FIG. 1;

FIG. 4 is an exploded perspective view of a vacuum assembly of the biopsy apparatus embodiment of FIG. 1;

FIG. 5 is a cross-sectional view taken along section line 5—5 of FIG. 4;

FIG. 6 is a cross-sectional view taken along section line 6—6 of FIG. 4;

FIG. 11 is a cross-sectional view of the biopsy apparatus taken along section line 11—11 of FIG. 1;

FIG. 12 is an enlarged cross sectional view of the indicated area of detail as shown in FIG. 11;

FIG. 14 is a side view of the biopsy apparatus showing a clamped breast prior to insertion of a penetrating tip;

FIG. 15 is a side view of the biopsy apparatus showing a clamped breast after insertion of a penetrating tip into a target tissue mass;

FIG. 19 is a perspective view of the biopsy apparatus showing the bottom of the apparatus;

FIG. 20 is an enlarged perspective view of the tip of the biopsy apparatus showing the indicated area of detail of FIG. 19;

FIG. 25 is a cross-sectional view of the biopsy apparatus tip portion showing a stripper plate and a tissue sample prior to removal of the tissue from the apparatus;

FIG. 26 is a cross-sectional view of the biopsy apparatus tip portion showing the stripper and the tissue sample during removal of the tissue from the apparatus;

FIG. 28 is a perspective view of the biopsy apparatus showing the vacuum knob in a first position;

FIG. 29 is a perspective view of the biopsy apparatus showing the vacuum knob in a second position rotated from the first position of FIG. 29 and also showing the lateral opening rotated;

FIG. 40 is a perspective view with parts separated showing the component parts of the disposable loading unit of FIG. 39;

FIG. 41 is an enlarged perspective view of a distal end portion of the disposable loading unit illustrating a tissue receiving basket of the biopsy apparatus;

FIG. 42 is a cross-sectional view taken along section lines 42—42 of FIG. 39;

FIG. 43 is an enlarged view of the area of detail as indicated in FIG. 42;

FIG. 44 is an enlarged view of the area of detail as indicated in FIG. 42;

FIG. 45 is an enlarged view of the area of indicated detail as indicated in FIG. 42;

FIG. 50 is an enlarged view of the distal end portion of the biopsy apparatus disposed within a target tissue mass with a knife tube fully advanced;

FIG. 51 is a side cross-sectional view showing the biopsy apparatus with the knife tube retracted;

FIG. 52 is an enlarged cross-sectional view of the distal portion of the biopsy apparatus disposed within a target tissue mass with a knife tube fully retracted and a vacuum source supplying suction to a tissue basket of the biopsy apparatus;

FIG. 53 is a view similar to FIG. 52, which shows the knife tube rotating and advancing distally thereby severing the tissue enclosed within a tissue basket of the biopsy apparatus;

FIG. 53A is a cross-sectional view of a tissue basket taken along section line 53A—53A of FIG. 53;

FIG. 54 is a section view looking distally taken along section line 54—54 of FIG. 42;

FIG. 55 is a view similar to FIG. 54, which shows the release of a vacuum tube locking mechanism;

FIG. 56 is a broken perspective view of the biopsy apparatus showing rotation of the tissue basket and vacuum tube which corresponds to the movement indicated in FIG. 55;

FIG. 57 is a cross-sectional view of the biopsy apparatus showing withdrawal of the vacuum tube from the disposable loading unit;

FIG. 58 is an enlarged view of the indicated area of detail of FIG. 57, which shows stripping of a severed tissue sample from within a tissue basket of the biopsy apparatus;

FIG. 62 is a perspective view of a tissue marking apparatus constructed in accordance with the present disclosure;

FIG. 63 is an enlarged view of the indicated area of detail shown in FIG. 62;

FIG. 64 is an enlarged partial perspective view of the distal end portion of the tissue marking apparatus of FIG. 62;

FIG. 66 is a perspective view of the tissue marking apparatus of FIG. 62 inserted through a knife tube of the biopsy apparatus;

FIG. 67 is an enlarged view of the indicated area of detail shown in FIG. 66;

FIG. 68 is an enlarged view of the indicated area of detail shown in FIG. 66;

DETAILED DESCRIPTION OF PREFERRED EMBODIMENTS

The present disclosure is directed to an apparatus and method for the biopsy of tissue specimens and, more particularly, to a single insertion multiple sample percutaneous biopsy apparatus and method. In general, the apparatus includes a series of concentric members, the inner most of which includes a tip portion which has a lateral opening that is introduced into a target tissue mass in a patient's breast. Suction is applied which is communicated to an area adjacent the lateral opening through a vacuum plate to draw at least a portion of the target tissue mass into the lateral opening. A knife tube is advanced distally around the outside of the vacuum tube while rotating, in order to sever the target tissue portion from the surrounding tissue mass. Once the target tissue portion is severed, the vacuum tube with the tip portion is retracted through the knife tube in order to remove the sample. In particular, upon refraction, the lateral opening is exposed adjacent to a tissue receptacle location. Retraction of the vacuum tube to the tissue receptacle location brings a stripper plate into contact with the target tissue portion, removing it from the vacuum plate and preferably causing it to fall into a receptacle.

Figure 1:
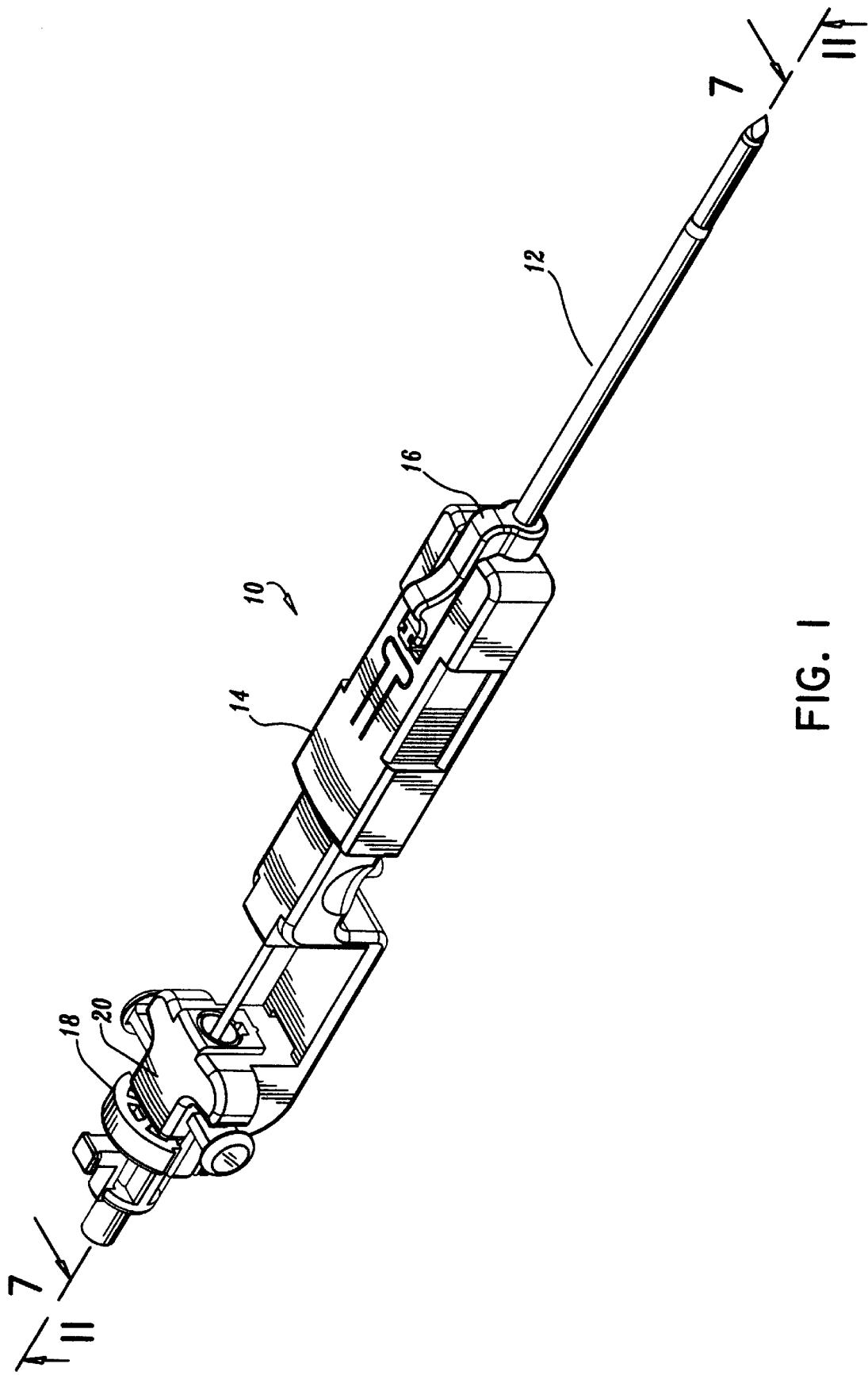
FIG. 1 is a perspective view of one embodiment of a percutaneous biopsy apparatus constructed in accordance with the present disclosure.

Referring now in specific detail to the drawings in which like reference numerals identify similar or identical elements throughout the several views, and initially to FIG. 1, one embodiment of a percutaneous biopsy apparatus is shown generally as apparatus 10. Apparatus 10 is preferably in the form of disposable loading unit which is adapted for attachment to a reusable driver housing. Apparatus 10 includes an insertion end portion 12 configured and dimensioned for percutaneous introduction into a patient. Insertion end portion 12 extends from a distal end 16 of a housing 14. A vacuum hub 18 is removably connected to a proximal end 20 of housing 14. Further details of the components and method are detailed herein.

Referring to FIG. 2, housing 14 defines a first bore 24 at a proximal end portion 26. First bore 24 removably receives vacuum hub 18 therein.

A vacuum knob 28 is removably received in the proximal end opening of vacuum hub 18. Vacuum knob 28 has a bore formed longitudinally therethrough for communicating suction to an elongated vacuum tube 32. Housing 14 further defines a second bore 34. First bore 24 and second bore 34 are axially aligned with each other. Distal end portion 36 and proximal end portion 26 are rigidly connected by a tissue receiving bay 38. Vacuum tube 32, when inserted, extends through first bore 24 and second bore 34 of housing 14. Vacuum tube 32 is mounted in fluid communication with bore 30 of vacuum knob 28 and is connected thereto at a proximal end 40. Vacuum tube 32 has a distal end portion 42 which includes penetrating insertion tip portion 44.

A hollow gear shaft 46 having a gear 48 disposed thereon is attached to a hollow knife tube 50. Gear shaft 46 has a flanged end 52 on a distal end portion 54. A proximal end 56 of knife tube 50 is received in flanged end 52 of gear shaft 46. A proximal end portion 58 of gear shaft 46 is rotatably disposed in second bore 34 of housing 14. When assembled, vacuum tube 32 is disposed within gear shaft 46 and knife tube 50.

Figure 18:
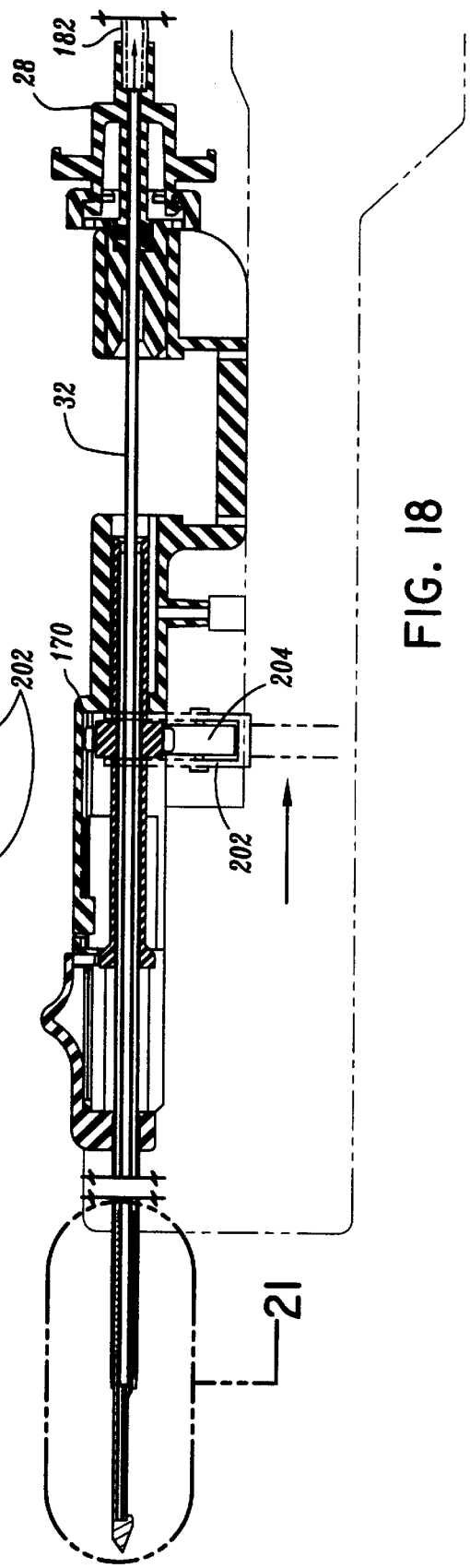
FIG. 18 is a cross-sectional view of the biopsy apparatus showing a gear and a gear shaft fully retracted.

A support slide 60 is slidably mounted on housing 14 in a slot 62 formed adjacent distal end portion 16. Slot 62 includes tracks 64 formed for receiving tabs 66 formed at a proximal end portion 68 of support slide 60. A distal end portion 70 of support slide defines a stepped bore 72 formed therein. A hollow and preferably radiolucent support tube 76 is securely disposed in bore 72 (as best shown in FIG. 18). Thus, bore 72 is dimensioned to allow vacuum tube 32 and tip portion 44 to pass therethrough while engaging a proximal end 78 of support tube 76. When assembled, knife tube 50 is disposed within support tube 76.

Referring to FIG. 3, a magnified view of the distal end portion of insertion tip portion 44 is shown. A spring 80 is disposed on vacuum tube 32 and is captured between a proximal end 82 of a tissue basket 84 and a retaining ring portion 86 of a stripper plate 88. Tissue basket 84 has a distal end 90 forming a penetrating tip 92 thereon. Insertion tip portion 44 is dimensioned to fit within knife tube 50 to permit relative longitudinal movement of the two elements.

Referring to FIG. 4, a vacuum assembly 9—assembly 18 (FIG. 1). Vacuum hub subassembly 18 includes attachment port 22 and vacuum knob 28. Proximal end 40 of vacuum tube 32 is received in a bore 100 defined at a distal end portion 98 of vacuum knob 28. Distal end portion 98 defines a groove 102 for securing an o-ring 104 which facilitates engagement with attachment port 22 and permits rotation therein. A pair of tabs 106 are oppositely disposed on vacuum knob 28. Tabs 106 have corresponding actuator buttons 108 attached thereto for deflecting tabs 106 for engagement to attachment port 22. Tabs 106 are cantilevered to allow relatively high degree of deflection on end portions 110 of tabs 106. Vacuum knob 28 has a proximal end portion 112 for connecting to a vacuum source (not shown).

Attachment port 22 defines a plurality of circularly arrayed openings 114 therein for receiving tabs 106 of vacuum knob 28. Attachment port 22 has tabs 116 oppositely disposed thereabout. Tabs 116 have corresponding actuator buttons 118 attached thereto for deflecting tabs 116 for engagement to mounting base 14 (FIG. 2). An extension tube 120 on attachment port 22 defines a bore 122 therethrough dimensioned to allow sliding contact with vacuum tube 32 during operation. Extension tube 120 has a key 124 longitudinally disposed thereon. A keyway 126 is formed in first bore 24 of housing 14 (FIG. 2) such that when extension tube 120 is attached to housing 14, key 124 fits into keyway 126 thereby indexing attachment port 22 to housing 14.

Tissue basket 84 defines a lateral opening 128 formed therein. Lateral opening 128 is in fluid communication with vacuum tube 32 during operation and extends substantially the length of tissue basket 84. Lateral opening 128 supports a vacuum plate 130 which has a plurality of holes 132 formed therethrough. During operation, each of holes 132 fluidly communicates with vacuum tube 32 and aids in preventing tissue from entering vacuum tube 32. Lateral opening 128 also supports a tissue-stripping end portion 134 of stripper plate 88. Stripping end portion 134 slidably contacts the upper surface of vacuum plate 130, thereby aiding in the removal of tissue samples as described hereinafter. Spring 80 is mounted on distal end 42 of vacuum tube 32. Distal end 42 of vacuum tube 32 is attached to proximal end 82 of tissue basket 84.

Tissue-stripping end portion 134 of stripper plate 88 has a tissue engagement end 136 which includes lateral tabs 138 extending therefrom. Stripping end portion 134 defines recesses 140 disposed proximally to lateral tabs 138 and defines an opening 142 in fluid communication with vacuum tube 32. Stripping end portion 134 is curved with respect to a middle portion 144 of stripper 88. Middle portion 144 of stripper 88 and tissue engagement end 136 are axially offset but remain substantially parallel. Middle portion 144 slidably engages a flat upper proximal surface 146 formed on proximal end portion 82 of tissue basket 84. During operation, knife tube 50 prevents middle portion 144 of the stripper 88 from being separated from flat surface 146 (FIG. 2). Ring portion 86 of stripper 88 is shown in FIG. 4 in an open position. When assembled, lateral extensions 148 are deformed into the shape of a ring such that spring 80 is captured between tissue bracket 84 and the ring 86 which is closed about vacuum tube 32, thereby slidably attaching ring 86 thereto.

Referring to FIGS. 4, 5 and 6, vacuum plate 130 is dimensioned to fit within lateral opening 128 and fits within a recess 150. When assembled, vacuum plate 130 is secured by stripping end portion 134 of stripper 88 and a slot 152 cut into tip 92. Lateral tabs 138 are slidably engaged within slots 154 maintaining vacuum plate 130 in place and ensuring engagement with vacuum plate 130 during stripping of tissue samples. Edges 156 are chamfered to aid in assembly and to allow tissue to more easily move against vacuum plate 130 during operation. A slot 158 extends along lateral opening to allow fluid communication with vacuum tube 32.

Figure 7:
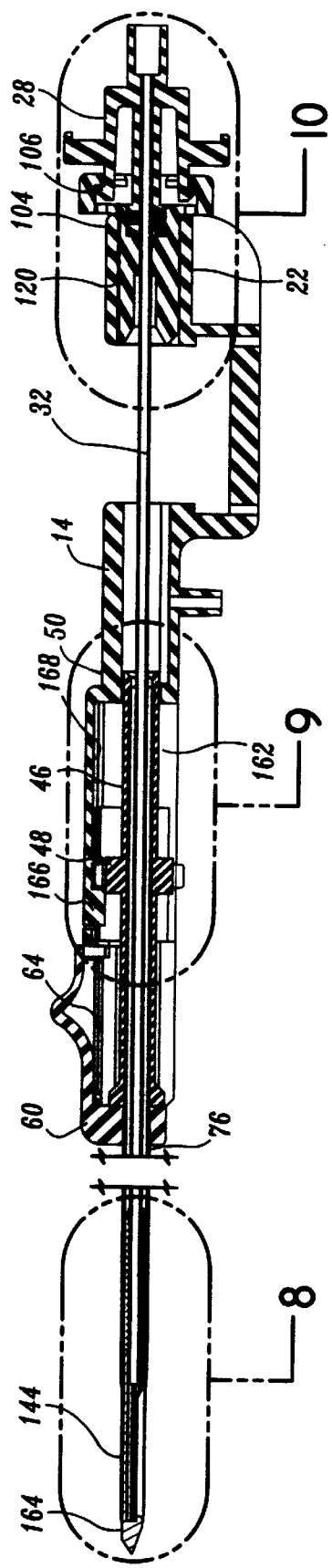
FIG. 7 is a cross-sectional view taken along section line 7—7 as shown in FIG. 1.
Figure 8:
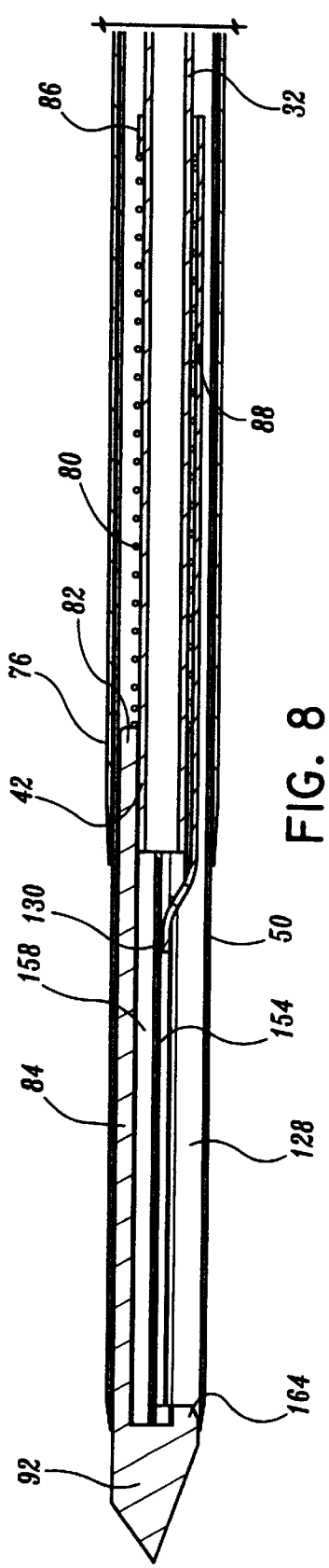
FIG. 8 is an enlarged cross-sectional view of the area of detail indicated in FIG. 7.
Figure 9:
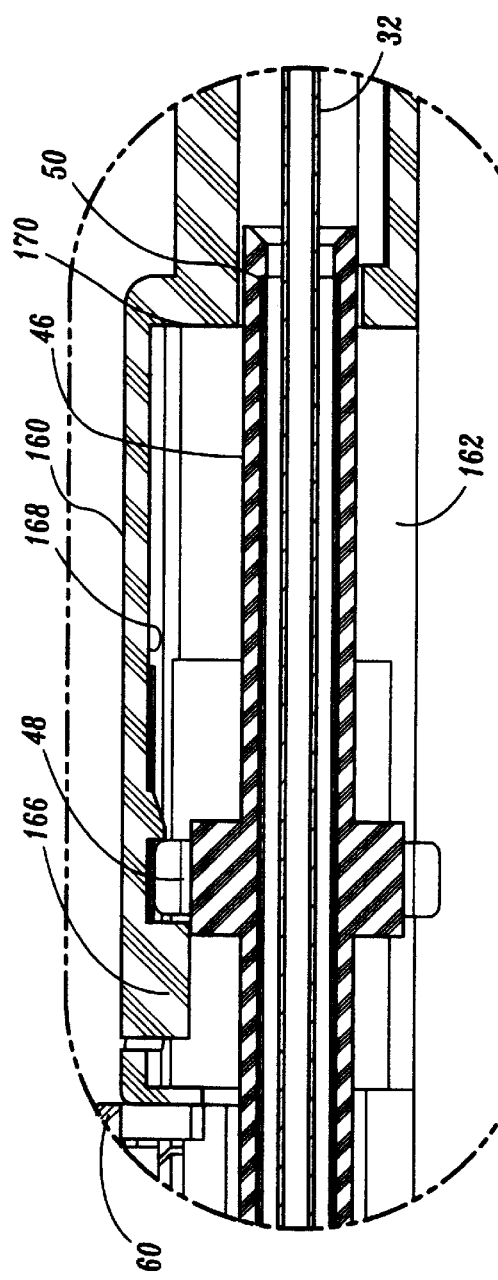
FIG. 9 is an enlarged cross-sectional view of the area of detail indicated in FIG. 7.
Figure 13:
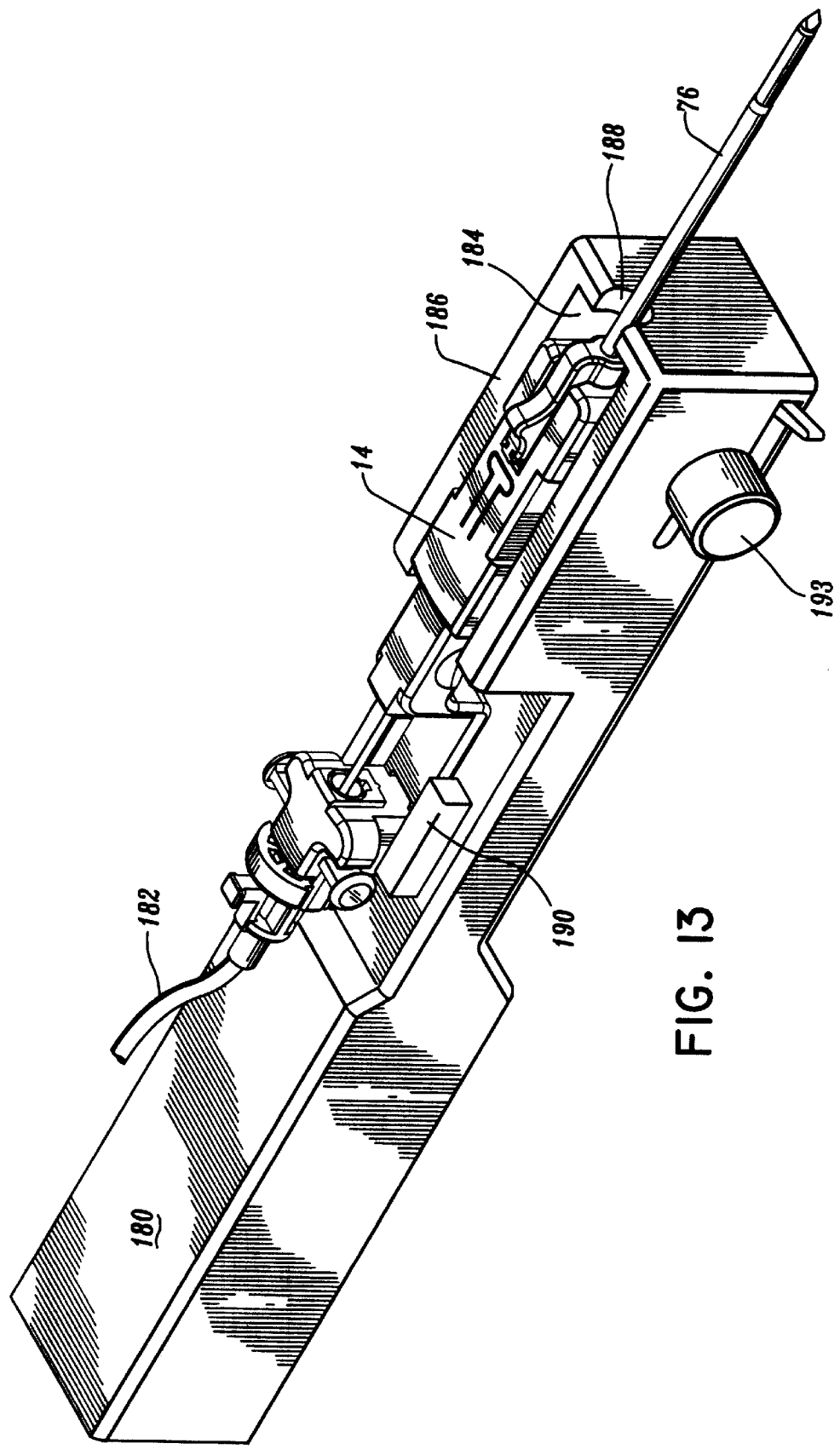
FIG. 13 is a perspective view of the biopsy apparatus mounted to a guidance and driver platform.

Referring to FIGS. 7–10, vacuum knob 28 is connected to attachment port 22 and secured thereto by tabs 106 and the engagement of o-ring 104. Extension tube 120 of attachment port 22 is disposed within first bore 24 of mounting base 14. Extension tube 120 is able to slide and rotate relative to first bore 24. Gear shaft 46 is disposed within second bore 34 of housing 14. Gear shaft 46 is able to slide and rotate within second bore 34. Housing 14 supports gear shaft 46 and gear 48 within a housing portion 160, as shown in FIG. 9. Housing portion 160 defines an opening 162 for a portion of gear 48 to be presented for manipulation of gear 48 and gear shaft 46 during operation. Gear 48 is preferably driven by a motor contained within driver and guidance platform 180 (FIG. 13). Knife tube 50 is attached within gear shaft 46. Knife tube 50 extends past mounting base 14 and engages a proximal end portion 164 of penetration tip 92 when knife tube 50 is fully advanced distally. Knife tube 50 extends through support slide 60. Gear shaft 46 engages support slide 60 such that when gear shaft 46 is advanced or retracted, support slide 60 tracks the motion of gear shaft 46 by sliding along tracks 64. The range of motion of gear shaft 46 is controlled by the placement of gear 48. In a fully advanced position 48 gear engages a stop 166 mounted on an interior surface 168 of housing portion 160. In a fully retracted position gear 48 engages an interior wall 170 of housing portion 160. As shown in FIG. 7, support tube 76 extends from support slide 60. Knife tube 50 is disposed in support tube 76, and vacuum tube 32 and tip portion 44 are disposed in knife tube 50.

Referring to FIG. 8, knife tube 50 is shown fully advanced and contacting proximal end portion 164 of penetration tip 92. Lateral opening 128 is closed off when knife tube 50 is advanced. Stripper plate 88 is initially positioned in a retracted position. Spring 80 maintains a slight force on ring portion 86 and proximal end 82 of tissue bracket 84 to maintain stripper plate 88 in the initially retracted position. Stripper plate 88 engages vacuum plate 130 and is disposed in slot 154. Distal end 42 of vacuum tube 32 is attached to proximal end 82 of trocar 84. Support tube 76 is also disposed about knife tube 50.

Referring to FIG. 9, housing portion 160 defines an opening 162 for a portion of gear 48 to be presented for manipulation of gear 48 and gear shaft 46 during operation. The range of motion of gear shaft 46 is controlled by the placement of gear 48. In a fully advanced position 48 gear engages a stop 166 mounted on an interior surface 168 of housing portion 160. In a fully retracted position gear 48 engages an interior wall 170 of housing portion 160.

Figure 10:
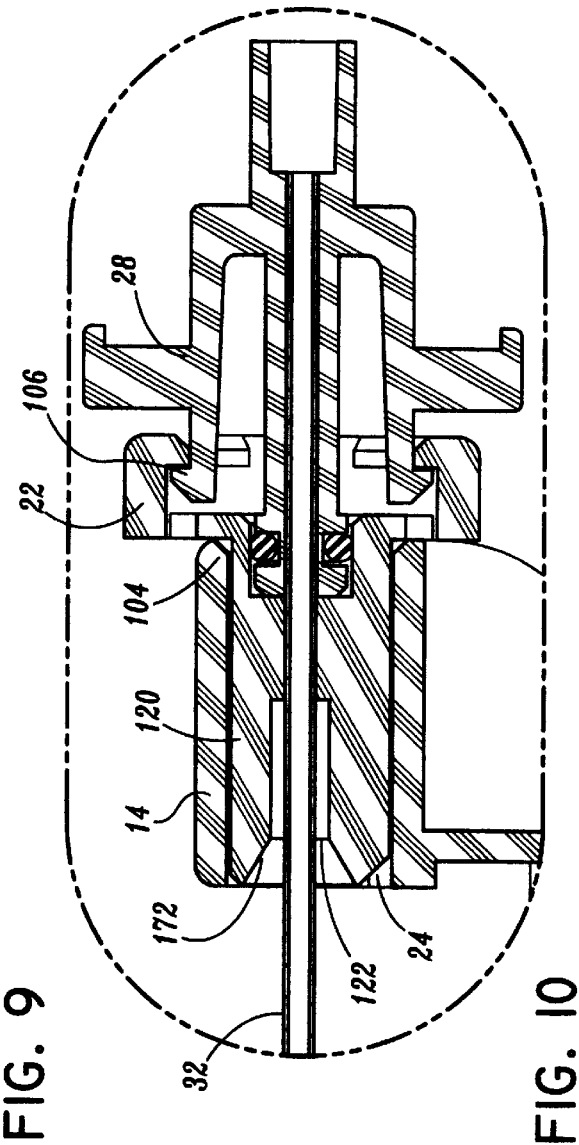
FIG. 10 is an enlarged cross-sectional view of the area of detail indicated in FIG. 7.

Referring to FIG. 10, vacuum knob 28 is connected to attachment port 22 and secured thereto by tabs 106 and the engagement of o-ring 104. Extension tube 120 of attachment port 22 is disposed within first bore 24 of mounting base 14. Extension tube 120 is able to slide and rotate relative to first bore 24. Bore 122 of extension tube 120 is dimensioned to receive ring portion 86 and spring 80 (FIG. 3). Edges 172 are chamfered to aid in receiving ring portion 86 and spring 80 therein during the collection of tissue samples.

Referring to FIG. 11, distal end portion 16 of housing 14 has slot 62 formed therein. Slot 62 receives flanged end 52 of gear shaft 46.

Referring to FIG. 12, housing 14 has extension portions 174 oppositely disposed about proximal end portion 20. Extension portions 174 have a lip 176 disposed thereon. Tabs 116 of attachment port 22 engage lip 176 and secure attachment port 22 to housing 14.

Referring to FIG. 13, housing 14 is mounted on a driver guidance platform 180 in order to perform the biopsy procedure. Platform 180 is configured and dimensioned for attachment to an instrument positioning stage of a stereotactic imaging apparatus. Examples of such apparatus are available from LORAD Corporation of Danbury, Conn. or from Fischer Imaging Corporation of Denver, Colo. Alternatively, apparatus 10 may be adapted to fit on any other suitable imaging apparatus such as, for example, ultrasound. A vacuum source (not shown) is connected by a vacuum hose 182 to proximal end portion 112 of vacuum knob 28. Platform 180 is used to stabilize apparatus 10 and provide power and support thereto during the biopsy procedure. Platform 180 includes a partially enclosed area 184 at a distal end portion 186. Partially enclosed area 184 provides structure for maintaining housing 14 in a secured position relative to platform 180. Distal end portion 186 of platform 180 defines an opening 188 to allow support tube 76 to extend therefrom. Housing 14 is further stabilized by a block 190 which is attached to platform 180. Platform 180 also includes a motor which drives a gear that engages gear 48 and further includes a compression spring released by a trigger which serves to shoot apparatus 10 the final distance, approximately ¾ of an inch, into the tissue. One or more control knobs such as control knob 193 may be provided to control the advancement and retraction of knife tube 50 and vacuum tube 32.

In operation, referring to FIGS. 14 and 15, a patient's breast 192 is disposed between a movable clamp 194 and a stationary clamp 196. Movable clamp 192 is moved toward stationary clamp 194 capturing breast 192 therebetween. Upon securing breast 192 in position an image is taken of a target tissue mass 198 within breast 192. Apparatus 10 is aimed at target tissue mass 198 utilizing the positioning capabilities of the imaging and guidance system such that insertion end portion 12 is aligned with tissue mass 198. Stationary clamp 196 defines an opening 200 therethrough to allow insertion portion 12 to enter breast 192. Before insertion into breast 192, gear shaft 48 and, therefore, knife tube 50 are fully advanced distally to enclose lateral opening 128 in trocar 84 (FIG. 8). The surgeon may manually place a nick utilizing a scalpel at the point of insertion of tip 92 to facilitate easy entry into breast 192. Penetrator tip 92 is approximated adjacent the location of the nick into breast. Preferably, this is accomplished by the positioning capability of the imaging and guidance system. Insertion portion 12 is advanced distally into breast 192 by release of the stored energy of the compression spring in platform 180, e.g., by activating a trigger release mechanism, so that insertion tip portion 44 is located adjacent to or within target tissue mass 198, as required.

Figure 16:
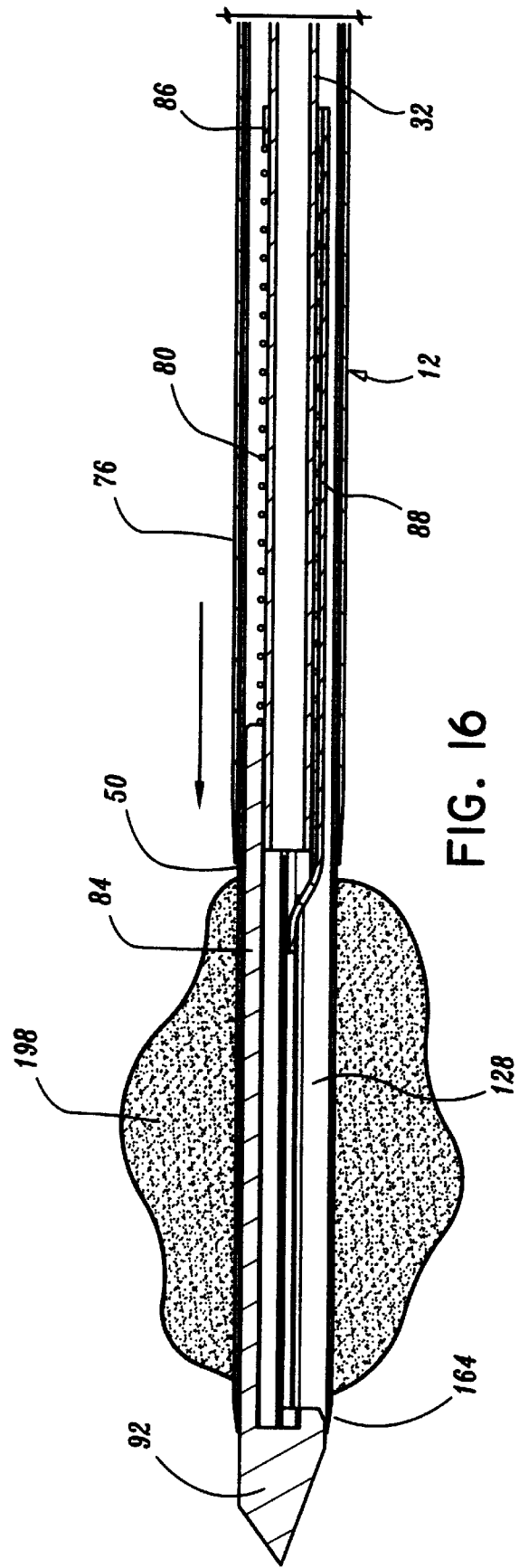
FIG. 16 is an enlarged cross-sectional view of a distal portion of the biopsy apparatus disposed within a target tissue mass with a knife tube fully advanced.

Referring to FIG. 16, insertion portion 12 is advanced into target tissue mass 198. The guidance system (not shown) can be used to monitor the location of insertion portion 12 to confirm target tissue mass 198 is positioned adjacent to lateral opening 128. As mentioned above, knife tube 50 is initially fully advanced distally and engages proximal end portion 164 of tip 92. Stripper plate 88 is disposed in a normally retracted position with spring 80 in a minimally compressed position applying a small force between tissue bracket 84 and ring portion 86.

Figure 17:
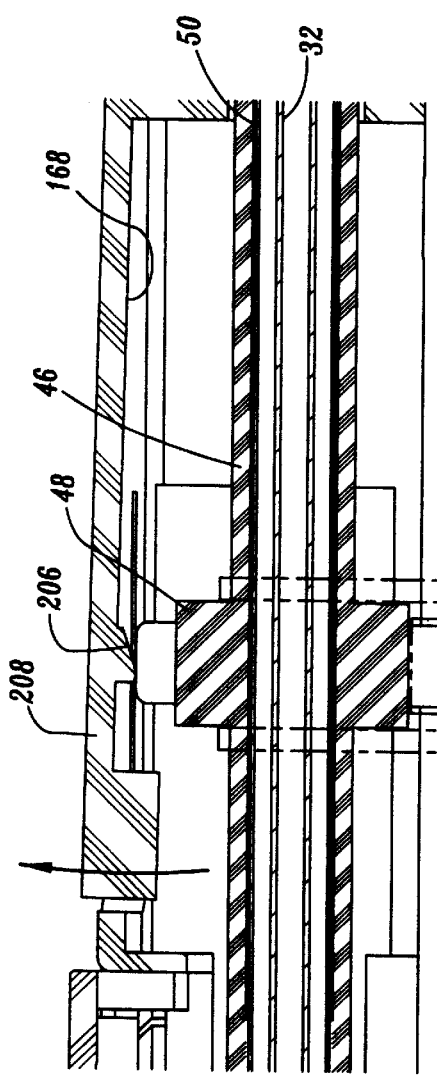
FIG. 17 is an enlarged cross-sectional view of a housing portion of the biopsy apparatus showing a gear and gear shaft being moved proximally.

Referring to FIG. 17, knife tube 50 is retracted proximally by retracting gear shaft 46 and gear 48. In one illustrative embodiment, gear 48 is coupled to support members 202. Support members 202 may support a drive gear 204 and may be driven by a driving mechanism (not shown). Driving mechanism rotates gear 48 by turning drive gear 204. Proximal and distal movement of gear 48 is accomplished by moving support members 202. Gear 48 is captured between stop 166 and a protrusion 206 extending from interior surface 168 of housing portion 160 when fully distally advanced. As previously described, this position corresponds to knife tube 50 engaging proximal end portion 164 of tip 92 thereby closing off lateral opening 128. Protrusion 206 is attached to a cantilever member 208 which allows deflection of protrusion 206 to enable gear 48 to be released therefrom and moved proximally. As gear is moved past protrusion 206 cantilever member 208 rebounds to its initial position.

Referring to FIG. 18, gear 48 is fully retracted proximally by support members 202 and drive gear 204 to a position abutting interior wall 170. Knife tube 50 is thereby retracted proximally exposing lateral opening 128 to target tissue mass 198. Suction is applied to vacuum tube 32 through vacuum knob 28 from the vacuum source (not shown) via vacuum hose 182.

Referring to FIGS. 19 and 20, a perspective view of apparatus 10 shows gear shaft 46 and gear 48 disposed in a proximal-most position within housing portion 160 of housing base 14. Knife tube 50 is retracted exposing tissue basket 84. Stripper plate 88 and vacuum plate 130 are shown within lateral opening 128, and stripping end portion 134 extends into slots 154.

Figure 21:
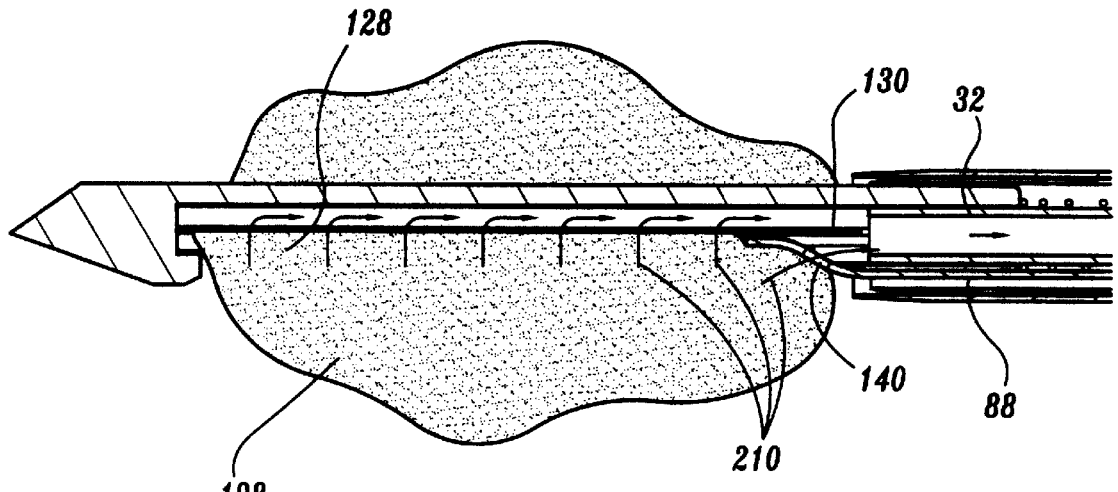
FIG. 21 is an enlarged cross-sectional view of the indicated area of detail of FIG. 18 showing suction lines and tissue mass being drawn into a lateral opening formed in the biopsy apparatus.

Referring to FIG. 21, applied suction draws a portion of target tissue mass 198 into lateral opening 128. Suction flow arrows 210 show the direction and location of the force exerted on target tissue mass 198. The suction force passes through the plurality of holes 132 in vacuum plate 130 and through opening 140 in stripper 88.

Figure 22:
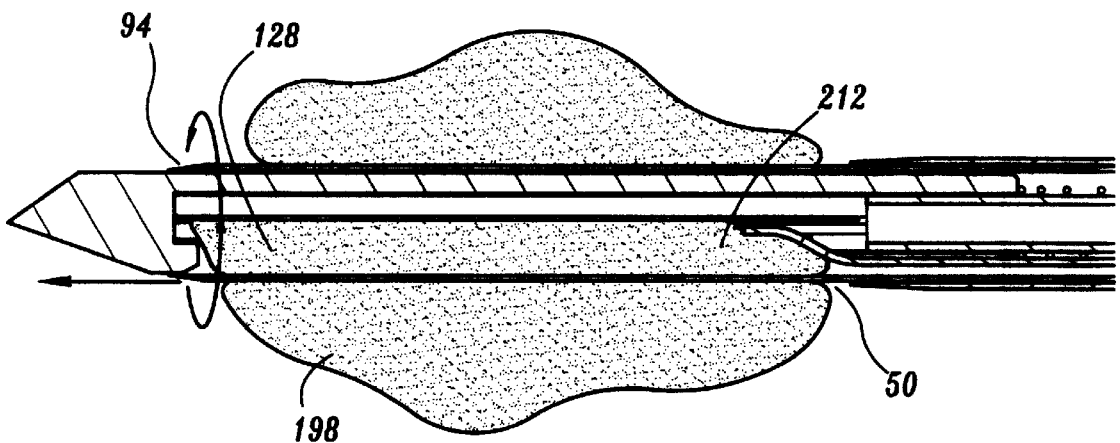
FIG. 22 is an enlarged cross-sectional view of the indicated area of detail of FIG. 18 showing a knife tube being rotated and advanced distally to sever a tissue mass into the lateral opening in the biopsy apparatus.

Referring to FIG. 22, suction is maintained for a predetermined amount of time to allow lateral opening 128 to gather a desired amount of target tissue mass 198 therein. Knife tube 50 is simultaneously rotated and advanced to sever a tissue sample 212 from target tissue mass 198 using an annular knife edge 94 formed at the distal end of knife tube 50. Knife tube 50 is rotated and advanced distally by drive gear 204 and support members 202, respectively, in the same manner as mentioned with reference to FIG. 17. When tissue sample 212 is enclosed by knife tube 50 suction is no longer needed and may be removed.

Figure 23:
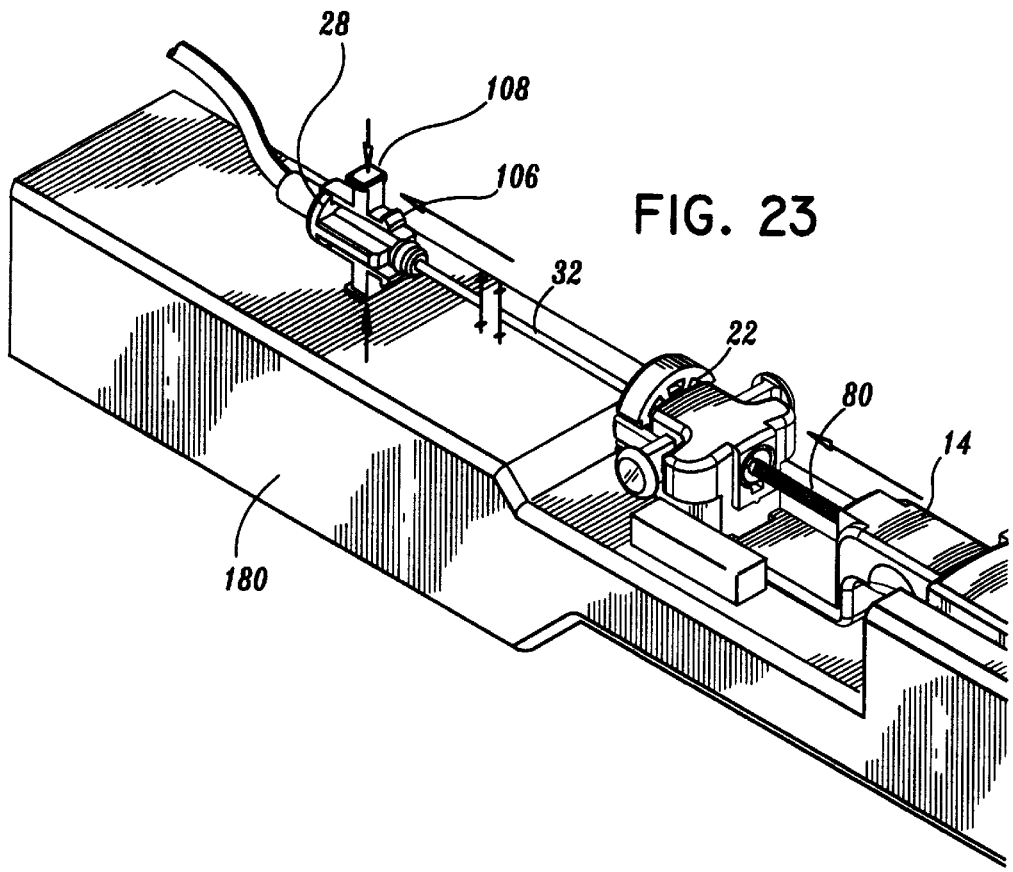
FIG. 23 is a perspective view of a proximal portion of the biopsy apparatus mounted on the guidance and driving platform showing a vacuum knob detaching from an attachment port in order to retract a vacuum tube and tip portion.
Figure 24:
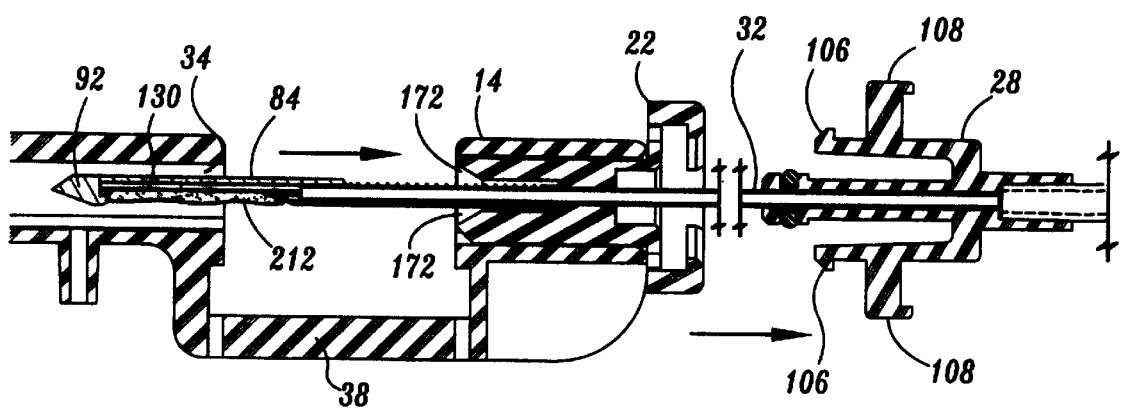
FIG. 24 is a cross-sectional view of a distal portion of the biopsy apparatus showing the vacuum knob detached from the attachment port in order to retract vacuum tube and tip portion.

Referring to FIGS. 23 and 24, vacuum knob 28 is detached from attachment port 22 by depressing buttons 108 to release tabs 106 from holes 114. Vacuum knob 28 is translated proximally to retract vacuum tube 32. Proximal translation of vacuum tube 32 removes tip portion 44 from knife tube 50 exposing tissue sample 212 at tissue bay 38. If desired, suction may be continued during the translation of vacuum tube 32 to maintain tissue sample 212 against vacuum plate 130 within tissue basket 84. Vacuum tube 32 is retracted until ring portion 86 and spring 80 are disposed within bore 124 of extension tube 120. Edges 172 are chamfered to aid in receiving ring portion 86 and spring 80 therein. As tissue basket 84 begins to exit second bore 34 of housing 14, tissue sample 212 is held over tissue receptacle portion 38 of housing 14. Vacuum tube 32 may be rotated to ensure that tissue basket 84 is facing downwardly towards tissue receptacle portion 38 of housing 14.

Figure 27:
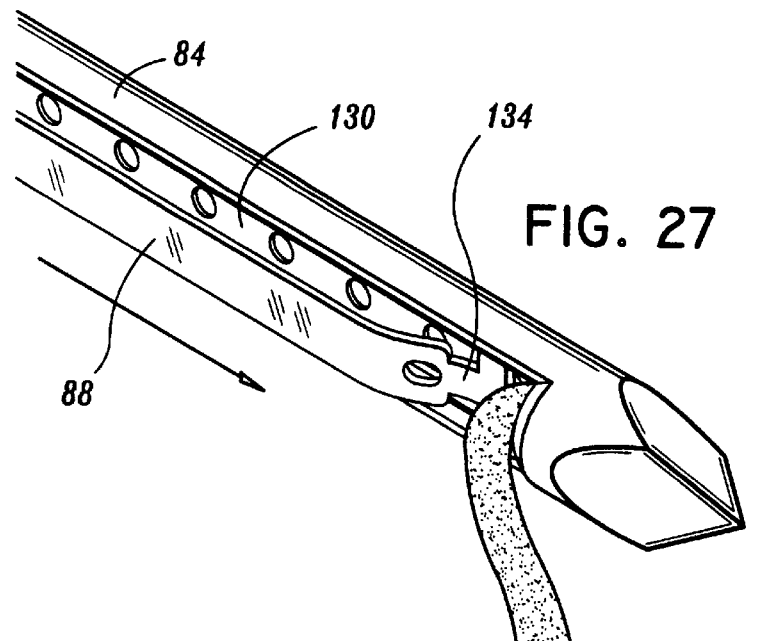
FIG. 27 is an enlarged perspective view of the biopsy apparatus tip portion showing the stripper plate and tissue sample during removal of the tissue from the apparatus.

Referring to FIGS. 25, 26 and 27, ring portion 86 engages a stepped portion 214 within extension tube 120. As proximal translation of vacuum tube 32 continues spring 80 begins to become compressed between tissue basket 84 and ring portion 86. As spring 80 compresses, stripper plate 88 is advanced distally having stripping end portion 134 running in slots 154 and in engagement with vacuum plate 130. As stripper plate 88 advances, tissue sample 212 is stripped away from vacuum plate 130 and falls out of tissue basket 84. Tissue sample 212 can now be collected for examination.

Referring to FIGS. 28 and 29, a preferred embodiment of apparatus 10 is shown. FIG. 28 shows a first position for vacuum knob 28. Vacuum knob 28 is secured to attachment port 22 by placing tabs 106 within holes 114 as described above and illustrated in FIG. 3. Vacuum knob 28 is attached to vacuum tube 32 during the collection of tissue sample 212 by the method described with reference to FIGS. 14–27 above. During the collection of tissue sample 212, support tube 76 and knife tube 50 can be left within breast 192 (FIGS. 14 and 15) while vacuum tube 32 is extracted.

After the collection of tissue sample 212, vacuum tube 32 may be reinserted through support tube 12 and knife tube 50 into breast 192 (FIGS. 14 and 15). An additional tissue sample or samples may be extracted from the same location. FIG. 29 shows vacuum knob 28 rotated to angularly displace the orientation of lateral opening 128. When vacuum knob 22 is rotated, vacuum tube 32 is also rotated causing lateral opening 128 to be angularly displaced. When inserted in breast 192 (FIGS. 14 and 15), lateral opening 128 may be rotated from a first position so that a different portion of target tissue mass 198 (FIGS. 14 and 15) may be extracted through a single insertion of apparatus 10. Vacuum knob 28 can be resecured to attachment port 22 by tabs 106 in holes 114. Holes 114 are disposed about attachment port 22 to allow vacuum knob 28 to be secured in a plurality of different rotated positions. For example, attachment port 22 can have ten securable positions by providing ten holes or five pairs of oppositely disposed holes. Each of the securable positions corresponds, for example, to an angular displacement of tissue basket 84 equal to about 36 degrees from an adjacent securable position.

Figure 32:
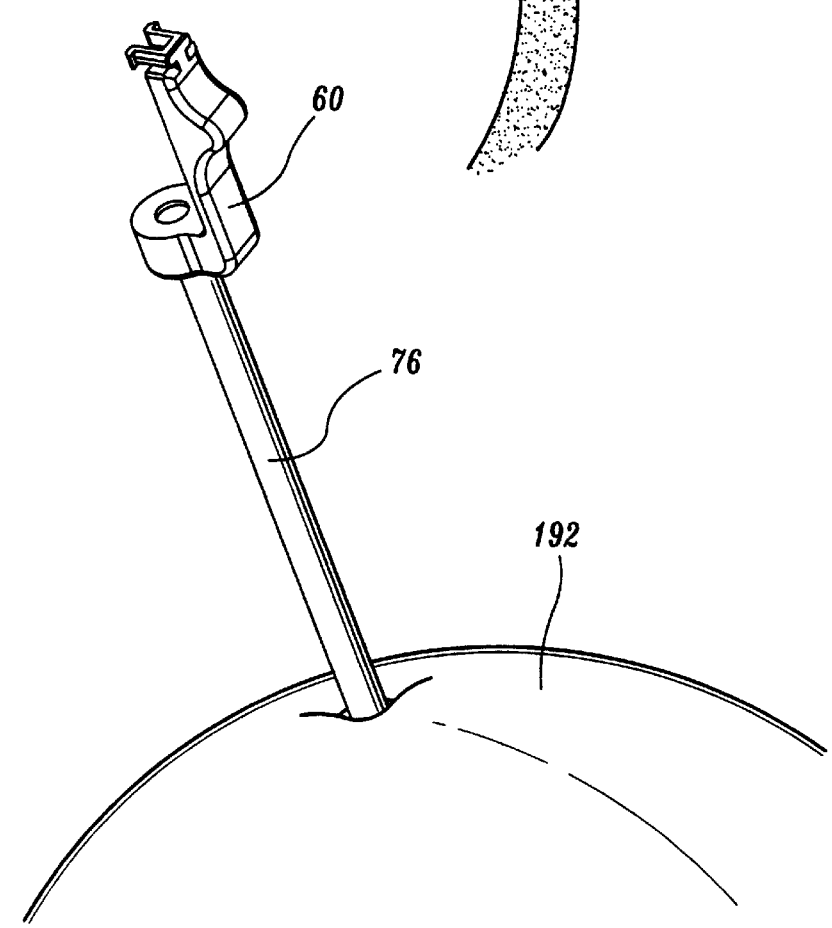
FIG. 32 is perspective view of a breast having a support tube retained therein.
Figure 30:
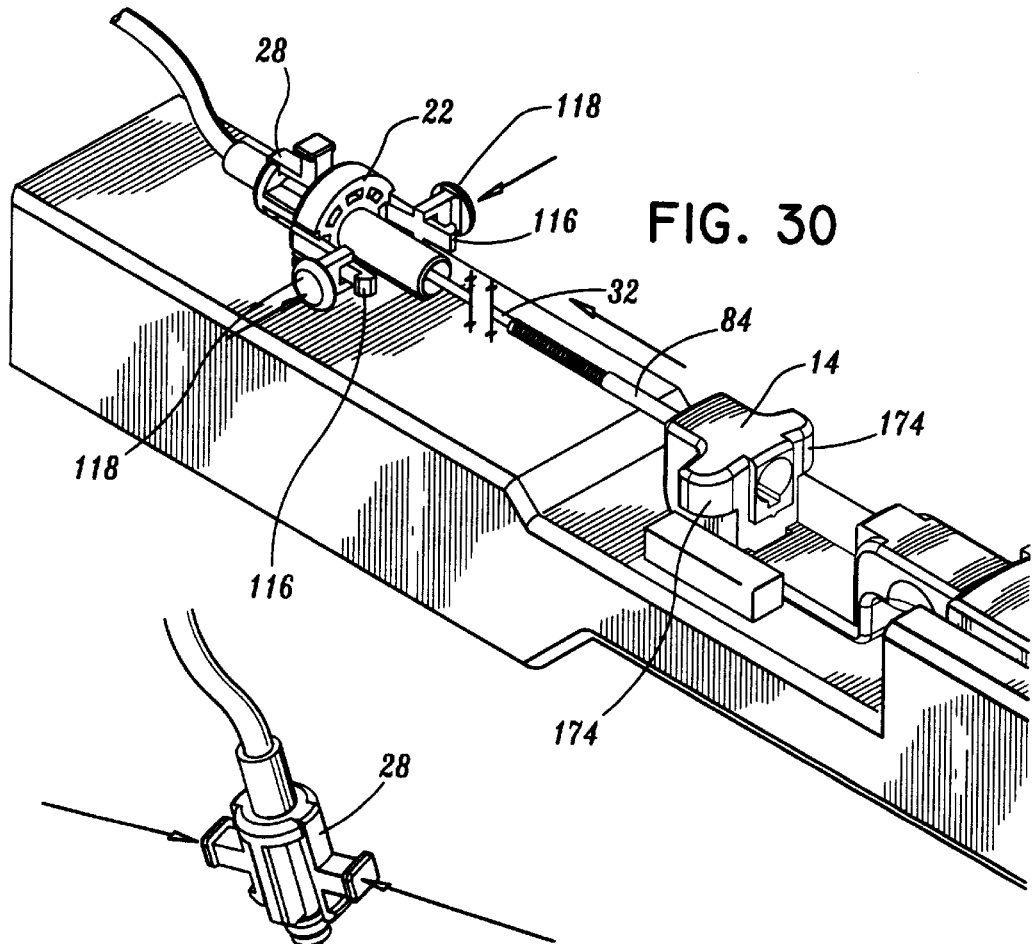
FIG. 30 is a perspective view of a portion of the biopsy apparatus showing the attachment port detached and being retracted.
Figure 31:
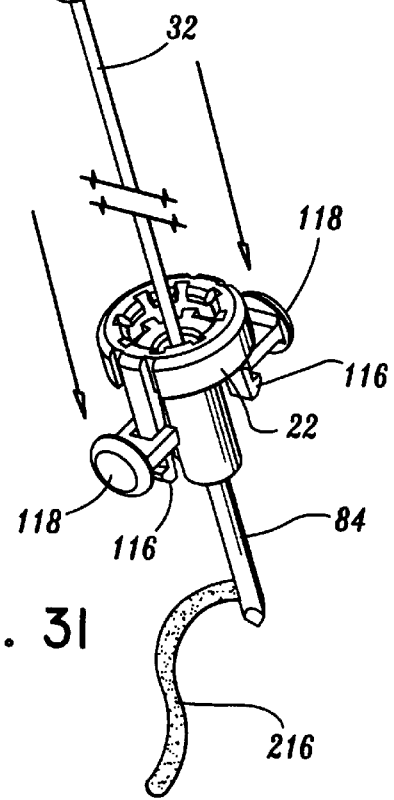
FIG. 31 is a perspective view of the tissue sample being removed from the biopsy apparatus.

Referring to FIGS. 30 and 31, attachment port 28 is removable from housing 14. It may be desirable to remove a tissue sample 216 at a location different from tissue receiving portion 38 of housing 14. Attachment port 22 and vacuum knob 28 may be removed while being secured to each other. Buttons 118 may be depressed to release tabs 116 from extensions portions 174 of housing 14. Vacuum tube 32 is drawn proximally through housing 14 with tissue sample 216 disposed in tissue basket 84. Tissue basket 84 with tissue sample 216 may be positioned over a remotely located receptacle (not shown) for receiving tissue sample 216. Vacuum knob 28 is detached by deflecting tabs 106 as previously described above and moved apart from attachment port 22. Vacuum tube 32 is drawn through attachment port 22. Tissue sample 216 is then stripped from tissue basket 84 as described previously with reference to FIGS. 25 and 26. Referring to FIG. 32, it may be necessary to maintain access to breast 192 during or after the biopsy procedure. Support slide 60 is removable from housing 14 for this purpose. Support tube 76 is attached to support slide 60. Support tube 76 provides access to breast 192 for reinsertion of tissue bracket 84 and knife tube 50 to prevent having to make an additional insertion to reaccess breast 192.

Figure 33:
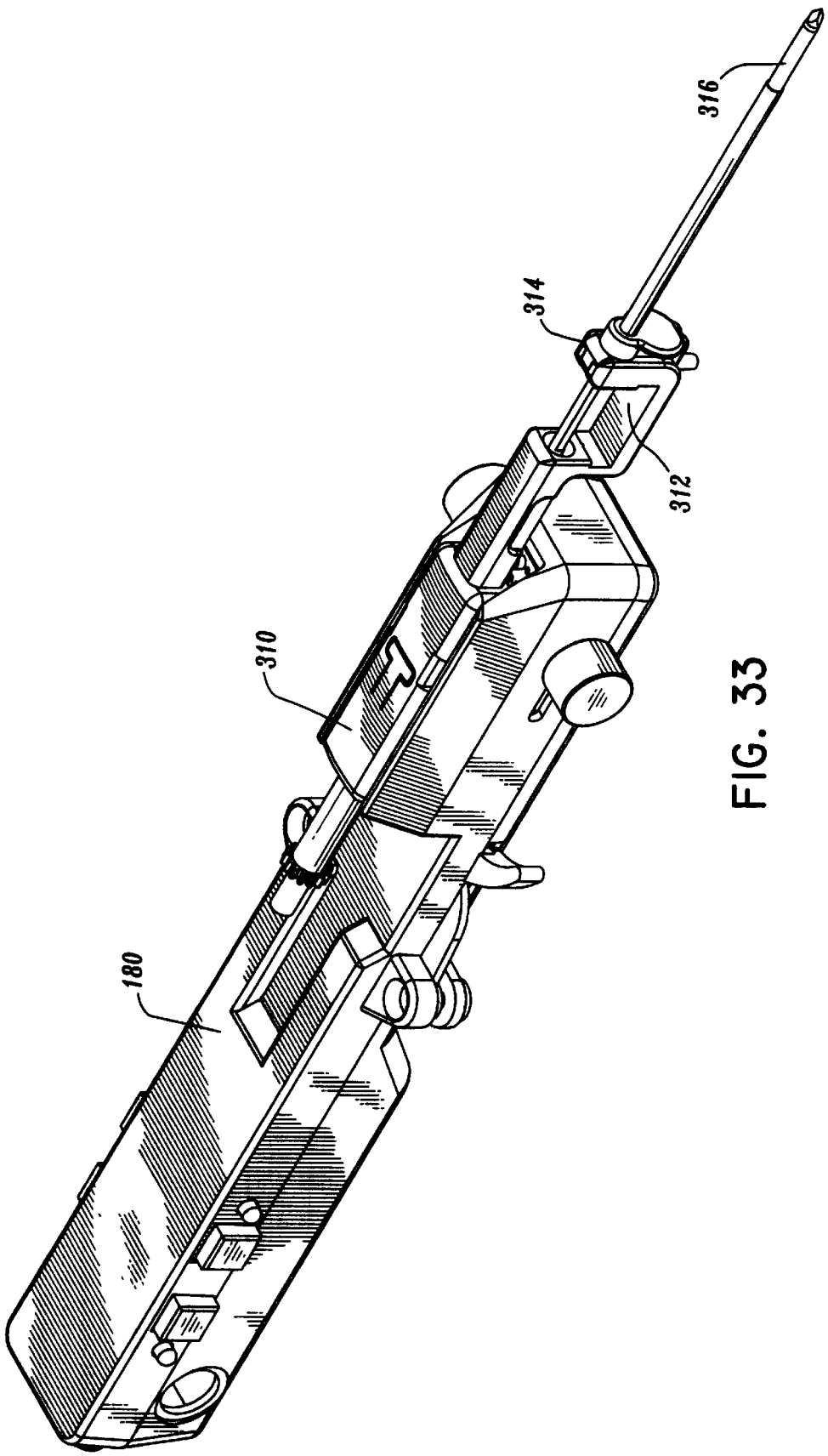
FIG. 33 is a colored three dimensional image of a biopsy apparatus mounted on a platform having a tissue tray at a distal end.
Figure 34:
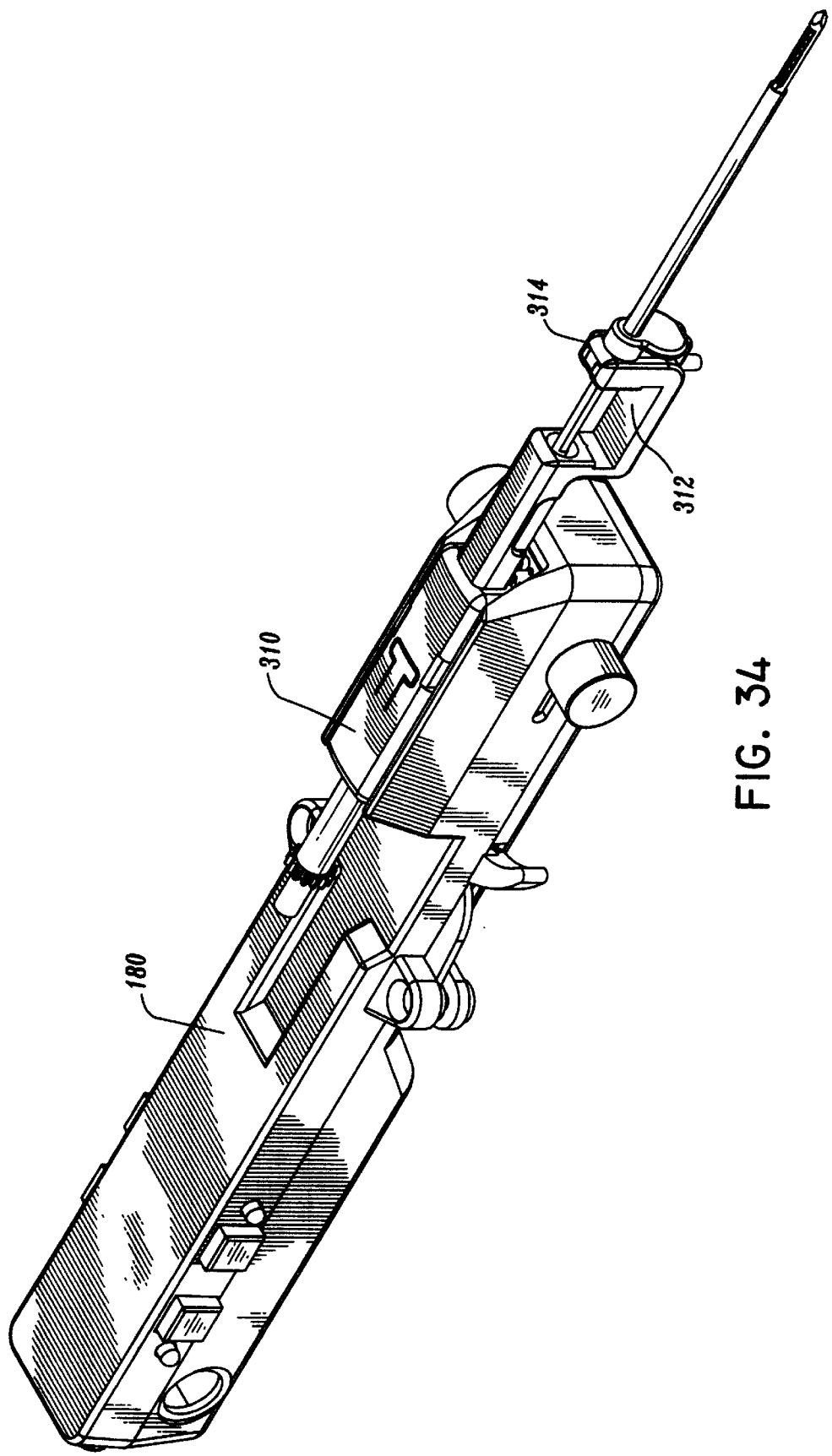
FIG. 34 is a perspective view of the biopsy apparatus of FIG. 33 having a knife tube retracted.
Figure 35:
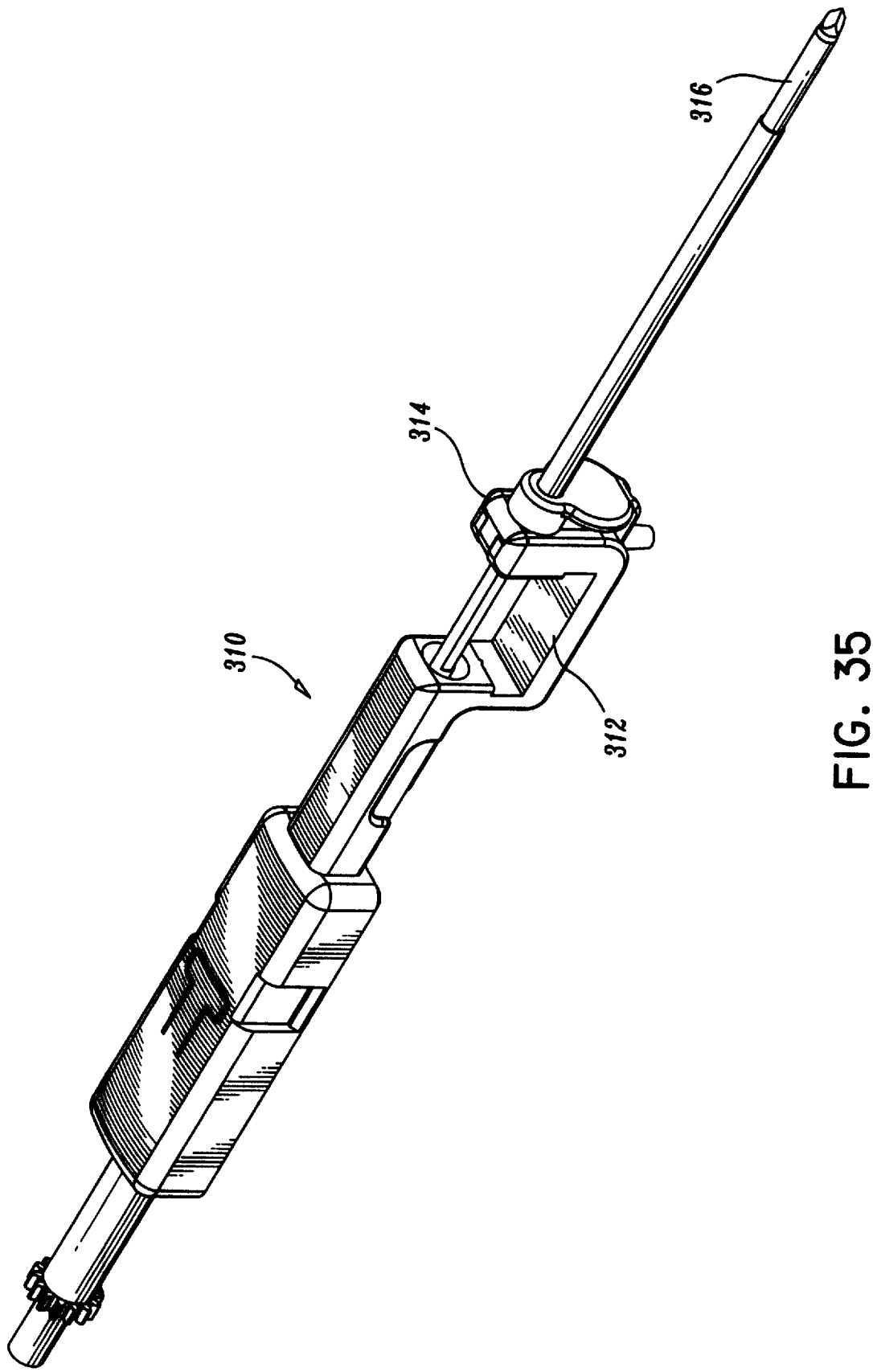
FIG. 35 is a perspective view of a biopsy apparatus having a tissue tray at a distal end.
Figure 36:
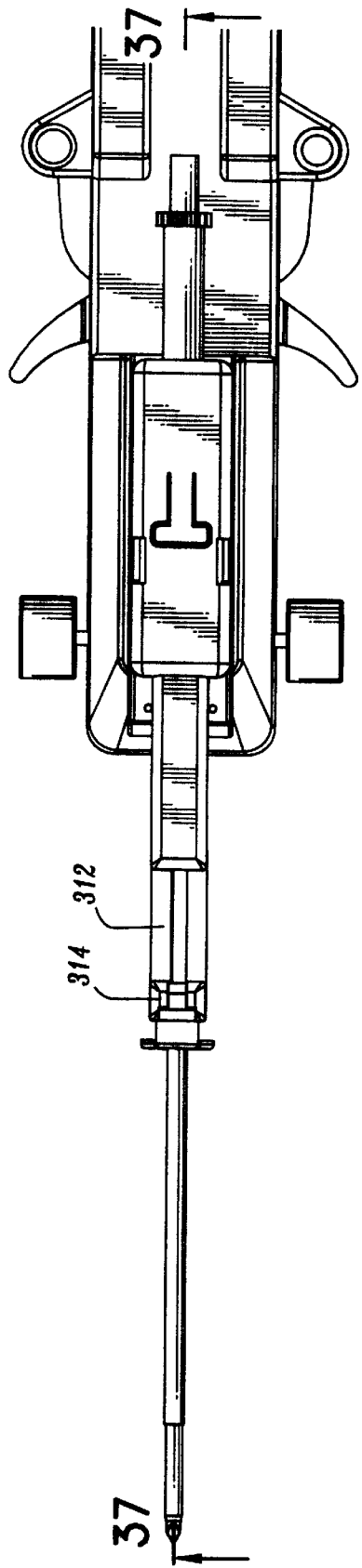
FIG. 36 is a side view of the biopsy apparatus of FIG. 33.
Figure 37:
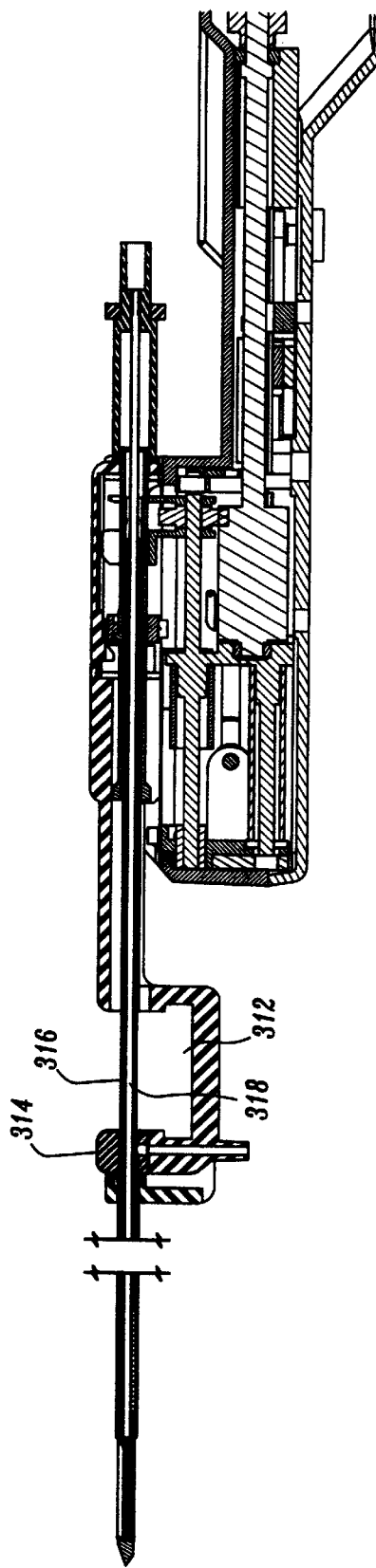
FIG. 37 is a cross-sectional view taken along section line 37—37 of FIG. 36.

Referring to FIGS. 33–37, an alternate embodiment of a biopsy apparatus 310 is mounted on driver guidance platform 180 in order to perform the biopsy procedure. Platform 180 is configured and dimensioned for attachment to an instrument positioning stage of a stereotactic imaging apparatus, such apparatus are available from LORAD Corporation of Danbury, Conn. or from Fischer Imaging Corporation of Denver, Colo. Alternatively, apparatus 310 may be adapted to fit on any other suitable imaging apparatus such as, for example, ultrasound. Apparatus 310 is reconfigured such that a tissue bay 312 is mounted at a distal end portion 314. A tissue sample (not shown) is severed and retrieved essentially as mentioned hereinabove. FIG. 33 shows a knife tube 316 in a fully advanced position, while FIG. 34 shows knife tube 316 retracted. Referring to FIG. 35, apparatus 310 is shown. Knife tube 316 defines an opening 318 therein for accessing tissue sample when they are obtained during the biopsy procedure.

Figure 38:
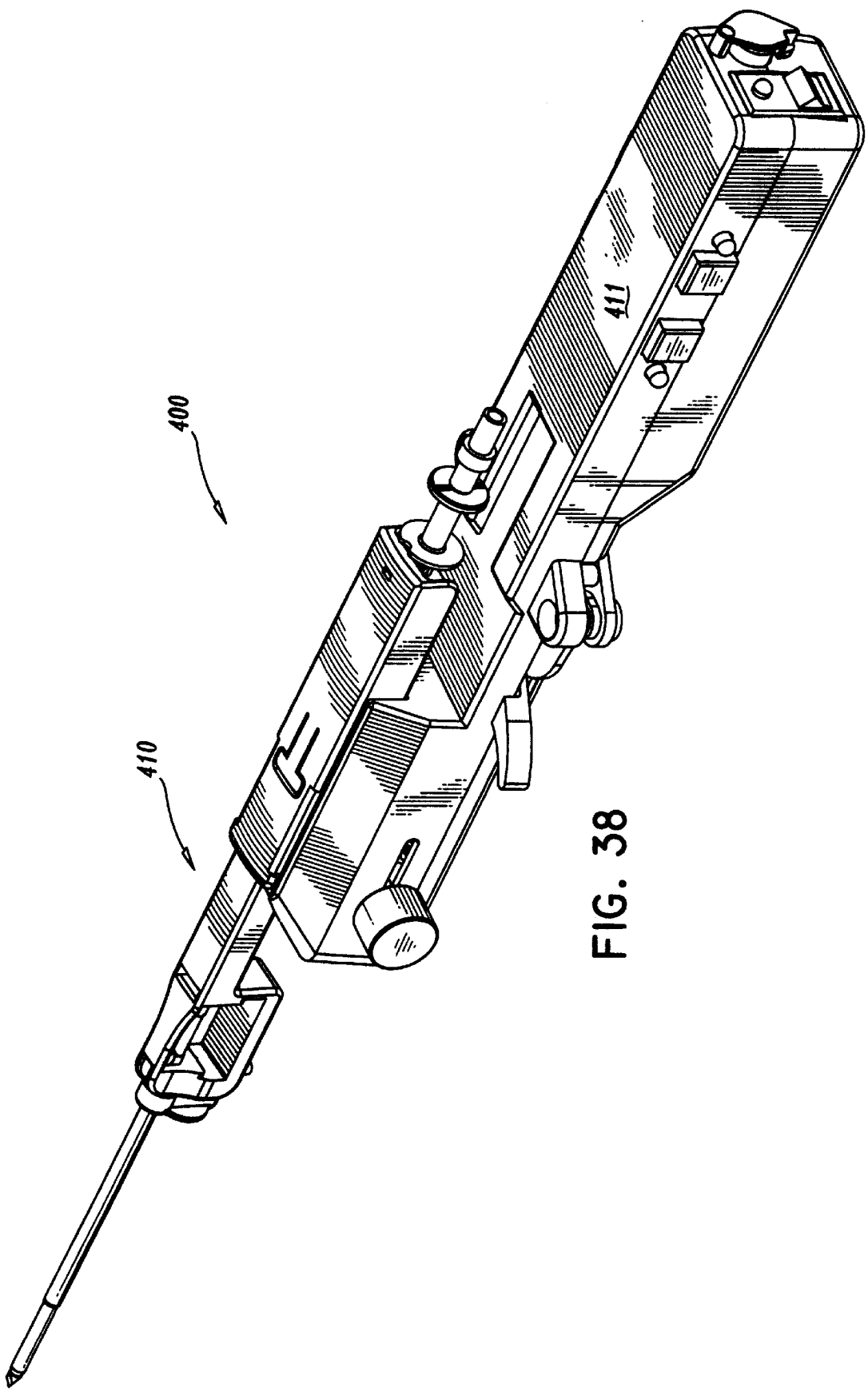
FIG. 38 is a perspective view of an alternate embodiment of a percutaneous biopsy apparatus constructed in accordance with the present disclosure.
Figure 38A:
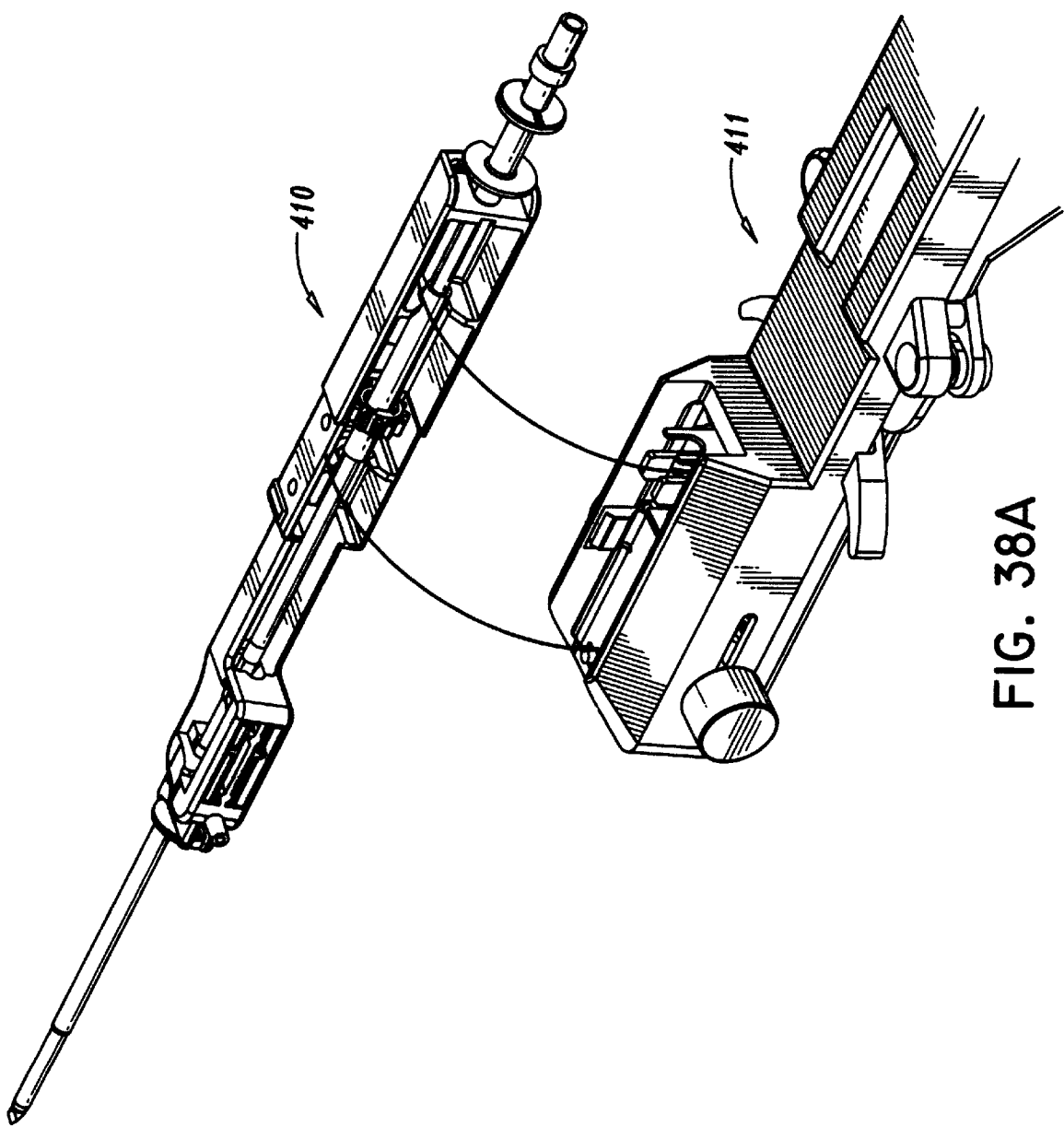
FIG. 38A is a partial perspective view which shows detachably mounting a biopsy apparatus on a drive unit.

Referring to FIGS. 38 and 38A, a further alternate embodiment of a percutaneous biopsy apparatus 410 is shown in FIGS. 38 and 38A mounted on a drive unit 411 which is configured and dimensioned for attachment to an instrument positioning stage of a stereotactic imaging apparatus (not shown). An example of a drive unit is disclosed in commonly assigned provisional application Ser. No. 60/078,748, entitled "Biopsy Instrument Driver Apparatus" filed on Feb. 20, 1998, the entire contents of which are hereby incorporated by reference. Examples of stereotactic imaging apparatus which are used to perform biopsy procedures are commercially available from LORAD Corporation of Danbury, Conn. or from Fischer Imaging Corporation of Denver, Colo. Alternatively, apparatus 410 may be adapted to fit on or interact with other suitable imaging apparatus such as, for example, ultrasound imaging devices such as are available from Neovision of Seattle, Wash. Biopsy apparatus 410 is structurally and operationally similar to biopsy apparatus embodiments 10 and 310 previously described herein. Accordingly, the following description of biopsy apparatus 410 will focus mainly on the features which are different on apparatus 410.

Referring now to FIGS. 40–47, biopsy apparatus 410 includes a housing 412 which supports a series of concentrically disposed tubular members. The first such tubular member is a knife tube 414 which has a beveled annular cutting surface 416 formed at the distal end thereof and a laterally facing tissue discharge port 418 disposed proximally of annular cutting surface 416. A series of vent holes 420 are formed through the side walls of knife tube 414 at points distal of tissue discharge port 418 to facilitate venting of fluids and the like which may travel up knife tube during operation of the instrument. To assist in the removal of fluids or the like, a laterally oriented vacuum port 421 is found adjacent the distal end of housing 412 and is preferably connected to a vacuum source (not shown) which may be actuated by the user. A gear shaft 422 is secured over the proximal end of knife tube 414 and has a gear 424 securely mounted about bosses 426 which are disposed on gear shaft 422. The assembled knife tube 414 is fitted into an axial passageway 428 formed longitudinally through housing 412. Knife tube 414 is disposed in axial passageway 428 such that simultaneous rotational and longitudinal translational movement thereof is facilitated.

A vacuum tube 430 is concentrically disposed within knife tube 414 such that a penetrating tip 432 extends out the distal end of knife tube 414 beyond annular cutting surface 416. In this manner, penetrating tip 432 and knife tube 414 form a substantially continuous penetrating assembly for insertion into a patient's tissue, for example, a compressed breast. As best shown in FIGS. 41–43, a tissue basket 434 is formed adjacent the distal end of vacuum tube 430. Tissue basket 434 faces laterally and is defined by a tissue support plate 436 which is provided with a series of vacuum holes 438 formed longitudinally therealong and a proximal-most vacuum hole 440 which is formed a distance away from the series of holes 438. Vacuum hole 440 is provided to assist in sealing off the distal end of knife tube 414 (FIG. 52) to prevent too great a loss of vacuum force through apparatus 410 so that the remaining vacuum holes 438 can efficaciously pull the target tissue into tissue basket 434. Tissue plate 436 is preferably arcuately shaped in cross section (FIG. 53A) and secured to vacuum tube 430 by welding or the like so that a substantially continuous surface depression is formed near the distal end of vacuum tube 430. This arcuate or sinusoidal shape of tissue plate 436 in combination with the fact that knife tube 414 represents the outer most diameter of apparatus 410 at the point of insertion facilitates taking larger tissue samples than with other existing tissue sampling apparatus geometries.

Referring now to FIG. 40 in conjunction with FIG. 45, a locking wheel and indexer 442 having a longitudinal bore 444 formed therethrough is secured adjacent the distal end of vacuum tube 430. Locking wheel 442 includes a tab member 446 which, when locking wheel 442 is mounted to vacuum tube 430, is radially aligned with tissue basket 434. In the locked orientation, tab 446 is situated behind a lip 448 formed on housing 412. This configuration prevents proximal movement of vacuum tube 430 and, therefore, penetrating tip 432 upon insertion of apparatus 410 into the patient. Additionally, a small notch 448 is formed on locking wheel 442 which is also aligned with tab 446 so as to provide the user with a visual indication of the relative orientation of tissue basket 434. A vacuum port adapter 450 is securely mounted to the distal end of vacuum tube 430 adjacent to locking wheel and indexer 442. Vacuum port adapter 450 facilitates the attachment of a vacuum hose which is connected to a vacuum source (not shown) to provide a vacuum supply to vacuum tube 430.

Figure 46:
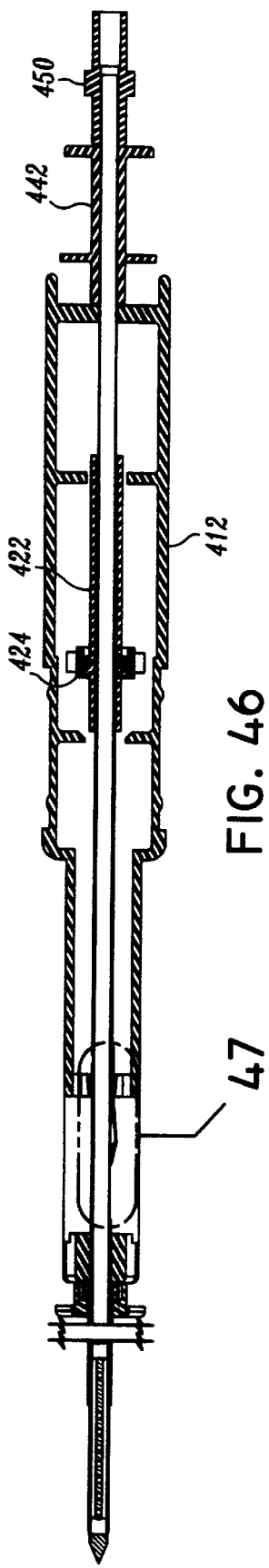
FIG. 46 is a cross-sectional view taken along section line 47—47 of FIG. 39.
Figure 47:
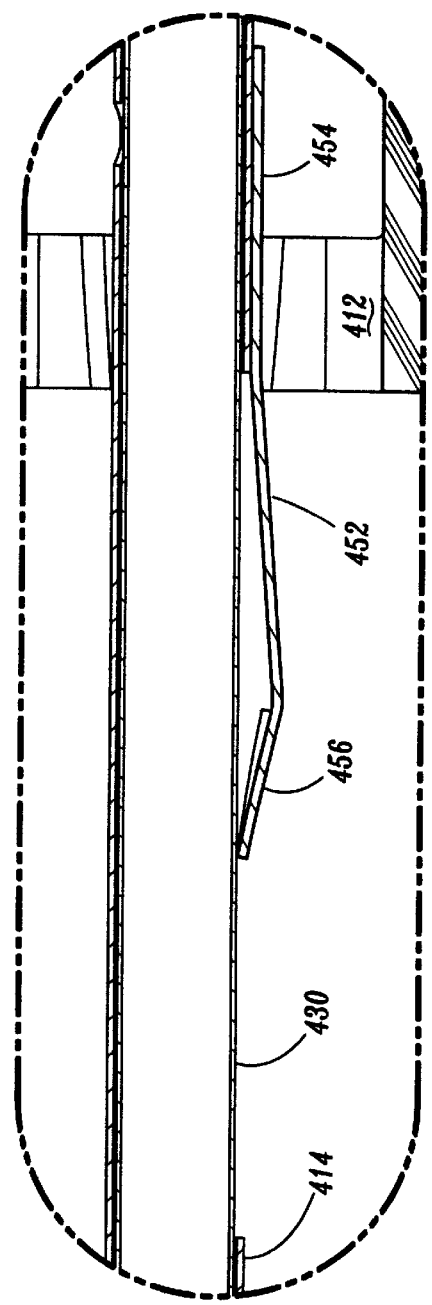
FIG. 47 is an enlarged view of the indicated area of detail of FIG. 46.

Extraction of the tissue sample from within tissue basket 434 is facilitated by a tissue stripping clip 452 which is in the form of a modified leaf spring having an open-sided collar portion 454 configured and dimensioned to clip onto knife tube 414 as shown in FIGS. 46 and 47, in alignment with tissue discharge opening 418. Tissue stripping clip 452 includes an inwardly deflected distal end portion 456 which is held biased against the outer surface of vacuum tube 430 to facilitate stripping of the sample tissue upon retraction of vacuum tube 430 within knife tube 414 (FIG. 57 and FIG. 58). Tissue stripping clip 452 may additionally be provided with a coating of material or lubricant to reduce the friction forces along the surface of tissue stripping clip 452 which come into contact with the sample tissue being extracted. In this manner, the tissue will be more readily removed from tissue basket 434 with less likelihood of adherence to tissue stripping clip 452. Any suitable known friction-reducing coatings may be applied to tissue stripping clip 452 and/or tissue plate 436.

Figure 39:
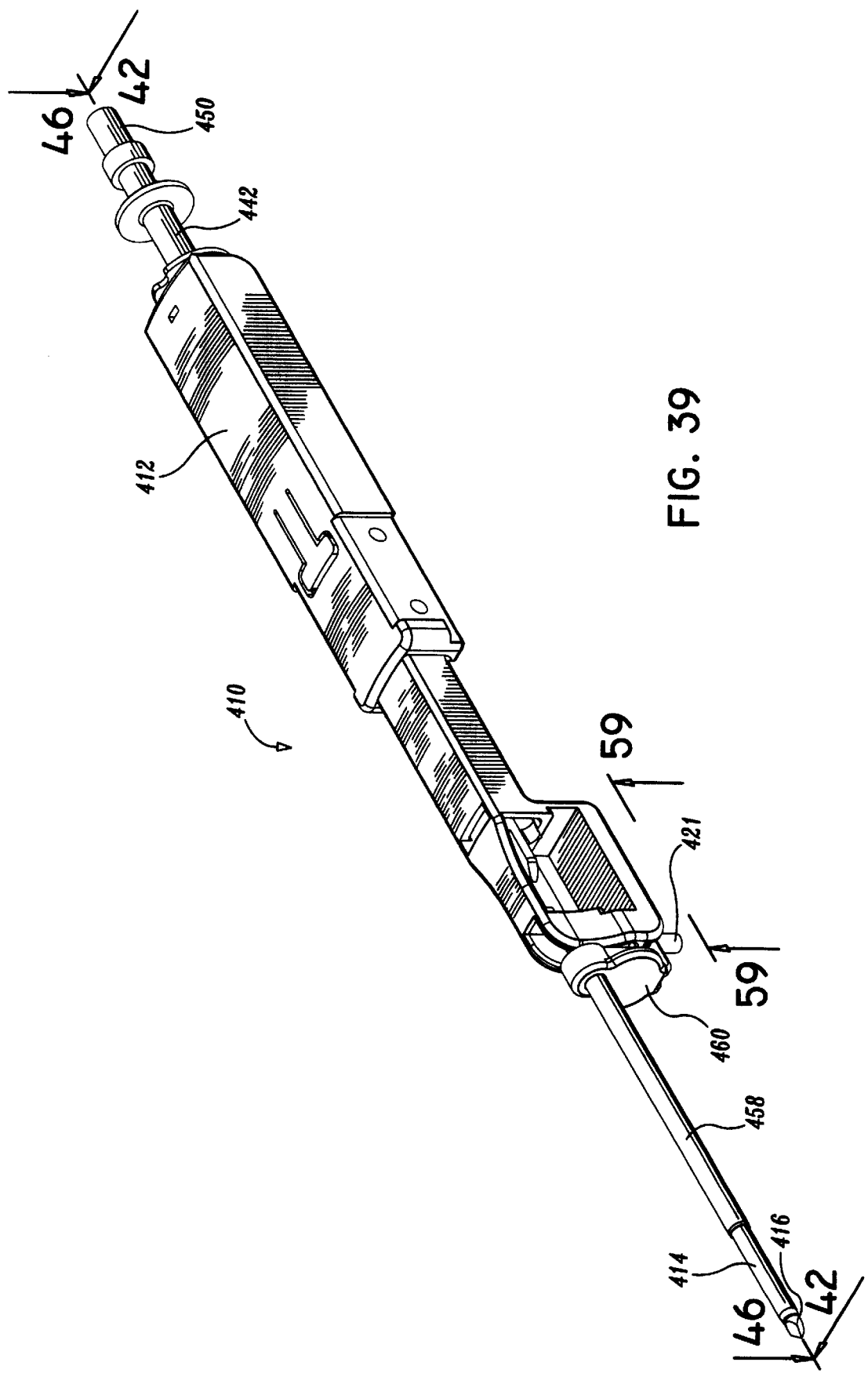
FIG. 39 is a perspective view of a disposable loading unit portion of the percutaneous biopsy apparatus of FIG. 38.

Referring again to FIGS. 39 and 40, a radiolucent outer tube 458 is attached to a sliding clip 460 which provides removable attachment to housing 412 at the distal end thereof. Outer tube 458 is radiolucent so that it may be left at the tissue sampling site for imaging of the suspect tissue without the presence of the radiopaque stainless steel knife tube 414 and vacuum tube 430. Outer tube 458 is preferably provided with radiopaque lines formed to indicate the longitudinal spacing of tissue basket 434 in order to provide the user with an indication of the tissue sampling area.

Figure 59:
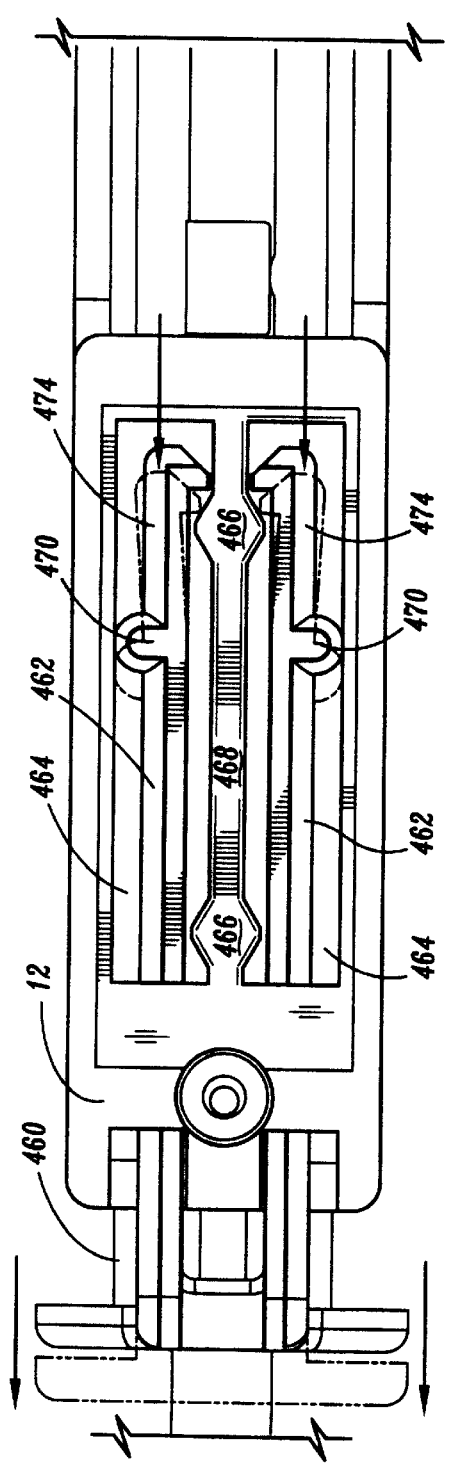
FIG. 59 is a sectional view taken along section line 59—59 of FIG. 39, which shows the removal of an outer tube from the disposable loading unit of the biopsy apparatus.
Figure 60:
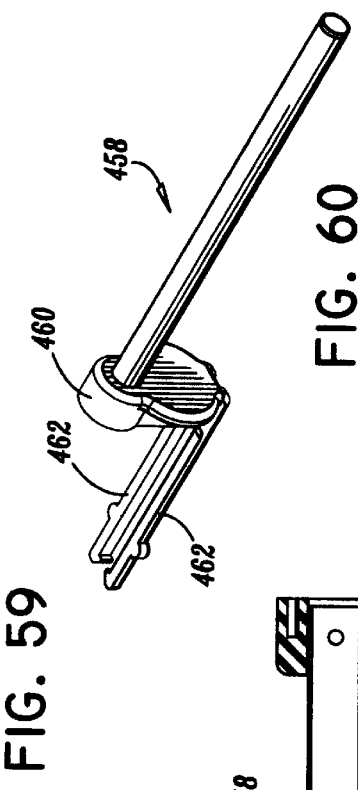
FIG. 60 is a perspective view of an outer tube of the biopsy apparatus.
Figure 61:
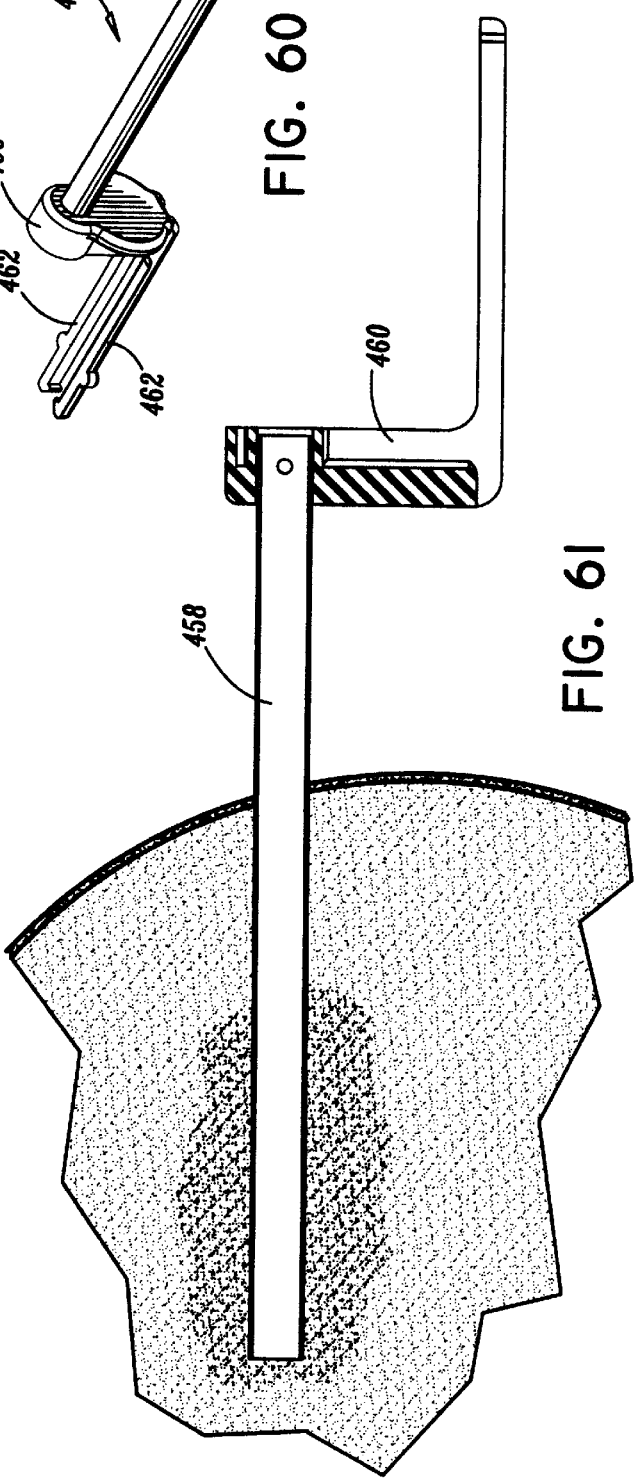
FIG. 61 is a side cross-sectional view showing the outer tube of FIG. 60 retained in a patient's breast after removal of the biopsy apparatus.
Figure 65:
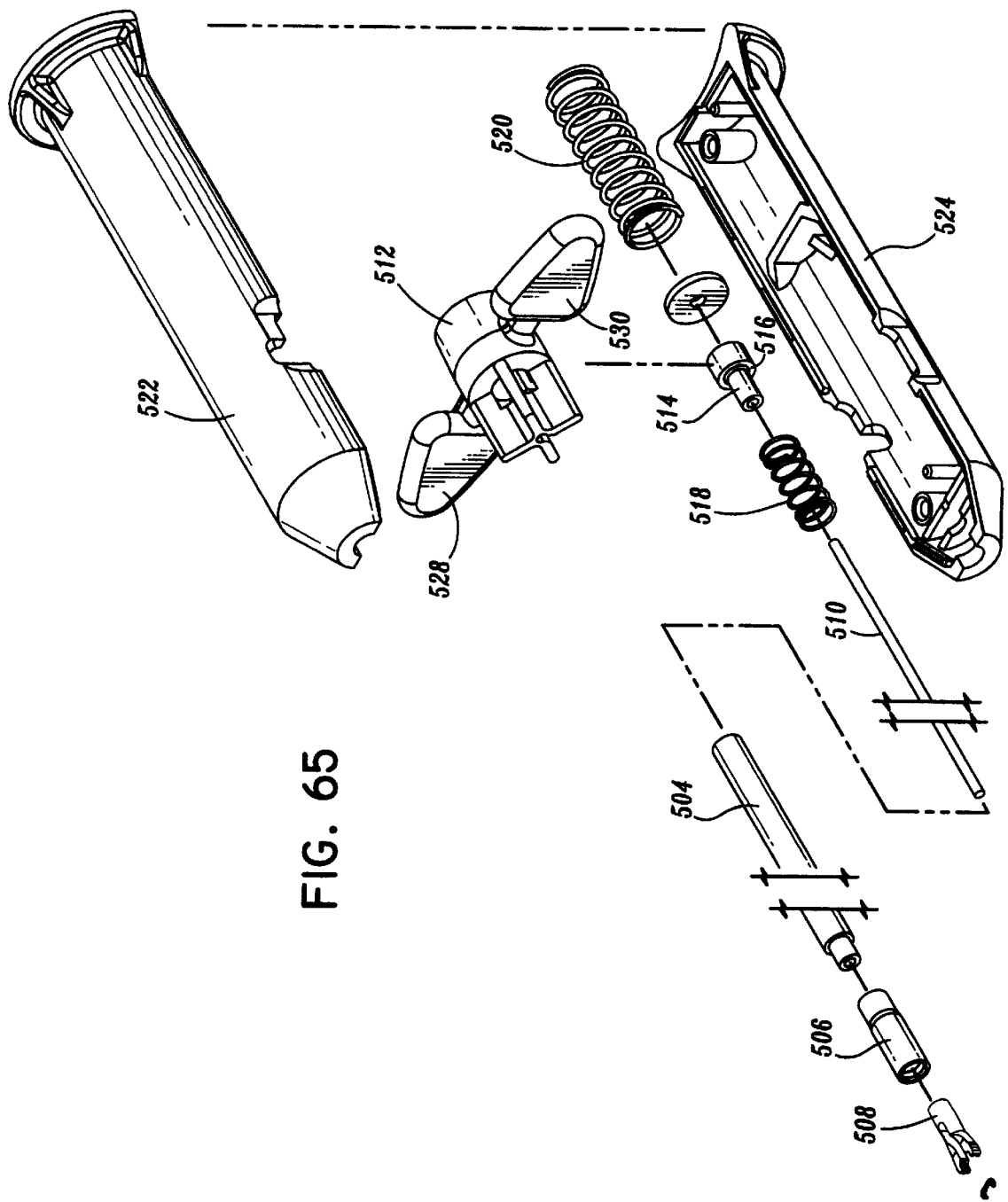
FIG. 65 is a perspective view with parts separated showing the components of the tissue marking apparatus of FIG. 62.
Figure 69:
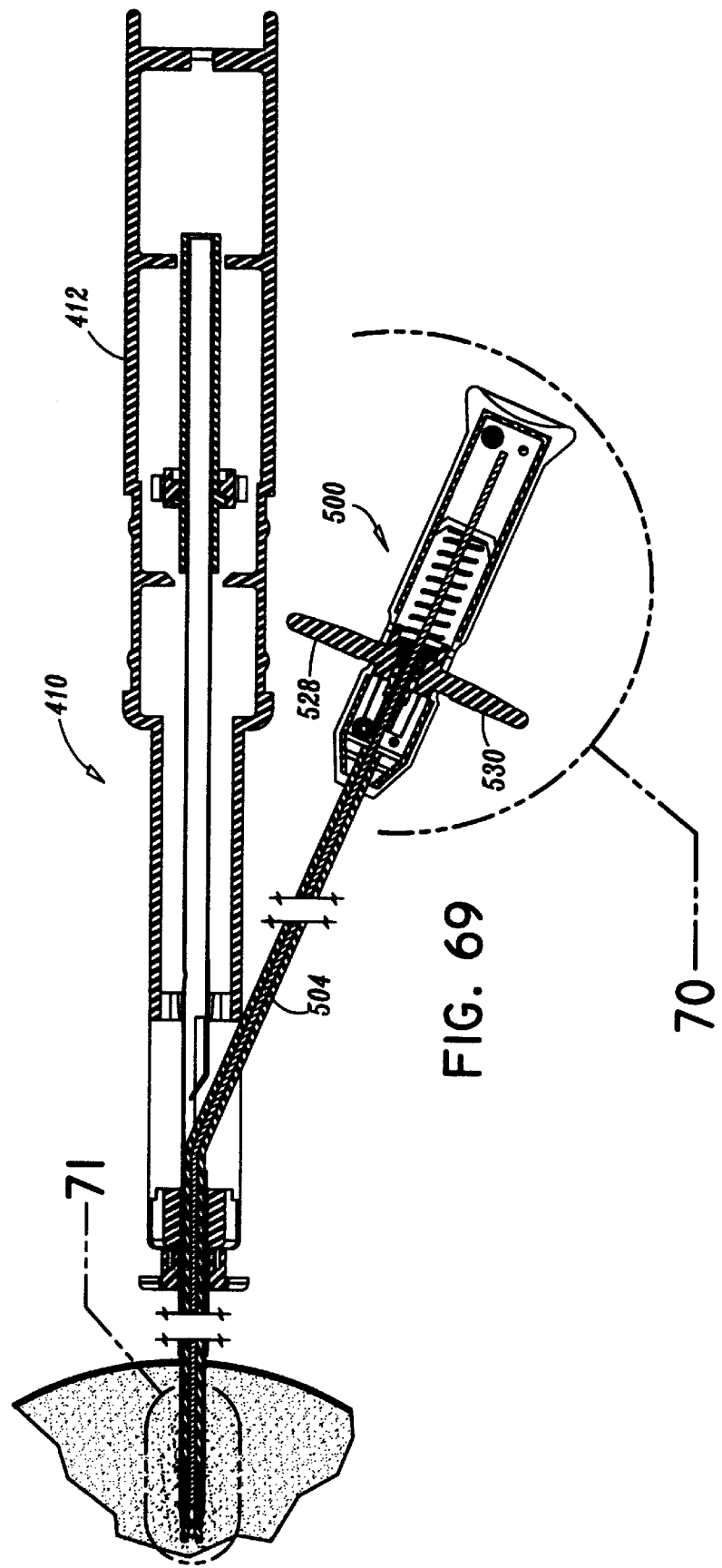
FIG. 69 is a cross-sectional view of the tissue marking apparatus inserted within the biopsy apparatus and into breast tissue of a patient.
Figure 70:
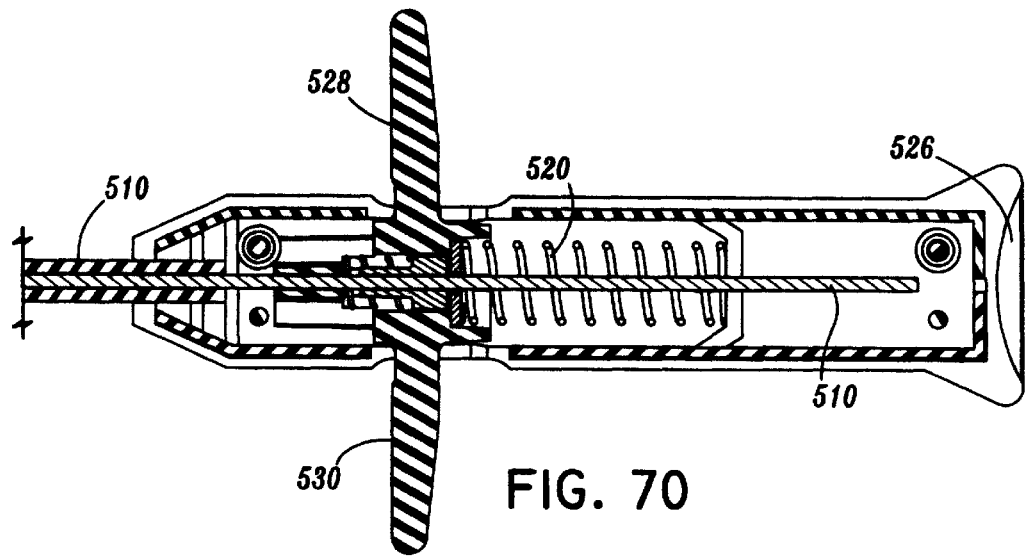
FIG. 70 is an enlarged view of the indicated area of detail shown in FIG. 69.
Figure 71:
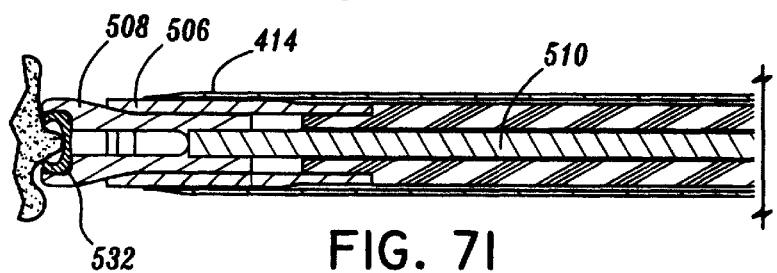
FIG. 71 is a cross-sectional view of the distal end portion of the tissue marking apparatus with a clip being disposed around tissue at the tissue sampling site.
Figure 72:
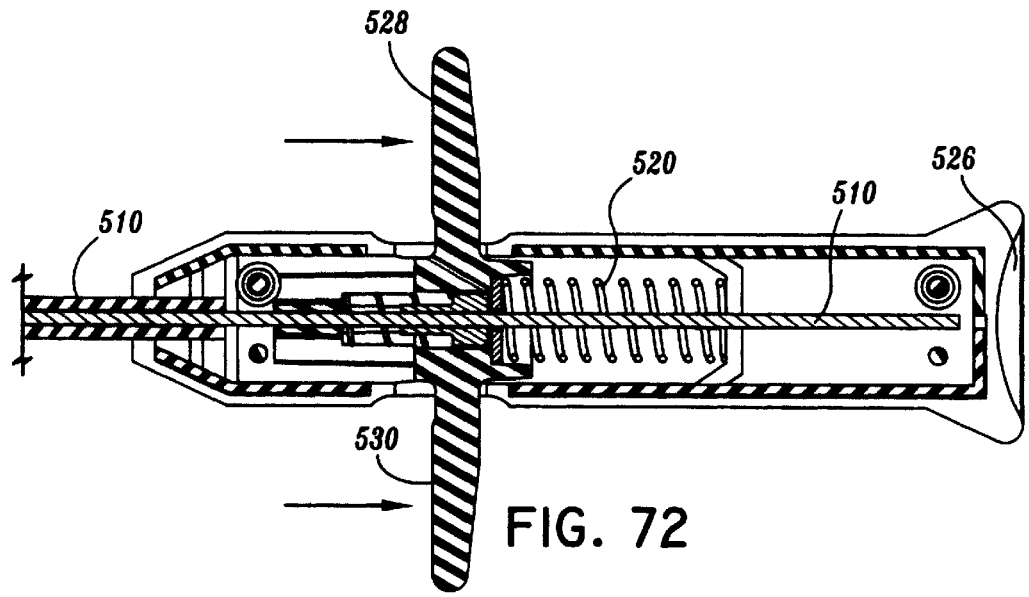
FIG. 72 is a cross-sectional view of the proximal end portion of the tissue marking apparatus.
Figure 73:
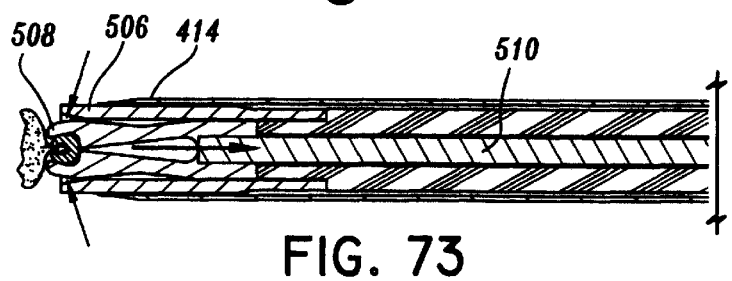
FIG. 73 is a view similar to FIG. 71, which shows deployment and formation of the clip at the tissue sampling site.

Referring temporarily to FIGS. 59–61, and initially to FIG. 59, the mounting of sliding clip 460 to housing 412 is shown. In particular, sliding clip 460 is provided with a pair of deflectable legs 462 which fit within parallel receiving slots 464 formed on the underside of housing 412. A pair of diamond-shaped camming surfaces 466 are formed along wall portion 468 which separates parallel slots 464. Camming surfaces 466 act as temporary stops which resist longitudinal movement of sliding clip 460. To facilitate this resistance, a pair of laterally facing tabs 470 are formed on the outer facing portions of each of flexible legs 462 and provide a bearing surface to flexible legs 462 against the inner wall of parallel slots 464. In this manner, proximal portions 474 of flexible legs 462 are cantilevered outwardly as they pass over camming surfaces 466. Upon complete distal movement of sliding clip 460 over camming surfaces 466, the distal end of outer tube 458 is substantially aligned with the distal end portion of the location of tissue basket 434 at insertion in the target tissue mass thus providing a marker for the location of the tissue sampling site upon removal of apparatus 412 from the suspect tissue region.

Referring to FIGS. 48–61, the operation of biopsy apparatus 410 will now be described for use in connection with a biopsy procedure performed on a breast of a patient. It is to be understood, however, that the procedures described herein may also be utilized in connection with the biopsy of tissue in other regions of the body as well. Much of the operational procedures are the same as or similar to those described above in connection with the other embodiments of the present disclosure. Accordingly, the following description will focus mainly on the features of biopsy apparatus 410. Some of the procedures previously described for other embodiments will, however, be described again at this point for the convenience of the reader.

Figure 48:
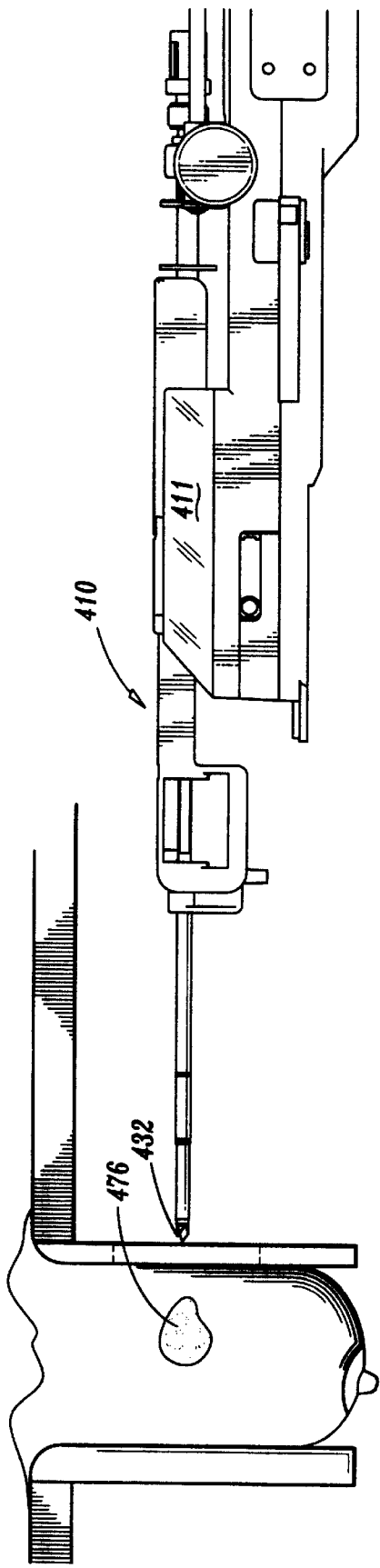
FIG. 48 is a side view illustrating the relative alignment of the biopsy apparatus with a target tissue means in a clamped breast prior to insertion of a penetrating tip.
Figure 49:
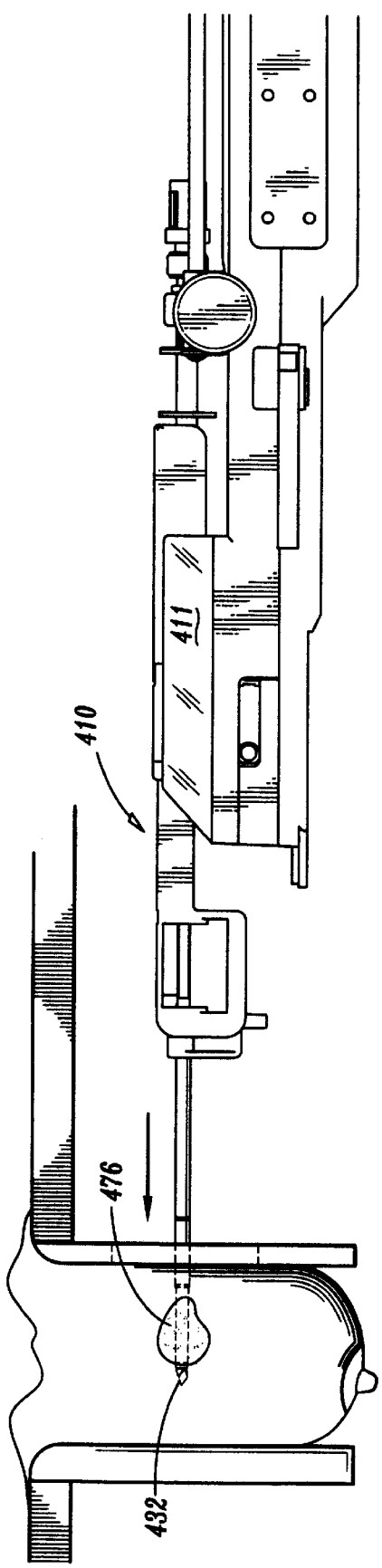
FIG. 49 is a view similar to FIG. 48 showing the penetration of the target tissue by the biopsy apparatus embodiment of FIG. 39.

As shown in FIG. 48, biopsy apparatus 410 which is mounted to a driver unit 411, which in turn is mounted to the instrument stage of a stereotactic imaging table, are positioned in alignment with a suspect tissue mass 476, the exact position of which has been previously identified by the use of the stereotactic imaging apparatus. Utilizing the positioning capabilities of the stereotactic imaging apparatus, biopsy apparatus 410 is positioned such that penetrating tip 432 is aligned with the center of the targeted tissue mass 476. Biopsy apparatus 410 may be either manually advanced through the tissue mass targeted such that tissue basket 434 spans the entire longitudinal distance of tissue mass 476 relative to tissue basket 434. In procedures where the targeted tissue mass exceeds the length of tissue basket 434, the instrument may first be inserted all the way to one end of the tissue mass wherein that end of the tissue may be removed through the procedure described herein and then the biopsy apparatus 410 moved such that the tissue basket aligns with the remaining tissue sample to be removed and the procedure repeated until all of the targeted tissue sample has been removed.

Referring to FIG. 50, when biopsy apparatus 410 is inserted through tissue sample 476, knife tube 414 is positioned over tissue basket 434 so as to prevent any tissue from prematurely entering the tissue basket prior to positioning of the tissue basket adjacent the desired suspect tissue mass 476. As shown in FIG. 51, once tissue basket 434 is positioned properly adjacent the suspect tissue mass 476, knife tube 414 is proximally retracted by releasing gear 424 from locking tab 478 disposed on housing 412 (FIG. 44). In this manner, tissue basket 434 is exposed and the vacuum source may be turned on so as to create a vacuum within tissue basket 434 thereby pulling in the portion of suspect tissue mass 476 adjacent tissue basket 434. With the suction continually applied, knife tube 414 is rotated and translated distally so as to sever the tissue included in tissue basket 434 by annular cutting surface 416. Knife tube 414 is preferably rotated and advanced distally by a motor provided in driver unit 412 which is connected by gearing to gear 424.

Once knife tube is fully distally advanced, locking wheel and indexer 442 is rotated until tab 446 clears the upper structure of housing 412 thereby releasing vacuum tube 430 and permitting withdrawal of the vacuum tube and, therefore, tissue basket 434 from within knife tube 414. The user can confirm that vacuum tube 430 is free to be withdrawn by the visual indication provided by notch 448 which is aligned with tab 446. Once vacuum tube 430 is withdrawn such that tissue basket 434 is adjacent to discharge opening 418 in knife tube 414, tissue stripping clip 452 will enter into tissue basket 434 such that inwardly deflected portion 456 contacts the proximal end of severed tissue sample 476A thereby urging the tissue sample out of the tissue basket 434 as shown in FIG. 58.

Upon completion of the desired amount of sampling, outer tube 458 is moved distally to position the radiopaque markers formed on outer tube 458 in relative alignment with the location of the site and length of the location where tissue basket 434 was previously aligned. Outer tube 458 may then be detached from biopsy apparatus 410 and the apparatus translated away from the tissue of the patient so that the tissue may be imaged without interference from the radiopaque nature of the remaining compounds of biopsy apparatus 410. Upon completion of the imaging, if it is determined that further sampling is desired or necessary, biopsy apparatus 410 may be re-inserted through outer tube 458 and 458 re-connected with housing 412 and additional sampling may be made as previously described herein.

Referring now to FIGS. 62–65, a tissue marking apparatus used in conjunction with the previously described biopsy apparatus 410 will now be described in detail. Tissue marking apparatus 500 includes an actuator housing 502 having an elongated flexible tubular sheath 504 extending from a distal end thereof with a camming tube 506 secured to a distal end of the flexible tubular sheath 504. A clip forming clamp member 508 is attached to the distal end of an actuator cable 510 which is tensionably mounted to actuator member 512. Cable 510 is mounted to actuator 512 by way of ferrule 514 which has a stepped shoulder portion 516 that seats within a stepped bore formed in actuator member 512. A pair of coil springs 518 and 520 are provided on either side of actuator member 512 within the housing and have relative spring forces to position actuator 512 in an initial orientation corresponding to an expanded state for clamp 508, as shown in FIG. 64. Housing 502 is formed as a split housing including housing components 522 and 524 which are snap-fitted together to house the actuation components.

When assembled, housing portions 522 and 524 form a thumb rest 526 to provide a bearing surface for the user's thumb when actuating tissue marking apparatus 500. Actuator 512 includes radially extending opposed finger bearing surfaces 528 and 530 which the user may grip in a syringe-like fashion to deploy and secure a clip 532 at the site of the biopsy within the patient. Tissue marking apparatus 500 further includes a pair of marking bands 534 and 536 which assist in orienting tissue marking apparatus relative to biopsy apparatus 410.

Referring now to FIGS. 66–73, in use tissue marking apparatus 500 is inserted within tissue discharge opening 418 of knife tube 414 so that the distal end portion of tissue marker apparatus 500 extends from the distal end portion of knife tube 414 beyond annular cutting surface 416, as shown in FIG. 68. Advantageously, the distal end portion of tissue marker apparatus 500 extends centrally through and exits centrally from knife tube 414 for clip placement in alignment with the longitudinal axis of biopsy apparatus 410. The user is provided with a visual indication of such alignment when tissue marking bands 536 and 534 straddle the distal end of tissue discharge opening 418 as shown in FIG. 67. With tissue marking apparatus 500 inserted in biopsy apparatus 410, the user grasps tissue marking apparatus much in the same manner as for grasping the plunger of a syringe and pulls back on tissue finger biasing surfaces 528 and 530 of actuator 512. This action pulls cable 510 proximally thereby drawing clip forming clamp 508 within camming tube 506 to attach clip 532 at the site of the sampled tissue. In this manner, the biopsy apparatus 410 as well as outer tube 458 may be completely removed from the patient thereby marking the biopsy site to provide an indication of the exact location of the biopsy for future reference, for example, in further imaging of the site or should the need arise in further biopsying of the site.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical biopsy apparatus which comprises:
    a housing;
    a first elongated tubular member removably mounted in the housing and defining a fluid passageway therein, the first elongated tubular member including:
        a tapered closed distal end portion adapted to penetrate tissue;
        a laterally disposed tissue receiving opening formed near the tapered distal end which includes a tissue support surface defining a plurality of holes in fluid communication with the fluid passageway; and
    a second elongated tubular member rotatably and reciprocatingly disposed coaxially about the first elongated tubular member, the second elongated tubular member having a cutting edge formed at an open distal end thereof and a lateral tissue discharge port formed proximally of the cutting edge.

2. A surgical biopsy apparatus according to claim 1, which further comprises a third elongated tubular member removably supported by the housing and coaxially disposed about the first and second elongated tubular members, the third elongated member being movable from a retracted position to an extended position wherein a distal end portion is disposed laterally adjacent a distal-most position of the tissue receiving opening of the first elongated tubular member.

3. A surgical biopsy apparatus according to claim 2, wherein the third elongated member is radiolucent to permit the passage of x-rays therethrough.

4. A surgical biopsy apparatus according to claim 3, wherein the third elongated member includes a radiopaque marking formed on a portion of the third elongated member such that when the third elongated tubular member is in the deployed position the radiopaque marking is laterally adjacent the distal-most position of the tissue receiving opening of the first elongated tubular member.

5. A surgical biopsy apparatus according to claim 1 which further comprises a tissue stripping member disposed adjacent the lateral tissue discharge port, the tissue stripping member including a flexible extended portion configured and dimensioned to enter the tissue receiving opening of the first elongated tubular member upon alignment of the tissue receiving opening with the lateral tissue discharge port.

6. A surgical biopsy apparatus according to claim 5 wherein the tissue stripping member includes a friction reducing coating formed thereon to reduce friction with body tissue coming in contact with the tissue stripping member.

7. A surgical biopsy apparatus according to claim 1 wherein the tissue support surface of the laterally disposed tissue receiving opening has an arcuate cross-section.

8. A method of performing a surgical biopsy comprising the steps of:
    inserting a biopsy apparatus into the tissue of a patient, the biopsy apparatus including an inner tubular member having a tapered penetrating distal end and an outer tubular member held longitudinally fixed relative to the inner tubular member during the insertion step;
    retracting the outer tubular member relative to the inner tubular member to expose a laterally disposed tissue receiving area formed on the inner tubular member;
    applying suction to a series of openings formed along an inner surface of the tissue receiving area to pull tissue into the tissue receiving area;
    severing tissue disposed within the tissue receiving area by advancing the outer tubular member over the inner tubular member such that a cutting surface formed on the distal end of the outer tubular member rotates as it passes over the tissue receiving area; and
    removing the severed tissue sample from the tissue sampling site by retracting the inner tubular member from the outer tubular member until the tissue receiving area is aligned with a lateral opening formed in the outer tubular member wherein a tissue stripping plate urges the tissue sample out of the tissue receiving area.

9. A surgical biopsy apparatus which comprises:
    a housing;
    a first elongated tubular member removably mounted in the housing and defining a fluid passageway therein, the first elongated tubular member including:
        a tapered closed distal end portion adapted to penetrate tissue;
        a laterally disposed tissue receiving area formed near the tapered distal end portion; and
        a tissue support surface defining a plurality of holes in fluid communication with the fluid passageway; and
    a second elongated tubular member rotatably and reciprocatingly disposed coaxially about the first elongated tubular member, the second elongated tubular member having a cutting edge formed at an open distal end thereof.

* * * * *